(12) United States Patent
Krishna et al.

(10) Patent No.: US 11,712,462 B2
(45) Date of Patent: *Aug. 1, 2023

(54) PIC1 INHIBITION OF MYELOPEROXIDASE OXIDATIVE ACTIVITY IN AN ANIMAL MODEL

(71) Applicant: REALTA HOLDINGS, LLC, Norfolk, VA (US)

(72) Inventors: Neel K. Krishna, Norfolk, VA (US); Kenji Cunnion, Norfolk, VA (US)

(73) Assignee: REALTA HOLDINGS, LLC, Norfolk, VA (US)

( * ) Notice: Subject to any disclaimer, the term of this patent is extended or adjusted under 35 U.S.C. 154(b) by 148 days.

This patent is subject to a terminal disclaimer.

(21) Appl. No.: 17/245,213

(22) Filed: Apr. 30, 2021

(65) Prior Publication Data

US 2021/0252113 A1 Aug. 19, 2021

Related U.S. Application Data

(63) Continuation of application No. 16/839,464, filed on Apr. 3, 2020, now Pat. No. 11,020,460, which is a continuation of application No. 16/242,550, filed on Jan. 8, 2019, now Pat. No. 11,135,272.

(60) Provisional application No. 62/746,649, filed on Oct. 17, 2018, provisional application No. 62/681,458, filed on Jun. 6, 2018, provisional application No. 62/615,183, filed on Jan. 9, 2018.

(51) Int. Cl.
| | |
|---|---|
| *A61K 38/00* | (2006.01) |
| *A61K 38/43* | (2006.01) |
| *A61P 37/06* | (2006.01) |
| *A61K 47/10* | (2017.01) |
| *A61K 9/00* | (2006.01) |
| *A61K 38/08* | (2019.01) |
| *C07K 14/47* | (2006.01) |
| *C07K 14/005* | (2006.01) |

(52) U.S. Cl.
CPC ............ *A61K 38/43* (2013.01); *A61K 9/0019* (2013.01); *A61K 38/005* (2013.01); *A61K 38/08* (2013.01); *A61K 47/10* (2013.01); *A61P 37/06* (2018.01); *C07K 14/005* (2013.01); *C07K 14/4703* (2013.01); *C12N 2770/00022* (2013.01); *C12N 2770/00033* (2013.01)

(58) Field of Classification Search
CPC ...... A61K 47/10; A61K 38/43; A61K 38/005; A61K 38/08; A61P 37/06; C07K 14/005; C07K 14/4703
See application file for complete search history.

(56) References Cited

U.S. PATENT DOCUMENTS

| | | | |
|---|---|---|---|
| 6,126,939 A | 10/2000 | Eisenbach-Schwartz et al. | |
| 6,696,562 B1 | 2/2004 | Schultz-Cherry et al. | |
| 7,381,524 B2 | 6/2008 | Schultz-Cherry et al. | |
| 8,241,843 B2 | 8/2012 | Krishna et al. | |
| 8,906,845 B2 | 12/2014 | Krishna et al. | |
| 9,422,337 B2 | 8/2016 | Krishna et al. | |
| 9,914,753 B2 | 3/2018 | Krishna et al. | |
| 10,005,818 B2 | 6/2018 | Krishna et al. | |
| 10,414,799 B2 | 9/2019 | Krishna et al. | |
| 10,844,093 B2 | 11/2020 | Krishna et al. | |
| 10,933,116 B2 | 3/2021 | Krishna et al. | |
| 2005/0079485 A1 | 4/2005 | Schultz-Cherry et al. | |
| 2007/0012617 A1 | 1/2007 | Suzuki et al. | |
| 2009/0092581 A1 | 4/2009 | Skawinski et al. | |
| 2010/0055106 A1 | 3/2010 | Krishna et al. | |
| 2011/0104156 A1 | 5/2011 | Christadoss et al. | |
| 2013/0183662 A1 | 7/2013 | Zychlinsky et al. | |
| 2013/0244924 A1 | 9/2013 | Krishna et al. | |
| 2014/0309175 A1 | 10/2014 | Zhao et al. | |
| 2015/0031599 A1 | 1/2015 | Abuchoswski et al. | |
| 2015/0064176 A1 | 3/2015 | Schwaeble et al. | |
| 2016/0376322 A1* | 12/2016 | Krishna ............... | C07K 14/005 514/2.7 |
| 2019/0010193 A1 | 1/2019 | Krishna et al. | |

FOREIGN PATENT DOCUMENTS

| | | |
|---|---|---|
| JP | 2013-533273 A | 8/2013 |
| WO | 94/26902 | 11/1994 |
| WO | 99/44625 A1 | 9/1999 |
| WO | 00/43027 A1 | 7/2000 |

(Continued)

OTHER PUBLICATIONS

Weinstock et al. "Successful use of eculizumab for treatment of an acute hemolytic reaction after ABO-incompatible red blood cell transfusion", Transfusion, 2015, vol. 55, No. 3, pp. 605-810.
Frank et al. ed, "Complement System", In: Austen KF, Atkinson JP, Cantor HI ed. Samter's Immunologic Disease. New York: Lippincott Williams and Wilkins; 2001; pp. 281-299.
Shah et al., "Complement inhibition significantly decreases red blood cell lysis in a rat model of acute intravascular hemolysis", Transfusion, 2014, vol. 54, No. 11, pp. 2892-2900.

(Continued)

*Primary Examiner* — Jeanette M Lieb
(74) *Attorney, Agent, or Firm* — Troutman Pepper Hamilton Sanders LLP

(57) ABSTRACT

A method of treating systemic lupus erythematosus in a subject is provided in which a therapeutically effective amount of PIC1 is administered to the subject. A method of treating transfusion-related acute lung injury is also provided where a therapeutically effective amount of PIC1 is administered to the subject. PIC1 can modulate immune complex activation of the complement system and NET formation in the subject. PIC1 can also inhibit myeloperoxidase (MPO) activity in the subject.

18 Claims, 25 Drawing Sheets
(8 of 25 Drawing Sheet(s) Filed in Color)
Specification includes a Sequence Listing.

(56) References Cited

FOREIGN PATENT DOCUMENTS

| WO | 2005/023195 | 3/2005 |
|---|---|---|
| WO | 2005/023296 | 3/2005 |
| WO | 2007/145806 | 12/2007 |
| WO | 2012/012600 | 1/2012 |

OTHER PUBLICATIONS

Aptekman et al.,"Characterization of the natural hemagglutinins in normal rat serum associated with a negative phase following tumor implantation." Cancer Research, 1956, vol. 16, No. 3, pp. 216-221.
Yazdanbakhsh et al., "Complement receptor 1 inhibitors for prevention of immunemediated red cell destruction: potential use in transfusion therapy." Blood, Jun. 2003, vol. 101, No. 12, pp. 5046-5052.
Boyle, "Adult cystic fibrosis", JAMA, 2007, vol. 298, No. 15, pp. 1787-1793.
Rowe et al., "Cystic fibrosis", The New England Journal of Medicine, 2005, vol. 352, No. 19, pp. 1992-2001.
Gibson et al., "Pathophysiology and management of pulmonary infections in cystic fibrosis." Am J Respir Crit Care Med, 2003, vol. 168, No. 8, pp. 918-951.
Gharib et al., "Mapping the lung proteome in cystic fibrosis", Journal of Proteome Research, 2009, vol. 8, No. 6, pp. 3020-3028.
Lambris et al., "The chemistry and biology of C3, C4, and C5." In: Volanakis JE, Frank MM, (eds). The human complement system in health and disease. New York: Marcel Dekker; 1998, 83-118.
Tralau et al., "Human leukocyte elastase and cathepsin Gare specific inhibitors of CS a-dependent neutrophil enzyme release and chemotaxis", Experimental Dermatology, 2004, vol. 13, No. 5, pp. 316-325.
Dwyer et al., "Cystic Fibrosis Sputum DNA Has NETosis Characteristics and Neutrophil Extracellular Trap Release Is Regulated by Macrophage Migration-Inhibitory Factor", Journal of Innate Immunity, 2014, vol. 6, pp. 765-779.
Hodson, "Aerosolized domase alfa (rhDNase) for therapy of cystic fibrosis", American Journal of Respir Crit Care Med, 1995, vol. 151, (3 Pt 2), pp. S70-S74.
Gifford et al., "The role of neutrophils in cystic fibrosis", Current Opinion Hematology, 2014, vol. 21, No. 1, pp. 16-22.
Le Gars et al., "Neutrophil elastase degrades cystic fibrosis transmembrane conductance regulator via cal pains and disables channel function in vitro and in vivo", Am J Respir Crit Care Med, 2013, vol. 187, Issue 2, pp. 170-179.
Sagel et al., "Sputum biomarkers of inflammation and lung function decline in children with cystic fibrosis", American Journal Respiratory Critical Care Medicine, 2012, vol. 186, No. 9, pp. 857-865.
Schmudde et al., "C5a receptor signalling in dendritic cells controls the development of maladaptive Th2 and Th17 immunity in experimental allergic asthma", Mucosal Immunology, 2013, vol. 6, No. 4, pp. 807-825.
Bosmann et al., "Role of C3, C5 and anaphylatoxin receptors in acute lung injury and in sepsis", Adv Exp Med Biol., 2012, vol. 946, pp. 147-159.
Fick et al., "Complement activation in cystic fibrosis respiratory fluids: In vivo and in vitro generation of C5a and chemotactic activity", Pediatric Research, 1986, vol. 20, No. 12, pp. 1258-1268.
Shah et al. "Clinical hypothermia temperatures increase complement activation and cell destruction via the classical pathway", Journal of Translational Medicine, 2014, vol. 12, 181.
Koseoglu at al., "Effects of hemolysis interferences on routine biochemistry parameters", Biochemia medica, 2011, vol. 21, No. 1, pp. 79-85.
Schwartz et al., "Hyperbilirubinemia: current guidelines and emerging therapies." Pediatric emergency care. 2011; vol. 27, No. 9, pp. 884-889.
"Management of hyperbilirubinemia in the newborn infant 35 or more weeks of gestation", American Academy of Pediatrics, 2004, vol. 114, No. 1, pp. 297-316.
Cortey et al., "Efficacy and safety of intravenous immunoglobulins in the management of neonatal hyperbilirubinemia due to ABO incompatibility: a meta-analysis." Archives de pediatrie : organe ofjiciei de la Societe francaise de pediatrie. 2014; vol. 21, No. 9, pp. 976-983.
Strobel E., "Hemolytic Transfusion Reactions", Transfusion medicine and hemotherapy : ofjizieiles Organ der Deutschen Gesellschaft fur Transfusionsmedizin und Immunhamatologie, 2008; vol. 35, No. 5, pp. 346-353.
Davies et al., "Identification of MUC5B, MUC5AC and small amounts of MUC2 mucins in cystic fibrosis airway secretions", Biochem J., 1999, vol. 344 Pt 2: 321-330.
Hair et al., "Hyperglycemic conditions inhibit C3-mediated immunologic control of Staphylococcus aureus", Journal of Translational Medicine, 2012, vol. 10, No. 35, 16 pages.
Mollnes et al., "Essential role of the C5a receptor in E coli-induced oxidative burst and phagocytosis revealed by a novel lepirudin-based human whole blood model of inflammation", Blood, 2002, vol. 100, No. 5, pp. 1869-1877.
Laursen et al., "Structure, function and control of complement C5 and its proteolytic fragments", Current Molecular Medicine, 2012, vol. 12, No. 8, pp. 1083-1097.
Japanese Office Action Issued in Japanese Patent Application No. 2018-519267 dated May 18, 2020.
Voelker and Spieth, Blood transfusion associated lung injury, J. Thorac. Dis. 2019;11(8):3609-3615.
Kumar et al., Ventilator-Induces Lung Injury (VILS), NCBI Bookshelf, 2020, 8 pages.
Schmidt et al., Pathology Consultation on Transfusion-Reiatad Acute Lung Injury (TRALI), Am. J. Clin. Pathol, 2012, pp. 498-503.
Lee et al., "Overview of COVID-19 inflammatory pathogenesis from the therapeutic perspective", Arch. Pharm. Res., 2021, 18 pages.
Arroyo-Hernandez et al., "Radiation-induced lung injury: current evidence", BMC Pulm Med., 2021, vol. 21, No. 9, 12 pages.
Klomp et al., "From virus to inflammation, how influenza promotes lung damage", Journal of Leukocyte Biology, 2020, 8 pages.
Diamond et al., "Acute Respiratory Distress Syndrome", NCBI Bookshelf, 2020, 8 pages.
Ragaller et al., "Acute Lung Injury and acute respiratory distress syndrome", J. Emerg. Trauma Shock, 2010, vol. 3, No. 1, pp. 43-51.
Ricklin and Lambris, "Complement-targeted therapeutics," Author Manuscript, published in final form as: Nat. Biotech., 25, pp. 1265-1275 (2007).
Bonaparte et al., "Human Astrovirus Coat Protein Inhibits Serum Complement Activation via C1, the First Component of the Classical Pathway," J. Virol., 82(2), pp. 817-827 (2008).
Carvalho and Gomes, "Plant defensins-prospects for the biological functions and biotechnological properties," Peptides, 30(5), pp. 1007-1020 (2009).
Castellano et al., "Therapeutic targeting of classical and lectin pathways of complement protects from ischemia-reperfusion-induced renal damage," Amer. J. Pathol., 176, pp. 1648-1659 (2010).
Cunnion et al., "Capsule production and growth phase influence binding of complement to Staphylococcus aureus," Infect. Immun., 69, pp. 6796-6803 (2001).
Fryer et al., "Synthetic peptides which inhibit the interaction between C1q and immunoglobulin and prolong xenograft survival," Transplantation, 70, pp. 828-836 (2000).
Groeneveld, et al., "Human neutrophil peptide-1 inhibits both the classical and the lectin pathway of complement activation," Molec. Immunol., vol. 44, pp. 3608-3614 (2007).
Hair et al. "Human astrovirus coat protein binds C1q and MBL and inhibits the classical and lectin pathways of complement activation," Molecular Immunology, 47, pp. 792-798 (2010).
Huwiler et al., "Optimizing the MALDI-TOF-MS observation of peptides containing disulfide bonds," J. Biomol. Tech., 14, pp. 289-297 (2003).
Kojima et al., "Inhibition of complement-mediated immune hemolysis by peptides derived from the constant domain of immunoglobulin," Transplantation, 67, pp. 637-638 (1999).
Larkin et al., "Clustal W and Clustal X version 2.0," Bioinformatics, vol. 23, No. 21, pp. 2947-2948 (2007).

(56) References Cited

OTHER PUBLICATIONS

Lauvrak et al., "Identification and characterization of C1q-binding phage displayed peptides," Biol. Chem., 378, pp. 1509-1519 (1997).
Lee et al., "Early complement factors in the local tissue Immunocomplex generated during intestinal ischemia/reperfusion injury," Author Manuscript, published in final form as: Mol. Immunol., 47, pp. 972-981 (2010).
Liu et al., "Solution structure of the plant defensin VrD1 from mung bean and its possible role in insecticidal activity against bruchids," Proteins, 63, pp. 777-786 (2006).
Lund et al., "X3M a Computer Program to Extract 3D Models," Abstract at the CASP5 conference A102, 2002 (2 pages).
Mallik et al, "Design and NMR characterization of active analogs of Compstatin containing non-natural amino adds," J. Med. Chem., 48, pp. 274-286 (2005).
Messmer et al., "Sequential determination of ligands binding to discrete components in heterogeneous mixtures by iterative panning and blocking (IPAB)," J. Mol. Biol., 296, pp. 821-832 (2000).
Roos et al., "Specific inhibition of the classical complement pathway by C1q-binding peptides," J. Immunol., 167, pp. 7052-7059 (2001).
Sahu et al., "Inhibition of human complement by a C3-binding peptide isolated from a phage-displayed random peptide library," J. Immunol., 157, pp. 884-891 (1996).
Taylor et al., "Structure-activity relationships in beta-defensin peptides," Biopolymers, 90, pp. 1-7 (2007).
Tjernberg et al., "Acute antibody-mediated complement activation mediates lysis of pancreatic islets cells and may cause tissue loss in clinical islet transplantation," Transplantation, 85, pp. 1193-1199 (2008).
Van den Berg et al., "Inhibition of activation of the classical pathway of complement by human neutrophil defensins," Blood, 92, pp. 3898-3903 (1998).
Zhang et al., "Activation of the lectin pathway by natural IgM in a model of ischemia/reperfusion injury," J. Immunol., 177, pp. 4727-4734 (2006).
Zhang et al., "NMR studies of defensin antimicrobial peptides. 1. Resonance assignment and secondary structure determination of rabbit NP-2 and human HNP-1," Biochemistry, 31, pp. 11348-11356 (1992).
Bass et al., "Characterization of Human Serotype 1 Astrovirus-Neutralizing Epitopes," Journal of Virology, 71(11), pp. 8666-8671 (1997).
Bass et al., "Proteolytic processing of the astrovirus capsid," J. Virol. 74(4), pp. 1810-1814 (2000).
Caballero et al. "Structural requirements of astrovirus virus-like particles assembed in insect cells," J. Virol. 78(23), pp. 13285-13292 (Dec. 2004).
Cooper, "The classical complement pathway: activation and regulation of the first complement component," Adv. Immunol., 37, pp. 151-216 (1985).
Dong et al., "Particle polymorphism caused by deletion of a peptide molecular switch in a quasiequivaient icosahedra virus," J. Virol., 72(7), pp. 6024-6033 (1998).
Favoreel et al., "Virus complement evasion strategies," Journal of General Virology, 84(Pt. 1), pp. 1-15 (2003).
Fogh, ed., "Human tumor cells in vitro," Plenum Press, pp. 115-159 (1975) (47 total pages).
Geigenmüller et al., "Construction of a genome-length CDNA clone for human astrovirus serotype 1 and synthesis of infectious RNA transcripts," J. Virol., 71, pp. 1713-1717 (1997).
GenBank, "Human astrovirus putative serine protease gene, complete cds; putative RNA-dependent RNA polymerase gene, partial cds; and capsid precursor protein gene, complete cds," Accession No. AF141381, <http://www.ncbi.nim.nih.gov/nuccore/AF141381> retrieved on Nov. 24, 2011 (3 pages).
GenBank, "Human astrovirus type 1 genes for capsid protein and nonstructural protein," Accession No. Z25771, <http://www.ncbi.nim.nih.gov/nuccore/z25771> retrieved on May 15, 2013 (5 pages).
GenBank, "non-structural protein, capsid protein (human astrovirus serotype 1, isolate A88/2, Newcastle, Genomic RNA, 2739 nt)," Accession No. S68561, <http://www.ncbi.nim.nih.gov/nuccore/S68561> entered in database Jul. 21, 2000 (2 page).
Gronemus et al., "Potent inhibition of the classical pathway of complement by a novel C1q-binding peptide derived from the human astrovirus coat protein," Molecular Immunology, 48, pp. 305-313 (2010).
Harris and Chess, "Effect of pegylation on pharmaceuticals," Nature Reviews Drug Discovery, 2, pp. 214-221 (Mar. 2003).
International Search Report and Written Opinion for International Application No. PCT/US2007/012617, dated Jun. 4, 2008, 11 pages.
International Search Report and Written Opinion for International Application No. PCT/US2011/044791, dated Mar. 21, 2012, 14 pages.
Kohno et al., "Development of Simple Latex Agglutination Test for Detection of Astrovirus Serotype 1," JARMAM, 11 (2), pp. 87-91 (2000).
Krishna et al., "Human Astrovirus Coat Protein: A Novel C1 Inhibitor," Adv. Exp. Med. Biol., 632, pp. 237-251 (2008).
Krishna, "Identification of structural domains involved in astrovirus capsid biology," Viral Immunol., 18(1), pp. 17-26 (2005).
Mendez-Toss et al., "Molecular Analysis of a Serotype 8 Human Astrovirus Genome," Journal of General Virology, 81, pp. 2891-2897 (2000).
Morgan and Harris, "Complement therapeutics; history and current progress," Molec. Immunol., 40, pp. 159-170 (2003).
Noris and Remuzzi, "Overview of Complement Activation and Regulation," Semin. Nephrol., 33(6), pp. 479-492 (2013).
Park et al., "A Readily Applicable Strategy to Convert Peptides to Peptoid-based Therapeutics," PLoS One, 8, e58874, pp. 1-7 (2003).
Sambrook and Russell, "Molecular cloning: A Laboratory Manual," Cold Spring Harbor Laboratory Press, 3rd ed., 21 pages (2001).
Scheneemann et al., "Use of recombinant baculoviruses in synthesis of morphologically distinct viruslike particles of flock house virus, a nodavirus," J. Virol., 67, pp. 2756-2763 (1993).
ScienceDaily, "Research could lead to way to halt deadly immune response," <http://www.sciencedaily.com/release/2010/021100209183127.htm>, 2 pages (2010).
Sharp et al., "Peptide Inhibitor of complement C1, a novel suppressor of classical pathway activation: mechanistic studies and clinical potential," Frontiers in Immunology, vol. 5, article 406, 9 pages (Aug. 22, 2014).
Supplementary European Search Report issued by the European Patent Office for European Patent Application No. 07809212, 3 pages; dated Sep. 10, 2010.
Thermo Electron Corporation, "N-Terminal Acetylation and C-Terminal Amidation of Peptides," Technical Information, 2 pages (2004).
UniProtKB/TrEMBL, "Capsid Protein—Human Astrovirus-1 (HAstV-1)," 3 pages, <http://www.uniprot.org/uniprot/A9CE26> (Jul. 22, 2008).
Vaughn et al., "T he establishment of two cell lines from the insect *Spodoptera frugiperda* (Lepidoptera; Noctuidae)," In Vitro, 13, pp. 213-217 (1977).
Willcocks et al., "Growth and characterisation of human faecal astrovirus in a continuous cell line," Arch. Virol., 113, pp. 73-81 (1990).
Younger et al., "Systemic and lung physiological changes in rats after intravascular activation of complement," J. Appl. Physiol., 90, pp. 2289-2295 (2001).
Aleyd et al., "IgA Complexes in Plasma and Synovial Fluid of Patients with Rheumatoid Arthritis Induce Neutrophil Extracellular Traps via Fc alphaRI". Ths Journal of Immunology, 2016, vol. 197, No. 12, pp. 4552-4559.
Akong-Moore et al., "Influences of chloride and hypochlorite on neutrophil extracellular trap formation", PLoS ONE, 2012, vol. 7, Issue 8, e42984, 7 pages.
Ballanti et al., "Complement and Autoimmunity". Immunologic Research, 2013, vol. 56, No. 2-3, pp. 477-491.

(56) References Cited

OTHER PUBLICATIONS

Bassi et al., "PTX3, Anti-PTX3, and Anti-C1q Autoantibodies in Lupus Glomerulonephritis", Clinical Reviews in Allergy & Immunology, 2015, vol. 49, No. 2, pp. 217-226.

Barilla-Labarca et al., "Targeting the complement system in systemic lupus erythematosus and other diseases", Clinical Immunology. 2013, 148, No. 3, pp. 313-321.

Behnen et al., "Immobilized immune complexes induce neutrophil extracellular trap release by human neutrophil granulocytes via Fcgamma RIIIB and Mac-1", The Journal of Immunology, 2014, vol. 193, No. 4, pp. 1954-1965.

Bergseth et al., "An international serum standard for application in assays to detect human complement activation products", Molecular Immunology, 2013, vol. 56, No. 3, pp. 232-239.

Bestebroer et al., "Functional basis for complement evasion by staphylococcal superantigen-like 7", Cellular Microbiology, 2010, vol. 12, No. 10, pp. 1506-1516.

Carlin et al., "Statistics for clinicians: 4: Basic concepts of statistical reasoning: hypothesis tests and the t-test". Journal of Paediatrics and Child Health, 2001, vol. 37, No. 1, pp. 72-77.

Chen et al., "Endocytosis of soluble immune complexes leads to their clearance by FcgammaRIIIB but induces neutrophil extracellular traps via FcgammaRIIA in vivo", Blood, 2012, vol. 120, No. 22, pp. 4421-4431.

Coulthard et al., "Is the Complement Activation Product C3a a Proinflammatory Molecule? Re-evaluating the Evidence and the Myth" The Journal of Immunology, 2015, vol. 194, No. 8, pp. 3542-3548.

Daha, N.A. et al., "Complement activation by (auto-) antibodies". Molecular Immunology. 2011, 48(14):1656-1665.

Hair et al., "Clumping factor A Interaction with complement factor I increases C3b cleavage on the bacterial surface of *Staphylococcus aureus* and decreases complement-mediated phagocytosis", Infection and Immunity, 2010, vol. 78, No. 4, pp. 1717-1727.

Hair et al., "Inhibition of Myeloperoxidase Activity in Cystic Fibrosis Sputum by Peptide Inhibitor of Complement C1 (PIC1)", PLoS ONE, 2017, vol. 12, No. 1, 13 pages.

Hair et al., "Peptide inhibitor of complement C1 inhibits the peroxidase activity of hemoglobin and myoglobin", Hindawi International Journal of Peptides, vol. 2017; Article ID 9454583, 10 pages.

Knight et al., "Lupus neutrophils: 'NET' gain in understanding lupus pathogenesis", Current Opinion in Rheumatology, 2012, vol. 24, No. 5, pp. 441-450.

Kraaij et al., "A novel method for high-throughput detection and quantification of neutrophil extracellular traps reveals ROS-independent NET release with immune complexes", Autoimmunity Reviews, 2016, vol. 15, No. 6, pp. 577-584.

Kumar, P.S. et al., "Glucose-based dialysis fluids inhibit innate defense against *Staphylococcus aureus*". Molecular Immunology. 2015, 67:575-583.

Kumar, P.S. et al., "Peptide Inhibitor of complement C1 modulates acute intravascular hemolysis of mismatched red blood cells in rats". Transfusion. 2016, 56(8):2133-2145.

Lood et al., "Neutrophil extracellular traps enriched in oxidized mitochondrial DNA are interferogenic and contribute to lupus-like disease", Nature Medicine, 2016, vol. 22, No. 2, pp. 146-153.

Lupia et al., "The membrane attack complex of complement contributes to plasmin-induced synthesis of platelet-activating factor by endothelial cells and neutrophils", Immunology, 2003, vol. 109, No. 4, pp. 557-563.

Mauriello, C.T. et al., "A novel peptide inhibitor of classical and lectin complement activation including ABO incompatibility". Molecular Immunology. 2013, 53(1-2):132-139.

Mayadas et al., "Mechaisms of immune complex-mediated neutrophil recruitment and tissue injury", Circulation, 2009, vol. 120, No. 20, pp. 2012-2024.

Orbai et al., "Anti-C1q antibodies in systemic lupus erythematosus", Lupus, 2015, vol. 24, No. 1, pp. 42-49.

Sharp et al., "Peptide Inhibitor of Complement C1 (PIC1) Rapidly Inhibits Complement Activation after Intravascular Injection in Rats". PLoS ONE. 2015, vol. 10, No. 7:e0132446.

Stell et al., "Platelet-activating factor: the effector of protein-rich plasma extravasation and nitric oxide synthase induction in rat immune complex peritonitis", British Journal of Pharmacology, 1995, vol. 114, No. 4, pp. 895-901.

Thanel, S., et al., "Anti-C1q autoantibodies from systemic lupus erythematosus patients activate the complement system via both the classical and lectin pathways". Clinical Immunology. 2015, 160(2):180-187.

Tralau, T. et al., "Human leukocyte elastase and cathepsin G are specific inhibitors of C5a-dependent neutrophil enzyme release and chemotaxis". Experimental Dermatology. 2004, 13(5):316-325.

Zawrotniak et al., "Neutrophil extracellular traps (NETs)—formation and implications." Acta Biochimica Polonica. 2013, vol. 60, No. 3, pp. 277-284.

European Search Report issued in European Application No. 17153032 dated Apr. 24, 2017.

Partial European Search Report issued in European Application No. 16815455 dated Jan. 14, 2019.

Supplementary European Search Report issued in European Application No. 16815455 dated Apr. 17, 2019.

International Search Report and Written Opinion issued in International Application No. PCT/US2019/012659 dated Mar. 19, 2019.

Palmer et al., "Hypochlorous Acide Regulates Neutrophil Extracellular Trap Release in Humans", Clinical and Experimental Immunology, Nov. 1, 2011, vol. 167, Issue 2, pp. 261-268.

Hair et al. "Inhibition of Immune Complex Complement Activation and Neutrophil Extracellular Trap Formation by Peptide Inhibitor of Complement C1", Frontiers in Immunology, Mar. 26, 2018 (Mar. 26, 2018), vol. 9, Article 558, pp. 1-12.

Papayannopoulos et al., "Neutrophil Elastase and Myeloperoxidase Regulate the Formation of Neutrophil Extracellular Traps", The Journal of Cell Biology, Oct. 25, 2010, 2010 (Oct. 25, 2010), vol. 191, No. 3, pp. 677-691.

International Search Report and Written Opinion issued in International Application No. PCT/US16/39421 dated Jan. 9, 2017.

Zhang et al., "The Role of natural IgM in myocardial ischemia-reperfusion injury", Journal of Molecular and Cellular Cardiolody, 2006, vol. 41, No. 1, 62-67.

Barbee I. Whitaker PSH, PhD, The 2011 National Blood Collection and Utilization Survey Report; 2011.

Murphy et al., "Transfusing Blood safely and appropriately", BMJ, 2013, vol. 347, pp. 29-33.

Refaal et al., "The transfusion dilemma—weighing the known and newly proposed risks of blood transfusions against the uncertain benefits", Best practice & research Clinical anaesthesiology, 2013, vol. 27, No. 1, pp. 17-35.

Aygun et al., "Clinical significance of RBC alloantibodies and autoantibodies in sickle cell patients who received transfusions", Transfusion, 2002, vol. 42, No. 1, pp. 37-43.

Osterman et al., "Blood product transfusions and reactions", Emergency medicine clinics of North America, 2014, vol. 32, No. 3, pp. 727-738.

Stowell et al., "Initiation and regulation of complement during hemolytic transfusion reactions", Clinical & Developmental Immunology, vol. 2012, Article 307093, 2012, pp. 1-12.

\* cited by examiner

SEQUENCE LISTING

```
<160> NUMBER OF SEQ ID NOS: 45

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Ala Leu Ile Leu Glu Pro Ile Cys Cys Gln Glu Arg Ala Ala
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sarcosine

<400> SEQUENCE: 2

Xaa Ala Leu Ile Leu Glu Pro Ile Cys Cys Gln Glu Arg Ala Ala
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Sarcosine
```

```
<400> SEQUENCE: 3

Ile Xaa Leu Ile Leu Glu Pro Ile Cys Cys Gln Glu Arg Ala Ala
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Sarcosine

<400> SEQUENCE: 4

Ile Ala Xaa Ile Leu Glu Pro Ile Cys Cys Gln Glu Arg Ala Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Sarcosine

<400> SEQUENCE: 5

Ile Ala Leu Xaa Leu Glu Pro Ile Cys Cys Gln Glu Arg Ala Ala
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Sarcosine

<400> SEQUENCE: 6

Ile Ala Leu Ile Xaa Glu Pro Ile Cys Cys Gln Glu Arg Ala Ala
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Sarcosine

<400> SEQUENCE: 7

Ile Ala Leu Ile Leu Xaa Pro Ile Cys Cys Gln Glu Arg Ala Ala
1               5                   10                  15
```

```
<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Sarcosine

<400> SEQUENCE: 8

Ile Ala Leu Ile Leu Glu Xaa Ile Cys Cys Gln Glu Arg Ala Ala
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Sarcosine

<400> SEQUENCE: 9

Ile Ala Leu Ile Leu Glu Pro Xaa Cys Cys Gln Glu Arg Ala Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sarcosine

<400> SEQUENCE: 10

Ile Ala Leu Ile Leu Glu Pro Ile Xaa Cys Gln Glu Arg Ala Ala
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Sarcosine

<400> SEQUENCE: 11

Ile Ala Leu Ile Leu Glu Pro Ile Cys Xaa Gln Glu Arg Ala Ala
1               5                   10                  15

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (10)..(10)
<223> OTHER INFORMATION: Sarcosine

<400> SEQUENCE: 12

Ala Leu Ile Leu Glu Pro Ile Cys Cys Xaa Glu Arg Ala Ala
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Sarcosine

<400> SEQUENCE: 13

Ile Ala Leu Ile Leu Glu Pro Ile Cys Cys Gln Xaa Arg Ala Ala
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Sarcosine

<400> SEQUENCE: 14

Ile Ala Leu Ile Leu Glu Pro Ile Cys Cys Gln Glu Xaa Ala Ala
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Sarcosine

<400> SEQUENCE: 15

Ile Ala Leu Ile Leu Glu Pro Ile Cys Cys Gln Glu Arg Xaa Ala
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Sarcosine

<400> SEQUENCE: 16
```

Ile Ala Leu Ile Leu Glu Pro Ile Cys Cys Gln Glu Arg Ala Xaa
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: N-term dPEG24
<220> FEATURE:
<221> NAME/KEY: MISC_FEATURE
<223> OTHER INFORMATION: C-term dPEG24

<400> SEQUENCE: 17

Ile Ala Leu Ile Leu Glu Pro Ile Cys Cys Gln Glu Arg Ala Ala
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: N-term dPEG24

<400> SEQUENCE: 18

Ile Ala Leu Ile Leu Glu Pro Ile Cys Cys Gln Glu Arg Ala Ala
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term dPEG24

<400> SEQUENCE: 19

Ile Ala Leu Ile Leu Glu Pro Ile Cys Cys Gln Glu Arg Ala Ala
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term dPEG20

<400> SEQUENCE: 20

Ile Ala Leu Ile Leu Glu Pro Ile Cys Cys Gln Glu Arg Ala Ala
1               5                   10                  15

<210> SEQ ID NO 21
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term dPEG16

<400> SEQUENCE: 21

Ile Ala Leu Ile Leu Glu Pro Ile Cys Cys Gln Glu Arg Ala Ala
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term dPEG12

<400> SEQUENCE: 22

Ile Ala Leu Ile Leu Glu Pro Ile Cys Cys Gln Glu Arg Ala Ala
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term dPEG08

<400> SEQUENCE: 23

Ile Ala Leu Ile Leu Glu Pro Ile Cys Cys Gln Glu Arg Ala Ala
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term dPEG06

<400> SEQUENCE: 24

Ile Ala Leu Ile Leu Glu Pro Ile Cys Cys Gln Glu Arg Ala Ala
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term dPEG04

<400> SEQUENCE: 25

Ile Ala Leu Ile Leu Glu Pro Ile Cys Cys Gln Glu Arg Ala Ala
1               5                   10                  15
```

```
<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term dPEG03

<400> SEQUENCE: 26

Ile Ala Leu Ile Leu Glu Pro Ile Cys Cys Gln Glu Arg Ala Ala
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term dPEG02

<400> SEQUENCE: 27

Ile Ala Leu Ile Leu Glu Pro Ile Cys Cys Gln Glu Arg Ala Ala
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sarcosine

<400> SEQUENCE: 28

Ile Ala Leu Ile Leu Glu Pro Ile Xaa Ala Gln Glu Arg Ala Ala
1               5                   10                  15

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sarcosine

<400> SEQUENCE: 29

Ile Ala Leu Ile Leu Glu Pro Ile Xaa Gln Glu Arg Ala Ala
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (7)..(7)
<223> OTHER INFORMATION: Sarcosine
<220> FEATURE:
<221> NAME/KEY: MOD_RES
<222> LOCATION: (9)..(9)
<223> OTHER INFORMATION: Sarcosine

<400> SEQUENCE: 30

Ile Ala Leu Ile Leu Glu Xaa Ile Xaa Cys Gln Glu Arg Ala Ala
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term dPEG24
<220> FEATURE:
<221> NAME/KEY: MOD_RES
<222> LOCATION: (6)..(6)
<223> OTHER INFORMATION: Sarcosine

<400> SEQUENCE: 31

Ile Ala Leu Ile Leu Xaa Pro Ile Cys Cys Gln Glu Arg Ala Ala
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term dPEG24
<220> FEATURE:
<221> NAME/KEY: MOD_RES
<222> LOCATION: (11)..(11)
<223> OTHER INFORMATION: Sarcosine

<400> SEQUENCE: 32

Ile Ala Leu Ile Leu Glu Pro Ile Cys Cys Xaa Glu Arg Ala Ala
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term dPEG24
<220> FEATURE:
<221> NAME/KEY: MOD_RES
<222> LOCATION: (13)..(13)
<223> OTHER INFORMATION: Sarcosine

<400> SEQUENCE: 33

Ile Ala Leu Ile Leu Glu Pro Ile Cys Cys Gln Glu Xaa Ala Ala
1               5                   10                  15

<210> SEQ ID NO 34
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term dPEG24
<220> FEATURE:
<221> NAME/KEY: MOD_RES
<222> LOCATION: (14)..(14)
<223> OTHER INFORMATION: Sarcosine

<400> SEQUENCE: 34

Ile Ala Leu Ile Leu Glu Pro Ile Cys Cys Gln Glu Arg Xaa Ala
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(7)
<223> OTHER INFORMATION: Sarcosine

<400> SEQUENCE: 35

Ile Ala Leu Ile Leu Xaa Xaa Ile Cys Cys Gln Glu Arg Ala Ala
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Sarcosine
<220> FEATURE:
<221> NAME/KEY: MOD_RES
<222> LOCATION: (9)..(9)
<223> OTHER INFORMATION: Sarcosine

<400> SEQUENCE: 36

Ile Ala Leu Ile Leu Xaa Pro Ile Xaa Cys Gln Glu Arg Ala Ala
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Sarcosine
<220> FEATURE:
<221> NAME/KEY: MOD_RES
<222> LOCATION: (11)..(11)
<223> OTHER INFORMATION: Sarcosine

<400> SEQUENCE: 37

Ile Ala Leu Ile Leu Glu Xaa Ile Cys Cys Xaa Glu Arg Ala Ala
```

-continued

```
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sarcosine
<220> FEATURE:
<221> NAME/KEY: MOD_RES
<222> LOCATION: (11)..(11)
<223> OTHER INFORMATION: Sarcosine

<400> SEQUENCE: 38

Ile Ala Leu Ile Leu Glu Pro Ile Xaa Cys Xaa Glu Arg Ala Ala
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Sarcosine
<220> FEATURE:
<221> NAME/KEY: MOD_RES
<222> LOCATION: (13)..(13)
<223> OTHER INFORMATION: Sarcosine

<400> SEQUENCE: 39

Ile Ala Leu Ile Leu Glu Xaa Ile Cys Cys Gln Glu Xaa Ala Ala
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sarcosine
<220> FEATURE:
<221> NAME/KEY: MOD_RES
<222> LOCATION: (13)..(13)
<223> OTHER INFORMATION: Sarcosine

<400> SEQUENCE: 40

Ile Ala Leu Ile Leu Glu Pro Ile Xaa Cys Gln Glu Xaa Ala Ala
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
```

<223> OTHER INFORMATION: Sarcosine
<220> FEATURE:
<221> NAME/KEY: MOD_RES
<222> LOCATION: (14)..(14)
<223> OTHER INFORMATION: Sarcosine

<400> SEQUENCE: 41

Ile Ala Leu Ile Leu Glu Xaa Ile Cys Cys Gln Glu Arg Xaa Ala
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sarcosine
<220> FEATURE:
<221> NAME/KEY: MOD_RES
<222> LOCATION: (14)..(14)
<223> OTHER INFORMATION: Sarcosine

<400> SEQUENCE: 42

Ile Ala Leu Ile Leu Glu Pro Ile Xaa Cys Gln Glu Arg Xaa Ala
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term dPEG24

<400> SEQUENCE: 43

Ile Ala Leu Ile Leu Ala Pro Ile Cys Cys Gln Ala Arg Ala Ala
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Sarcosine

<400> SEQUENCE: 44

Ile Ala Leu Ile Leu Ala Pro Ile Xaa Cys Gln Ala Arg Ala Ala
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)

-continued

```
<223> OTHER INFORMATION: Sarcosine

<400> SEQUENCE: 45

Ile Ala Leu Ile Leu Ala Xaa Ile Cys Cys Gln Ala Arg Ala Ala
1               5                   10                  15
```

PIC1 INHIBITION OF MYELOPEROXIDASE OXIDATIVE ACTIVITY IN AN ANIMAL MODEL

CROSS-REFERENCE TO RELATED APPLICATIONS

This application is a continuation of U.S. application Ser. No. 16/839,464, filed Apr. 3, 2020, which is a continuation of U.S. application Ser. No. 16/242,550, filed Jan. 8, 2019, which claims priority to U.S. Provisional Application No. 62/615,183, filed Jan. 9, 2018, U.S. Provisional Application No. 62/681,458, filed Jun. 6, 2018, and U.S. Provisional Application No. 62/746,649, filed Oct. 17, 2018, the disclosures of each which are herein incorporated by reference in their entirety.

SEQUENCE LISTING

The instant application contains a Sequence Listing which has been submitted electronically in ASCII format and is hereby incorporated by reference in its entirety. Said ASCII copy, created on Mar. 25, 2020, is named Seqlist.txt and is 16,143 bytes in size.

BACKGROUND

NETs are a means by which neutrophils contain infection by turning themselves into webs of DNA decorated with antimicrobial molecules. NETs have been shown to contribute to pathogenesis in a wide range of inflammatory and autoimmune diseases, such as Systemic Lupus Erythematosus (SLE) and transfusion-related acute lung injury (TRALI).

The pathogenesis of SLE is very complex, but two major contributors are immune complex-initiated complement activation and NET formation. Immune complexes that initiate classical pathway complement activation leading to consumption of C4 and C3 have long been appreciated and contribute to Lupus Nephritis [1-3]. NETs, however, are more recently recognized as contributing to SLE pathogenesis [4-6].

TRALI is the leading cause of morbidity and mortality associated with blood transfusion. TRALI is defined as an acute lung injury that occurs within 6 hours of receiving an allogenic blood product transfusion. TRALI is commonly characterized by dyspnea, fever, hypotension, hypoxemia and pulmonary edema with laboratory tests demonstrating transient leukopenia and thrombocytopenia and bilateral infiltrates by chest X-ray. The mortality rate is 5-10% with a majority of patients (70-90%) requiring mechanical ventilation and hemodynamic support. In the absence of efficacious pharmacological intervention, the current standard of care is limited solely to supportive therapy.

The pathophysiology of TRALI is complex. Clinically, antibodies to human leukocyte antigens or human neutrophil alloantigens in donor blood products are believed to cause the majority of TRALI cases. Non-antibody mediated or non-immune TRALI, usually resulting after platelet or erythrocyte transfusion, accounts for 11-39% of cases. A number of animal models have been established to investigate the pathophysiology of both antibody-mediated and non-antibody mediated TRALI. While neutrophils play a key part in the pathogenesis of antibody-mediated TRALI, clinical reports and animal model data suggest that depending on the class of antibodies involved, monocytes, lymphocytes, platelets as well as endothelial cells may contribute to TRALI. Complement activation is also required for the development of TRALI in various antibody-mediated animal models, and contributes to the pathological process in clinical TRALI cases.

Animal models have demonstrated that antibody-mediated activation of host neutrophils induces sequestration in the pulmonary capillaries that leads to tissue injury. These activated neutrophils release neutrophil extracellular traps (NETs) which contribute to TRALI pathogenesis in mouse models. NET biomarkers, e.g., myeloperoxidase (MPO), nucleosomes and DNA, have been detected in serum collected from TRALI patients.

Myeloperoxidase (MPO) is a heme-based peroxidase found in neutrophils. MPO is the major enzyme present in neutrophils, accounting for 30% of the dry weight of the cell. The main function of MPO is to generate hypochlorous acid to help neutrophils kill microbial invaders. However, generation of hypochlorous acid by MPO can also lead to the damage of host tissues and has been shown to directly contribute to parenchymal injury in many inflammatory diseases. For instance, MPO contributes to parenchymal lung damage in cystic fibrosis. In addition to direct antimicrobial activity, MPO has also been shown to act in the important pathway of creating neutrophil extracellular traps (NETs).

BRIEF DESCRIPTION OF THE DRAWINGS

This patent application file contains at least one drawing executed in color. Copies of this patent application with color drawing(s) will be provided by the Office upon request and payment of the necessary fee.

FIG. 1A shows PA-dPEG24 inhibited C5a generation in normal human serum (NHS) stimulated with heat-aggregated IgG (Agg-IgG) immune complexes. The data shown are means of (n=5) independent experiments and the standard error of the mean (SEM). FIG. 1B shows PA-dPEG24 inhibition of iC3b generation in normal human serum (NHS) stimulated with heat-aggregated IgG (Agg-IgG) immune complexes. The data shown are means of (n=4) independent experiments and the standard error of the mean (SEM). FIG. 1C shows PA-dPEG24 inhibition of SC5b-9 generation in normal human serum (NHS) stimulated with heat-aggregated IgG (Agg-IgG) immune complexes. The data shown are means of (n=6) independent experiments and the standard error of the mean (SEM).

FIG. 2A shows PA-dPEG24 inhibition of C5a generation in normal human serum (NHS) stimulated with ovalbumin-antiovalbumin immune complexes. The data shown are means of (n=4) independent experiments and the standard error of the mean (SEM). FIG. 2B shows PA-dPEG24 inhibition of iC3b generation in normal human serum (NHS) stimulated with ovalbumin-antiovalbumin immune complexes. The data shown are means of (n=4) independent experiments and the standard error of the mean (SEM). FIG. 2C shows PA-dPEG24 inhibition of SC5b-9 generation in normal human serum (NHS) stimulated with ovalbumin-antiovalbumin immune complexes. At 2 mM PA-dPEG24 the measured SC5b-9 was at the lower limit of detection. The data shown are means of (n=3) independent experiments and the standard error of the mean (SEM).

FIG. 3A shows PA-dPEG24 inhibition of C5a generation in normal human serum (NHS) stimulated with C1-antiC1q immune complexes. The data shown are means of (n=4) independent experiments and the standard error of the mean (SEM). FIG. 3B shows PA-dPEG24 inhibition of iC3b generation in normal human serum (NHS) stimulated with C1-antiC1q immune complexes. The data shown are means of (n=4) independent experiments±SEM. FIG. 3C shows PA-dPEG24 inhibition of SC5b-9 generation in normal human serum (NHS) stimulated with C1-antiC1q immune complexes. The data shown are means of (n=4) independent experiments and the standard error of the mean (SEM).

FIG. 7A shows NET formation induced by PMNs incubated alone (untreated), with normal human sera (NHS), immune complexes alone (IC) or immune complex-activated sera (ICsera). FIG. 7B shows PA-dPEG24 inhibition of NET generation by human neutrophils stimulated with immune complex-activated sera (ICsera) assayed by PicoGreen. The data shown are means of (n=4) independent experiments and the standard error of the mean (SEM). In FIG. 7C, the first row shows unstimulated neutrophils, the second row shows neutrophils stimulated with immune complex-activated human sera (ICsera) and hydrogen peroxide ($H_2O_2$) and the third row shows neutrophils stimulated with ICsera+$H_2O_2$ in the presence of PA-dPEG24 (PIC1). The first column shows slides probed with DAPI to visualize DNA and the second column shows slides probed with anti-MPO antibody.

In FIG. 8A, free hemoglobin present in rat plasma collected before transfusion (0) or 0.5, 5, 20, 60, 120 or 360 min after 15 (♦, n=3), 30 (▲, n=3) or 45% (■, n=3) transfusion of human RBCs was measured by spectrophotometry. One group of sham animals (●, n=3) was analyzed as well. In FIG. 8B, the percent of surviving human RBCs from 15 (●, n=3), 30 (■, n=3) or 45% (▲, n=3) transfusion of human RBCs were detected using FITC-conjugated anti-human CD235a (glycophorin A) monoclonal antibody at 0.5, 5, 20 60, 120 and 360 min after transfusion as measured by flow cytometry. Clearance kinetics were standardized to injected RBCs at baseline (0 min). The data shown are means and standard error of the mean (SEM).

FIG. 11A shows gross lung weights measured for sham animals (n=7), animals treated prophylactically with vehicle (n=5) or PIC1 (n=8). The data shown are means and standard error of the mean (SEM). Representative histology (hematoxylin and eosin) stains are shown of lungs from sham rats (FIG. 11B), rats receiving vehicle (FIG. 11C) and rats receiving PIC1 (FIG. 11D). Animals receiving PIC1 demonstrated the normal lung architecture as seen in sham treated animals, while animals receiving vehicle showed consolidation of the alveolar spaces and thickening of the alveolar cell walls. The bar represents 100 µm. Tissues were observed with a microscope (BX50, Olympus) at a magnification of 20× at room temperature. Images were acquired with a digital camera (DP70, Olympus).

In FIG. 12A, blinded grading of H&E sections for neutrophil infiltration and cell wall thickening form animals receiving vehicle (n=7) and animals receiving PIC1 (n=9) were scored on a scale of 0-4: 0=normal lungs, 1=minor lung involvement, 2=moderate lung involvement, 3=serious lung involvement, 4=severe lung involvement. The box shows quartiles, the whiskers are 25th percentile, and the solid line is the mean. In FIG. 12B, MPO was isolated from homogenized lung tissue by antibody capture to measure MPO activity. Samples were combined with hydrogen peroxide and ADHP solution and immediately read at an excitation wavelength of 535 nm and emission wavelength of 590 nm in a microplate reader from 0 to 10 minutes every 25 seconds. MPO (positive control, +CTR, n=3) and PBS (negative control, −CTR, n=3) were analyzed along with samples from animals receiving vehicle (n=2) and animals receiving PIC1 (n=3). Each sample was evaluated in triplicate. The data shown are means and the standard deviation of the mean. For simplicity, only the 5- and 10-minute time points are shown.

FIG. 21 shows peritoneal wash supernatant oxidation of TMB (n=4). FIG. 22 shows peritoneal wash supernatant free DNA measured via PicoGreen assay (n=4). FIG. 23 shows blood plasma free DNA measured via PicoGreen assay (n=4). In FIGS. 21-23, the data shown are means of independent animals±SEM.

SUMMARY OF THE INVENTION

Figure 1A:
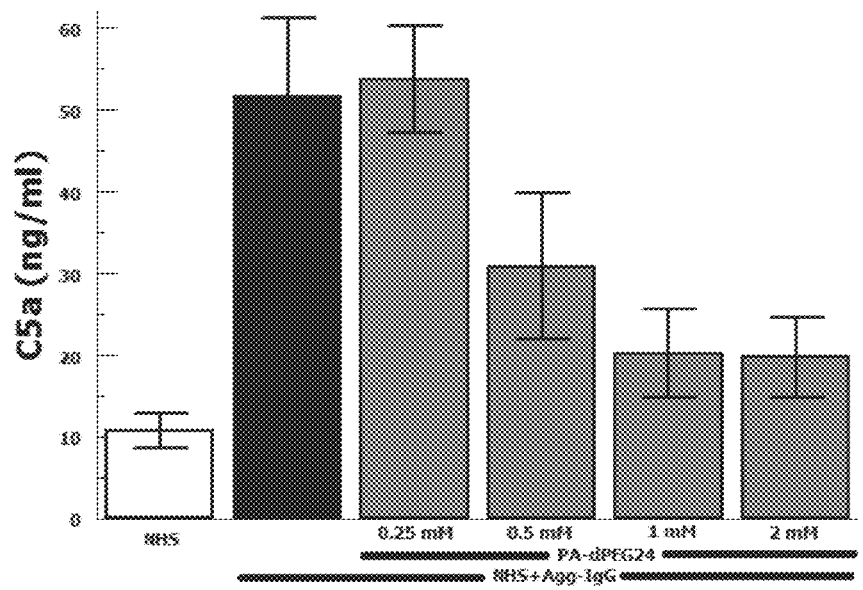
FIGS. 1A-1C are graphs showing PA-dPEG24 inhibition of heat-aggregated IgG immune complex-initiated complement activation assayed by complement effectors.

In one aspect is provided a method of treating systemic lupus erythematosus (SLE) in a subject. The method comprises administering a therapeutically effective amount of PIC1 to the subject.

In some embodiments, the method is effective to modulate immune complex activation of the complement system and NET formation in the subject. In some embodiments, the NET formation is stimulated by at least one of a bacterium, a fungus, a parasite or a virus. In some embodiments, the method is effective to inhibit NET-mediated inflammatory tissue damage in the subject.

In another aspect is provided a method of treating transfusion-related acute lung injury (TRALI) in a subject. The method comprises administering a therapeutically effective amount of PIC1 to the subject.

In some embodiments, the method is effective to modulate immune complex activation of the complement system and NET formation in the subject. In some embodiments, the NET formation is stimulated by at least one of a bacterium, a fungus, a parasite or a virus. In some embodiments, the method is effective to inhibit NET-mediated inflammatory tissue damage in the subject. In some embodiments, the PIC1 is administered before the subject is administered a blood transfusion, after the subject is administered the blood transfusion, and/or during the blood transfusion.

In various embodiments of the above aspects, the PIC1 inhibits myeloperoxidase (MPO) activity in the subject. In various embodiments, the PIC1 is administered parenterally. In various embodiments, the subject is human. In certain embodiments, the PIC1 is a peptide comprising one or more PEG moieties. In certain embodiments, the PIC1 is PA-dPEG24. In certain embodiments, the PA-dPEG24 comprises the sequence of IALILEPICCQERAA-dPEG24 (SEQ ID NO: 19).

DETAILED DESCRIPTION OF THE INVENTION

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below.

The term "inhibition" refers to the reduction in the biological function of an enzyme, protein, peptide, factor, byproduct, or derivative thereof either individually or in complexes; reduction in the quantity of a biological protein, peptide, or derivative thereof whether in vivo or in vitro; or interruption of a biological chain of events, cascade, or pathway known to comprise a related series of biological or chemical reactions. The term "inhibition" may thus be used, for example, to describe the reduction of quantity of a single component of the complement cascade compared to a control sample, a reduction in the rate or total amount of formation of a component or complex of components, or the reduction of the overall activity of a complex process or series of biological reactions leading to such outcomes as cell lysis, formation of convertase enzymes, formation of complement-derived membrane attack complexes, inflammation, or inflammatory disease. In an in vitro assay, the term "inhibition" may refer to the measurable reduction of some biological or chemical event, but the person of ordinary skill in the art will appreciate that the measurable reduction need not be total to be "inhibitory."

The term "PIC1" refers to a peptide comprising the polar assortant (PA) sequence of IALILEPICCQERAA (SEQ ID NO: 1), as well as peptides comprising the same amino acid sequence but with modifications such as PEGylation. The term "PIC1 variant" refers to peptides comprising a sequence that is at least 85% identical, or at least 90% identical, or at least 95% identical, or at least 99% identical, but not 100% identical, to the PA sequence of IALILE-PICCQERAA (SEQ ID NO: 1). PIC1 variants may comprise peptides with at least one of the amino acids of the PA sequence deleted. PIC1 variants may comprise peptides with an amino acid inserted into the PA sequence. PIC1 variants may comprise peptides with at least one of the amino acids of the PA sequence substituted with another amino acid, such as alanine, a modified amino acid or an amino acid derivative, such as sarcosine (Sar).

The term "subject" as used herein means any subject for whom diagnosis, prognosis, or therapy is desired. For example, a subject can be a mammal, e.g., a human or non-human primate (such as an ape, monkey, orangutan, or chimpanzee), a dog, cat, guinea pig, rabbit, rat, mouse, horse, cattle, or cow.

The term "therapeutically effective amount" as used herein refers to the total amount of each active component that is sufficient to show a meaningful patient benefit. The therapeutically effective amount of the peptide compound varies depending on several factors, such as the condition being treated, the severity of the condition, the time of administration, the route of administration, the rate of excretion of the compound employed, the duration of treatment, the co-therapy involved, and the age, gender, weight, and condition of the subject, etc. One of ordinary skill in the art can determine the therapeutically effective amount. Accordingly, one of ordinary skill in the art may need to titer the dosage and modify the route of administration to obtain the maximal therapeutic effect.

As used herein, "treat," "treating," or "treatment" refers to administering a therapy in an amount, manner (e.g., schedule of administration), and/or mode (e.g., route of administration), effective to improve a disorder (e.g., a disorder described herein) or a symptom thereof, or to prevent or slow the progression of a disorder (e.g., a disorder described herein) or a symptom thereof. This can be evidenced by, e.g., an improvement in a parameter associated with a disorder or a symptom thereof, e.g., to a statistically significant degree or to a degree detectable to one skilled in the art. An effective amount, manner, or mode can vary depending on the subject and may be tailored to the subject. By preventing or slowing progression of a disorder or a symptom thereof, a treatment can prevent or slow deterioration resulting from a disorder or a symptom thereof in an affected or diagnosed subject.

In one aspect is provided a method of inhibiting inflammation in a subject comprising administering a therapeutically effective amount of PIC1, or a PIC1 variant, to the subject. In another aspect is provided a method of treating an inflammatory disorder in a subject comprising administering a therapeutically effective amount of PIC1, or a PIC1 variant, to the subject.

Examples of PIC1 and PIC1 variants include, but are not limited to, the peptides listed in Table 1.

TABLE 1

| Peptide name | Peptide sequence |
| --- | --- |
| PA | IALILEPICCQERAA (SEQ ID NO: 1) |
| PA-I1Sar | (Sar)ALILEPICCQERAA (SEQ ID NO: 2) |
| PA-A2Sar | I(Sar)LILEPICCQERAA (SEQ ID NO: 3) |
| PA-L3Sar | IA(Sar)ILEPICCQERAA (SEQ ID NO: 4) |
| PA-I4Sar | IAL(Sar)LEPICCQERAA (SEQ ID NO: 5) |
| PA-L5Sar | IALI(Sar)EPICCQERAA (SEQ ID NO: 6) |
| PA-E6Sar | IALIL(Sar)PICCQERAA (SEQ ID NO: 7) |
| PA-P7Sar | IALILE(Sar)ICCQERAA (SEQ ID NO: 8) |
| PA-I8 Sar | IALILEP(Sar)CCQERAA (SEQ ID NO: 9) |
| PA-C9Sar | IALILEPI(Sar)CQERAA (SEQ ID NO: 10) |
| PA-C10Sar | IALILEPIC(Sar)QERAA (SEQ ID NO: 11) |
| PA-Q11Sar | ALILEPICC(Sar)ERAA (SEQ ID NO: 12) |
| PA-E12Sar | IALILEPICCQ(Sar)RAA (SEQ ID NO: 13) |
| PA-R13Sar | IALILEPICCQE(Sar)AA (SEQ ID NO: 14) |
| PA-A14Sar | IALILEPICCQER(Sar)A (SEQ ID NO: 15) |
| PA-A15Sar | IALILEPICCQERA(Sar) (SEQ ID NO: 16) |
| dPEG24-PA-dPEG24 | dPEG24-IALILEPICCQERAA-dPEG24 (SEQ ID NO: 17) |
| dPEG24-PA | dPEG24-IALILEPICCQERAA (SEQ ID NO: 18) |
| PA-dPEG24 | IALILEPICCQERAA-dPEG24 (SEQ ID NO: 19) |
| PA-dPEG20 | IALILEPICCQERAA-dPEG20 (SEQ ID NO: 20) |
| PA-dPEG16 | IALILEPICCQERAA-dPEG16 (SEQ ID NO: 21) |
| PA-dPEG12 | IALILEPICCQERAA-dPEG12 (SEQ ID NO: 22) |
| PA-dPEG08 | IALILEPICCQERAA-dPEG08 (SEQ ID NO: 23) |
| PA-dPEG06 | IALILEPICCQERAA-dPEG06 (SEQ ID NO: 24) |
| PA-dPEG04 | IALILEPICCQERAA-dPEG04 (SEQ ID NO: 25) |
| PA-dPEG03 | IALILEPICCQERAA-dPEG03 (SEQ ID NO: 26) |
| PA-dPEG02 | IALILEPICCQERAA-dPEG02 (SEQ ID NO: 27) |
| PA-C9SarC10A | IALILEPI(Sar)AQERAA (SEQ ID NO: 28) |
| PA-C9SarD10 | IALILEPI(Sar)QERAA (SEQ ID NO: 29) |
| PA-P7SarC9Sar | IALILE(Sar)I(Sar)CQERAA (SEQ ID NO: 30) |
| PA-E6Sar-dPEG24 | IALIL(Sar)PICCQERAA-dPEG24 (SEQ ID NO: 31) |
| PA-Q11Sar-dPEG24 | IALILEPICC(Sar)ERAA-dPEG24 (SEQ ID NO: 32) |
| PA-R13Sar-dPEG24 | IALILEPICCQE(Sar)AA-dPEG24 (SEQ ID NO: 33) |
| PA-A14Sar-dPEG24 | IALILEPICCQER(Sar)A-dPEG24 (SEQ ID NO: 34) |
| E6SarP7Sar | IALIL(Sar)(Sar)ICCQERAA (SEQ ID NO: 35) |
| E6SarC9Sar | IALIL(Sar)PI(Sar)CQERAA (SEQ ID NO: 36) |
| Q11SarP7Sar | IALILE(Sar)ICC(Sar)ERAA (SEQ ID NO: 37) |
| Q11SarC9Sar | IALILEPI(Sar)C(Sar)ERAA (SEQ ID NO: 38) |

TABLE 1-continued

| Peptide name | Peptide sequence |
| --- | --- |
| R13SarP7Sar | IALILE(Sar)ICCQE(Sar)AA (SEQ ID NO: 39) |
| R13SarC9Sar | IALILEPI(Sar)CQE(Sar)AA (SEQ ID NO: 40) |
| A14SarP7Sar | IALILE(Sar)ICCQER(Sar)A (SEQ ID NO: 41) |
| A14SarC9Sar | IALILEPI(Sar)CQER(Sar)A (SEQ ID NO: 42) |
| E6AE12A-dPEG24 | IALILAPICCQARAA-dPEG24 (SEQ ID NO: 43) |
| E6AE12AC9Sar | IALILAPI(Sar)CQARAA (SEQ ID NO: 44) |
| E6AE12AP7Sar | IALILA(Sar)ICCQARAA (SEQ ID NO: 45) |

In some embodiments, PIC1 comprises one or more PEG moieties. The PEG moieties may be attached to the N-terminus, the C-terminus, or both the N-terminus and C-terminus by PEGylation. In one or more embodiments, 24 PEG moieties are attached to the N-terminus. In one or more embodiments, 24 PEG moieties are attached to the C-terminus. In one or more embodiments, 24 PEG moieties are attached to the N-terminus and to the C-terminus. In one or more embodiments, 1, 2, 3, 4, 5, 6, 7, 8, 9, 10, 11, 12, 13, 14, 15, 16, 17, 18, 19, 20, 21, 22, 23, or 24 PEG moieties are attached to the N-terminus. In one or more embodiments, 1, 2, 3, 4, 5, 6, 7, 8, 9, 10, 11, 12, 13, 14, 15, 16, 17, 18, 19, 20, 21, 22, 23, or 24 PEG moieties are attached to the C-terminus. In one or more embodiments, 1, 2, 3, 4, 5, 6, 7, 8, 9, 10, 11, 12, 13, 14, 15, 16, 17, 18, 19, 20, 21, 22, 23, or 24 PEG moieties are attached to both the N-terminus and the C-terminus.

The PIC1 peptide may be a synthetic peptide. A synthetic peptide is prepared in vitro. Synthetic peptides can be prepared according to various methods known in the art. For example, a synthetic peptide can be prepared by sequentially coupling individual amino acids to form the peptide. In some embodiments, the carboxyl group of individual amino acids is sequentially coupled to the amino terminus of a growing peptide chain. Protecting groups can be used to prevent unwanted side reactions from occurring during the coupling process. Peptide synthesis can occur in liquid phase or in solid phase.

Exemplary PIC1 peptides include, but are not limited to, PA-dPEG24 (a peptide comprising the polar assortant (PA) sequence and 24 PEG moieties at the C-terminus), PA-dPEG20 (comprising 20 PEG moieties at the C-terminus), PA-dPEG16 (comprising 16 PEG moieties at the C-terminus), PA-dPEG12 (comprising 12 PEG moieties at the C-terminus), PA-dPEG08 (comprising 8 PEG moieties at the C-terminus), PA-dPEG06 (comprising 6 PEG moieties at the C-terminus), PA-dPEG04 (comprising 4 PEG moieties at the C-terminus), PA-dPEG03 (comprising 3 PEG moieties at the C-terminus), and PA-dPEG02 (comprising 2 PEG moieties at the C-terminus).

PIC1 peptides can inhibit the classical pathway of complement by binding and blocking activation of the initiating component of the cascade, C1 [19, 20]. PA-dPEG24 is a 15-amino acid PEGylated peptide in the PIC1 family. PA-dPEG24 can inhibit immune complex-initiated complement activation as well as inhibit NET formation. PA-dPEG24 can consistently inhibit complement activation by a variety of immune complexes and can also inhibit NET formation initiated by several stimuli.

In some embodiments, PIC1 is effective to inhibit NETosis in the subject. In some embodiments, the administered PIC1 inhibits MPO activity in the subject. In various embodiments, the subject is human. NETosis is a process by which neutrophils undergo cell death by releasing their chromosomal DNA as neutrophil extracellular traps (NET). A NET is web-shaped and is comprised of chromatin fibrils and antimicrobial molecules. In some embodiments, NETosis is stimulated by at least one of a bacterium, a fungus, a parasite or a virus.

Figure 16:
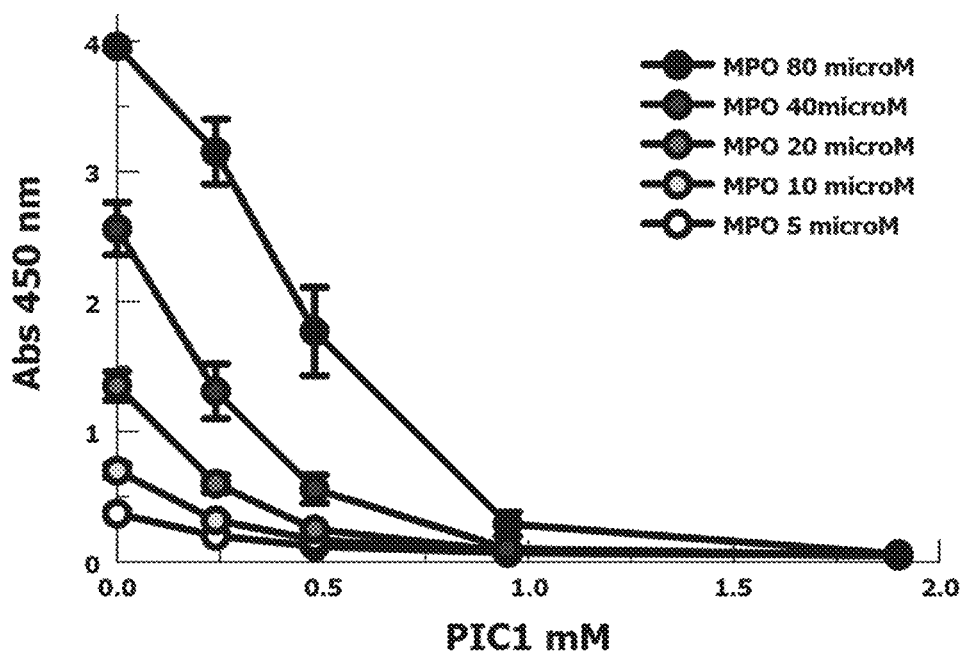
FIG. 16 is a graph showing PIC1 dose-response inhibition of MPO-mediated oxidation of TMB for increasing concentrations of MPO.

PIC1 inhibits MPO-mediated oxidation, as shown in FIG. 16. PA-dPEG24 can inhibit the peroxidase effect of MPO in clinical CF sputum samples ex vivo as well as for purified MPO in vitro. PA-dPEG24 also inhibits the peroxidase activity of other heme-based peroxidases including hemoglobin and myoglobin in vitro. PA-dPEG24 can inhibit NET formation in vitro, such as NET formation stimulated by any of phorbol 12-myristate 13-acetate (PMA), purified MPO, and immune complex-activated human sera.

PIC1 peptides can be administered to the subject to modulate immune complex activation of the complement system and NET formation in a disease. Exemplary diseases include, but are not limited to, Lupus Nephritis, Serum Sickness, Delayed Type Hypersensitivity (Type III Hypersensitivity) Reactions, Infective Endocarditis, Auto-immune Glomerulonephritis, Cryoglobulinemia, Sjogren's syndrome, Small Vessel Vasculitis, ANCA-associated Vasculitis, Scleroderma and other inflammatory or autoimmune vasculitis diseases including glomerulonephropathies, acute respiratory distress syndrome, acute lung injury, transfusion related acute lung injury, cystic fibrosis, chronic obstructive pulmonary disease (COPD), rheumatoid arthritis, atherosclerosis, Alzheimer's disease, psoriasis, Type 1 Diabetes Mellitus, Type 2 Diabetes Mellitus, antiphospholipid antibody syndrome, gout, Crohn's disease, ulcerative colitis, rhabdomyolysis, Obesity/Metabolic Syndrome, Wegener's granulomatosis (WG), thrombosis, systemic inflammatory response syndrome (SIRS), sepsis, retinopathy of prematurity (ROP), pre-eclampsia, periodontitis, neonatal chronic lung disease (CLD), necrotizing enterocolitis (NEC), influenza-induced pneumonitis, inflammatory lung disease (ILD), inflammatory bowel disease (IBD), inflammation in cancer, or bronchopulmonary dysplasia (BPD).

In certain embodiments, PIC1 (e.g., PA-dPEG24) substantially inhibits NET formation and/or NETosis. In other embodiments, PIC1 (e.g., PA-dPEG24) inhibits or substantially inhibits NET-mediated inflammatory tissue damage.

In another aspect is provided a method of treating systemic lupus erythematosus (SLE) in a subject comprising administering a therapeutically effective amount of PIC1 to the subject.

Two major aspects of SLE pathogenesis that may be targeted therapeutically are immune complex-initiated complement activation and neutrophil extracellular trap (NET) formation by neutrophils. Without wishing to be bound by theory, the role of anti-C1q antibodies in the blood of SLE patients is an active area of investigation with considerable data accumulating to demonstrate a strong association between the presence of anti-C1 q antibodies and Lupus Nephritis [7, 8]. Investigators have also shown that anti-C1q antibodies from SLE patients bound to a surface in an ELISA-type assay can activate the classical and lectin pathways [9]. Thus, anti-C1q antibodies may play a role in pathogenesis and in formation of SLE-like immune complexes.

Immune complexes can activate complement generating effectors of complement activation (e.g., C5a, sublytic concentrations of membrane attack complex, etc.) that interact with and can stimulate human neutrophils [10-13]. However, articles describing that immune complexes can induce neutrophils to generate NETs have focused on the role of Fc receptors in this process [14-17]. If the articles show a link between immune complexes and NETs, the contribution of complement activation in this process remains unclear. Akong-Moore et al. [18] suggested that a major pathway of NET formation can occur via MPO and its primary function of generating hypochlorous acid from hydrogen peroxide and chloride ion. NET formation may be blocked by utilizing an MPO inhibitor.

In some embodiments, PIC1 is effective to inhibit NETosis in the subject. In some embodiments, NETosis is stimulated by at least one of a bacterium, a fungus, a parasite or a virus. PIC1 can be administered to modulate immune complex complement activation and NET formation. In one embodiment, the PIC1 is PA-dPEG24. In one embodiment, PIC1 can be used to modulate C1-antiC1q immune complexes. In one embodiment, PIC1 can be used to inhibit immune complex activation and NET formation. In certain embodiments, PIC1 can be used to limit the generation of pro-inflammatory complement effectors. In one embodiment, PIC1 can be used to limit the generation of C5a and sC5b-9. In certain embodiments, PIC1 inhibits NET formation by human neutrophils stimulated by PMA.

In some embodiments, the administered PIC1 inhibits MPO activity in the subject. PIC1 can be used to inhibit NET formation by human neutrophils stimulated by MPO. In accordance with certain aspects, PIC1 can be used to inhibit NET formation by human neutrophils stimulated by immune complex activated sera. In accordance with certain aspects, PIC1 is delivered parenterally. In various embodiments, the subject is human.

In accordance with certain aspects, PIC1 can be used to modulate immune complex complement activation and neutrophil formation to treat SLE, Lupus Nephritis, Serum Sickness, Delayed Type Hypersensitivity (Type III Hypersensitivity) Reactions, Infective Endocarditis, Auto-immune Glomerulonephritis, Cryoglobulinemia, Sjogren's syndrome, Small Vessel Vasculitis, ANCA-associated Vasculitis, Scleroderma and other inflammatory or autoimmune vasculitis diseases, Glomerulonephropathies, Acute Respiratory Distress Syndrome, Acute Lung Injury, Transfusion Related Acute Lung Injury, Cystic Fibrosis, Chronic Obstructive Pulmonary Disease, Rheumatoid Arthritis, Atherosclerosis, Alzheimer's Disease, Psoriasis, Type 1 Diabetes Mellitus, Type 2 Diabetes Mellitus, Antiphospholipid Antibody Syndrome, Gout, Crohn's Disease, Ulcerative Colitis, Rhabodmyolysis, and Obesity/Metabolic Syndrome.

The experiments of Example 1 demonstrate that PA-dPEG24 can inhibit immune complex-initiated complement activation and the generation of pro-inflammatory complement effectors. This suggests that complement inhibitory peptides could moderate aspects of pathogenesis in diseases where immune complex activation of the complement system plays a vital role, such as SLE, Lupus Nephritis, Serum Sickness, Delayed Type Hypersensitivity (Type III Hypersensitivity) Reactions, Infective Endocarditis, Auto-immune Glomerulonephritis, Cryoglobulinemia, Sjogren's syndrome, Small Vessel Vasculitis, ANCA-associated Vasculitis, Scleroderma and other inflammatory or autoimmune vasculitis diseases, Glomerulonephropathies, Acute Respiratory Distress Syndrome, Acute Lung Injury, Transfusion Related Acute Lung Injury, Cystic Fibrosis, Chronic Obstructive Pulmonary Disease, Rheumatoid Arthritis, Atherosclerosis, Alzheimer's Disease, Psoriasis, Type 1 Diabetes Mellitus, Type 2 Diabetes Mellitus, Antiphospholipid Antibody Syndrome, Gout, Crohn's Disease, Ulcerative Colitis, Rhabodmyolysis, and Obesity/Metabolic Syndrome. Additionally, C1 and anti-C1q antibodies can be utilized in a novel immune complex to model a type of immune complex that could be predicted to be formed in the plasma of SLE patients with anti-C1q antibodies. PA-dPEG24 also blocked complement activation by C1-antiC1q immune complexes, consistent with the other immune complex types tested.

Immune complex-initiated complement-activated human sera can initiate NET formation, e.g., as demonstrated in Example 1. The result is surprising and stands in contrast to prior observations that immune complexes by themselves can initiate NET formation via Fc receptors [14-17]. Under the experimental conditions of Example 1 the contribution of immune complex-initiated complement activation to NET formation was much greater than that of immune complexes alone. Without wishing to be bound by theory, immune complex-initiated complement activation may be an important mechanism of NET formation in SLE given the presence of immune complexes in active SLE disease.

The experiments in Example 1 also show that PA-dPEG24 can inhibit NET formation by human neutrophils initiated by PMA, MPO or immune complex-initiated complement-activated human sera. Without wishing to be bound by theory, PA-dPEG24 blocks NET formation by inhibiting the MPO-mediated pathway based at least on an ability of PMA to stimulate NET formation via an MPO-mediated pathway [18] and the results described herein utilizing purified MPO. The ability of PA-dPEG24 to inhibit NET formation after immune complex activation of human sera has occurred suggests that NET formation may occur by blocking the MPO-mediated pathway. PA-dPEG24 peptide can block both classical pathway complement activation and inhibit NETosis. PA-dPEG24 and other PIC1 proteins could be useful in methods of treating SLE by acting upon two currently untargeted aspects of SLE pathogenesis.

In another aspect is provided a method of treating transfusion-related acute lung injury (TRALI) in a subject comprising administering a therapeutically effective amount of PIC1 to the subject.

Transfusion-related acute lung injury (TRALI) is a disease of respiratory distress initiated by blood transfusion and the leading cause of transfusion-related death. Described herein is a novel 'two-hit' rat model of TRALI utilizing mismatched erythrocytes that cause neutrophil infiltration of lung parenchyma. The two-hit rat model allows for assessing the role of peptide inhibitor of complement C1 (PIC1) in attenuating lung injury in this new TRALI model.

Described herein is a novel model of TRALI, with data showing the ability of PIC1 to attenuate TRALI-mediated disease in this model. A number of 'two-hit' models, utilizing LPS as the 'first-hit' and either an antibody-dependent (e.g. $H2K^d$, HLA, etc.) or an antibody-independent (e.g. aged RBCs, lysoPCs, RBC supernatants, etc.) stimulus as the 'second hit' have been published in the literature in a variety of species. The model described herein is unique in that it uses antibody-initiated complement-mediated hemolysis of transfused erythrocytes as the 'second hit', in contrast to transfusion of RBCs using syngeneic erythrocytes. Wistar rats possessing preexisting antibodies to the A antigen of human RBCs can initiate classical complement activation that can lead to a vigorous intravascular hemolysis after transfusion of type A or type AB human erythrocytes.

PIC1 is a multifunctional molecule. In an AIHTR model, PIC1 can inhibit hemolysis of transfused mismatched RBCs by suppressing classical complement pathway activation and RBC lysis by the membrane attack complex (MAC). PIC1 can act as an antioxidant molecule in vitro to inhibit peroxidase activity of free heme, hemoglobin and myoglobin as well as the peroxidase activity of MPO.

In some embodiments, the PIC1 is administered before the subject is administered a blood transfusion, after the subject is administered the blood transfusion, and/or during the blood transfusion.

In some embodiments, PIC1 is effective to inhibit NETosis in the subject. In various embodiments, the subject is human. In some embodiments, NETosis is stimulated by at least one of a bacterium, a fungus, a parasite or a virus.

Figure 15:
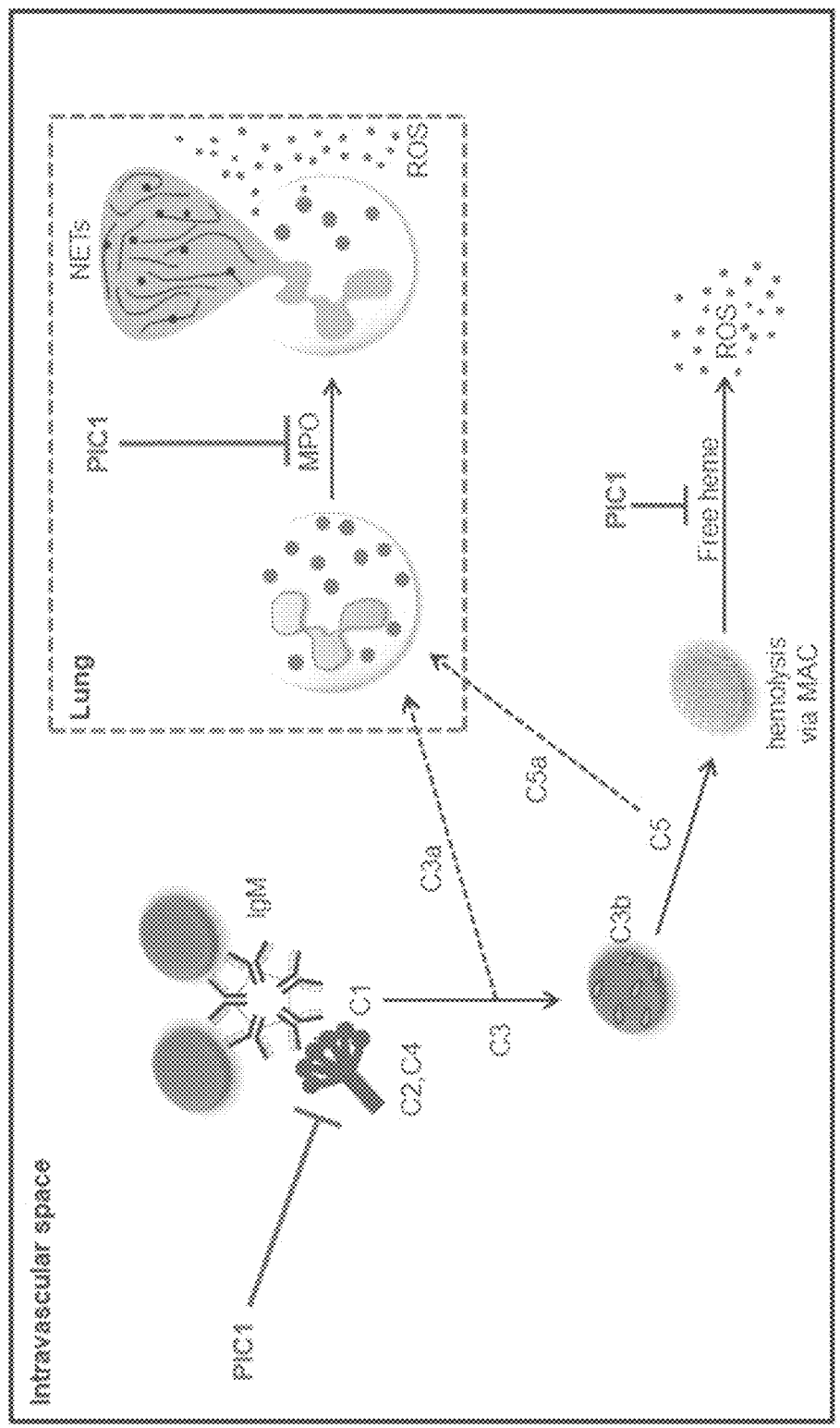
FIG. 15 illustrates a model of PIC1 inhibition of TRALI. In this animal model, the first hit of LPS followed by 30% human RBC transfusion results in a TRALI-like phenotype consisting of lung damage mediated by neutrophil sequestration and activation leading to MPO-mediated reactive oxygen species (ROS) generation and NETosis. Free heme from the complement-mediated hemolysis also contributes to ROS formation. PIC1 can inhibit complement-mediated hemolysis, C3a and C5a generation, ROS formation as well as MPO-mediated NETosis and ROS formation thus inhibiting TRALI. The complement anaphylatoxins C3a and C5a are show as stippled arrows as their direct role in neutrophil activation in this model is unknown.

In some embodiments, the administered PIC1 inhibits MPO activity in the subject. Furthermore, PIC1 can inhibit NETosis mediated by MPO. Without wishing to be bound by theory, PIC1 may reduce the massive infiltration of neutrophils into the lung tissue and may attenuate TRALI by inhibiting complement activation and preventing the generation of the anaphalotoxins C3a and C5a as well as hemoglobinemia through MAC-mediated hemolysis (FIG. 15). PIC1 can attenuate peroxidase-generated ROS activity from free hemoglobin and MPO as well as NETosis in vitro.

Currently there are no pharmacological interventions to treat TRALI with current standard of care consisting of mechanical ventilation and hemodynamic support. The animal model described herein may model a trauma-like clinical scenario in which the patient requires massive transfusion of packed RBCs that leads to TRALI. The ability of PIC1 to block TRALI-like pathogenesis from LPS infusion followed by mismatched RBCs by inhibiting classical pathway complement activation, MPO-mediated ROS formation as well as NETosis suggests that PIC1 may have potential as a pharmacological agent to mitigate multiple aspects of TRALI pathogenesis.

Intranasal administration of DNase reduced symptoms of TRALI in animal models, suggesting that inhibition of NET formation could be a useful therapeutic strategy. A major pathway of NET formation can be mediated by neutrophil-generated MPO through its primary role in producing hypochlorous acid from chloride ion and hydrogen peroxide as well as MPO-derived reactive oxygen species. Phorbol 12-mystate 13-acetate (PMA)-stimulated NET formation can be inhibited by the MPO inhibitor ABAH in vitro revealing another potential mechanism by which to inhibit NET formation.

In a rat model of acute intravascular hemolytic transfusion reaction (AIHTR) utilizing transfusion of mismatched erythrocytes, the rat species has preexisting antibodies to the A antigen of human erythrocytes, resulting in a robust AITHR after transfusion of human erythrocytes from a type A or type AB donor. This AIHTR model may cause antibody-initiated classical complement pathway activation producing acute kidney injury and a highly inflammatory systemic response. The pathogenic aspects of antibody-initiated complement activation and mobilization of neutrophils suggests that this model can adapted to yield a TRALI phenotype, if the inflammatory response were directed towards the lungs.

Antibody-mediated activation of the complement system is directed by the classical complement pathway in which the initiating complex, C1, is bound by IgM or multiple IgG triggering activation and downstream effector functions (i.e., C3a, C5a and membrane attack complex formation). PIC1 peptide inhibitors of the classical complement pathway can bind C1q, the recognition molecule of the C1 complex, to prevent antibody-mediated activation. The PIC1 derivative PA-dPEG24 (IALILEPICCQERAA-dPEG24 (SEQ ID NO: 19)) has been demonstrated to inhibit classical pathway activation both in vitro and in vivo when administered intravascularly into rats where it can achieve >90% systemic inhibition of complement activation by 30 seconds. While PIC1 derivatives have been previously shown to inhibit classical complement pathway-mediated ABO-mismatched hemolysis in vitro, PIC1 can inhibit antibody-initiated complement-mediated hemolysis in a rat model of AIHTR when administered either immediately before or after transfusion of the mismatched erythrocytes. Additionally, PIC1 has also been shown to inhibit the peroxidase activity of MPO and NETosis in vitro. A unique, mismatched erythrocyte-based, 'two-hit' TRALI model has been developed and demonstrated that prophylactic administration of PIC1 mitigates acute lung injury and other hallmarks of this respiratory syndrome.

EXAMPLES

The present invention is also described and demonstrated by way of the following examples. However, the use of this and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1

This example describes testing of Peptide Inhibitor of Complement C1 (PIC1) in in vitro assays of immune complex-mediated complement activation in human sera and assays for NET formation by human neutrophils.

Blood from healthy donors was obtained. PA-dPEG24 (IALILEPICCQERAA-dPEG24 (SEQ ID NO: 19)) was manufactured by PolyPeptide Group (San Diego, Calif.) to ≥95% purity verified by HPLC and mass spectrometry analysis. Lyophilized PA-dPEG24 was solubilized in normal saline with 0.01 M $Na_2HPO_4$ buffer to 37.5 mM. Purified MPO was purchased from Lee Biosolutions (Maryland Heights, Mo.). Intravenous Immune Globulin was purchased from Baxter Healthcare Corporation (Westlake Village, Calif.), Ovalbumin from Sigma Aldrich (St Louis, Mo.), and the Anti-ovalbumin antibody from Abcam (Cambridge, Mass.). Goat anti-C1q and human C1 were purchased from Complement Technology (Tyler Tex.). PMA (Phorbol 12-myristate 13-acetate) and hydrogen peroxide were purchased from Fisher Scientific (Hampton, N.H.).

The complement permissive $GVBS^{++}$ buffer was veronal-buffered saline with 0.1% gelatin, 0.15 M $CaCl_2$, and 1 mM $MgCl_2$ [29]. The complement inhibitory buffer GVBS** was a veronal-buffered saline with 0.1% gelatin and 10 mM EDTA. Pooled normal human serum (NHS) was prepared as previously described [29].

Immune complex activation of NHS was performed as follows. NHS was stimulated with three different types of immune complexes (IC) to induce complement activation. Heat-aggregated IgG was generated by incubating intravenous immune globulin at 50 mg/ml at 63° C. for 30 min [26]. Ovalbumin-antiovalbumin immune complexes were made by incubating 0.01 ml anti-ovalbumin antibody with an equal volume of ovalbumin, at 0.25 mg/nil, at 37° C. for 30 minutes and then storing at 4° C. overnight. C1 immune complexes were formed by incubating 0.02 ml anti-C1q goat sera with 5 µl of C1, at 200 µg/ml, at 30° C. for 30 minutes and then placing in an ice water bath. For C5a and C5b-9 assays, activation of NHS was performed by pre-incubating 5% NHS with titrating concentrations of PA-dPEG24 in 0.3 ml of GVBS" buffer for 30 minutes at room temperature. Then 2 ml of either heat-aggregated IVIg, or ovalbumin IC, or 5 of C1-antiC1q IC was added to the mix for 30 min. at 37° C. This reaction was stopped with the addition of an equal volume of GVBS**. For iC3b detection, 1% NHS was used and the rest of the protocol remained the same.

ELISA was performed as follows. Samples were assayed using C5a, iC3b, and SC5b-9 ELISAs. A C5a ELISA kit (R&D Systems) was used per the manufacturer's instructions. ELISAs for iC3b and SC5b-9 were performed as previously described [30]. In iC3b ELISA, a goat anti-human C3 antibody (Complement Technology, Tyler Tex.) was used in for capture, a mouse anti-human iC3b antibody (Quidel, San Diego Calif.) for probing, and a goat anti-mouse HRP antibody for detection. In SC5b-9 ELISA, a rabbit anti-human SC5b-9 antibody (Complement Technology) was used for capture, a mouse anti-human SC5b-9 monoclonal antibody (Quidel) for probing, and a chicken anti-mouse HRP antibody for detection. Colorimetric detection was performed with TMB, stopped with $H_2SO_4$ and read on a BioTek Synergy HT plate reader at 450 nm.

Neutrophils from the blood of healthy volunteers were purified from heparinized blood by Hypaque-Ficoll step gradient centrifugation, dextran sedimentation, and hypotonic lysis, as previously described [31].

A Neutrophil Extracellular Trap assay was performed in a microtiter plate as follows. The formation of NETs was induced by incubating $2.0 \times 10^5$ neutrophils in a 96 well tissue culture plates with RPMI media alone, or adding 0.05% of $H_2O_2$, or 12 nM PMA, or 8 µg/ml MPO, or PA-dPEG24 at various concentrations. For immune complex sera induced NET formation, activated sera was made by adding 5 µl of ovalbumin-anti-ovalbumin immune complex to 5% NHS in 0.3 ml of GVBS**. This combination was allowed to incubate for 30 minutes at 37° C., and then 0.05 ml was added to the neutrophils in RPMI. Cells were then incubated for 1.5 hours at 37° C. in 5% $CO_2$ incubator.

NET formation was quantitatively assayed as follows. Free DNA was measured by PicoGreen in the supernatant recovered from the NET microtiter plate well assay [18]. Five hundred units of monococcal nuclease (Fisher) were added to each well to allow for digestion of released extracellular DNA for 10 minutes in 37° C. incubator. The preparation was then aliquoted into an adjacent well and mixed 1:1 with prepared PICO green reagent (Fisher). The fluorescence was then quantified on a BioTek microplate reader at Excitation 485 nm/Emission 528 nm.

NET formation was assayed by fluorescence microscopy. Purified human neutrophils were assayed on a glass slide as follows. Cells were combined with RPMI media and the indicated stimuli as mentioned above in a tube and then aliquoted onto a glass slide circled with a hydrophobic slide marker. The slides were incubated for 1.5 hours at 37° C. in a 5% $CO_2$ incubator at 37 degrees for 1.5 hours. Slides were fixed overnight with 4% paraformaldehyde at 4° C.

For all staining, the following conditions were used. Slides were washed in PBS and incubated in blocking solution (2% normal goat serum+2% bovine serum albumin in PBS) for 1 hour at room temperature. Then the slides were incubated with primary antibody at 1:300 in 2% BSA in PBS for 1 hour at room temperature. Slides were washed in PBS 3 times and incubated in fluorescent-labeled secondary antibody at 1:1000 or DAPI (Southern Biotech) at 0.25 pg/ml final in 2% BSA in PBS for 1 hour at room temperature. Slides were then washed 3 times in PBS and were imaged. Cells were visualized using a DP70 Digital Camera (Olympus Center, Valley Forge, Pa.), mounted on a BX50, Olympus microscope. Staining antibody pairs used were rabbit anti-MPO (Thermo Scientific) and rabbit anti-Histone H3 (Abcam) with the secondary goat anti-rabbit Alexa Fluor 488 (Novus Biologicals). Also, mouse anti-elastase (Invitrogen) was used with the secondary goat anti-mouse Alexa Fluor 568 (Novus Biologicals).

Statistical analysis was performed as follows. Quantitative data were analyzed determining means, standard error (SEM), and Student's t-test [32] using Excel (Microsoft, Redmond, Wash.).

Figure 1B:
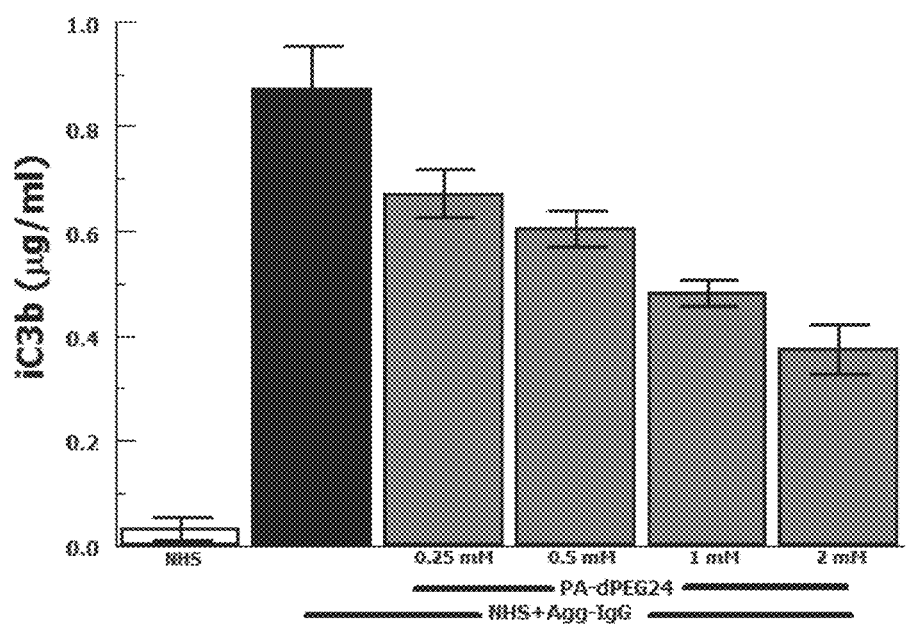
Figure 1C:
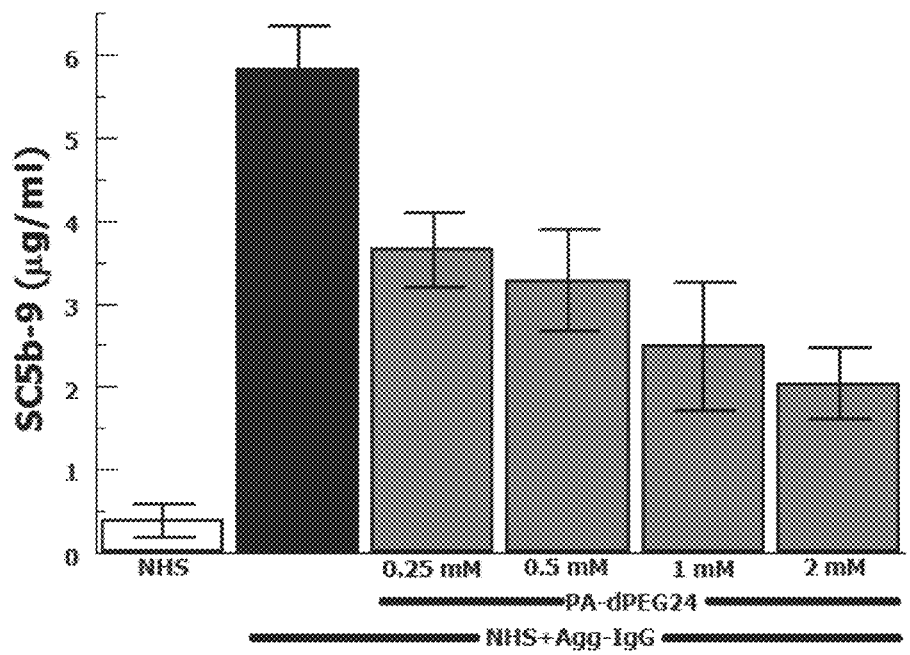

PA-dPEG24 was shown to inhibit immune complex-initiated complement activation. To evaluate the ability of PA-dPEG24 to inhibit immune complex-initiated complement activation, the archetypal immune complex stimulant of heat-aggregated IgG [25, 26] was utilized in pooled normal human serum (NHS). Three important effectors resulting from complement activation were assayed: the major pro inflammatory anaphylatoxin, C5a, a cleavage product of C3 activation, iC3b, and the membrane attack complex, C5b-9. The data is shown in FIGS. 1A-1C. FIG. 1A shows that PA-dPEG24 inhibits C5a generation in normal human serum (NHS) stimulated with heat-aggregated IgG (Agg-IgG) immune complexes. Five independent experiments were performed, with the SEM shown. FIG. 1B shows PA-dPEG24 inhibition of iC3b generation in normal human serum (NHS) stimulated with heat-aggregated IgG (Agg-IgG) immune complexes. Four independent experiments were performed, with the SEM shown. FIG. 1C shows PA-dPEG24 inhibition of SC5b-9 generation in normal human serum (NHS) stimulated with heat-aggregated IgG (Agg-IgG) immune complexes. Six independent experiments were performed, with the SEM shown.

For each assay, PA-dPEG24 dose-dependently inhibited elaboration of the effector after stimulation with heat-aggregated IgG compared with no inhibitor. Statistically significant inhibition was achieved in each assay at ≥0.5 mM PA-dPEG24 (P<0.05). For C5a, 1 mM PA-dPEG24 lead to a 61% reduction (P=0.002) compared with heat-aggregated IgG with no inhibitor. These results suggest that PA-dPEG24 can inhibit immune complex-initiated complement activation in human sera.

Figure 2A:
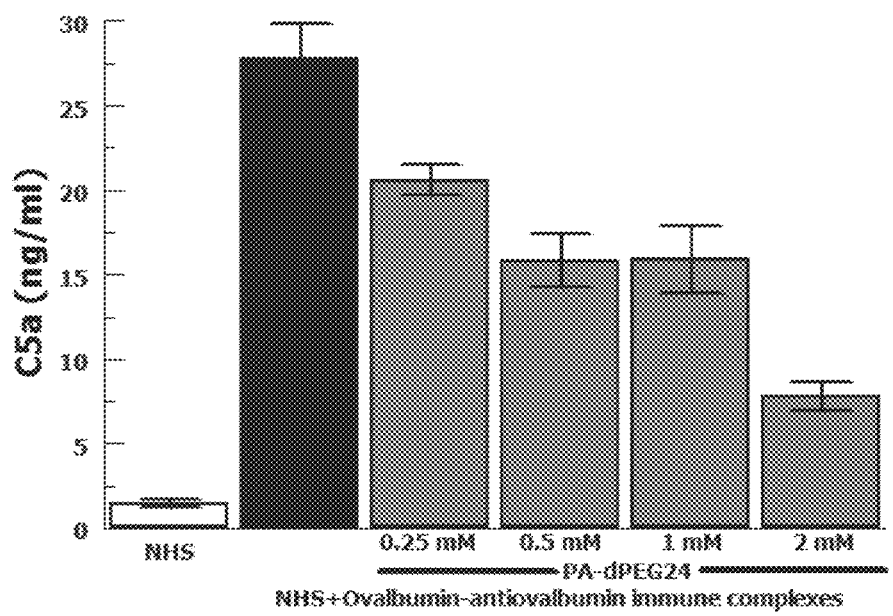
FIGS. 2A-2C are graphs showing PA-dPEG24 inhibition of ovalbumin-antiovalbumin immune complex-initiated complement activation assayed by complement effectors.
Figure 2B:
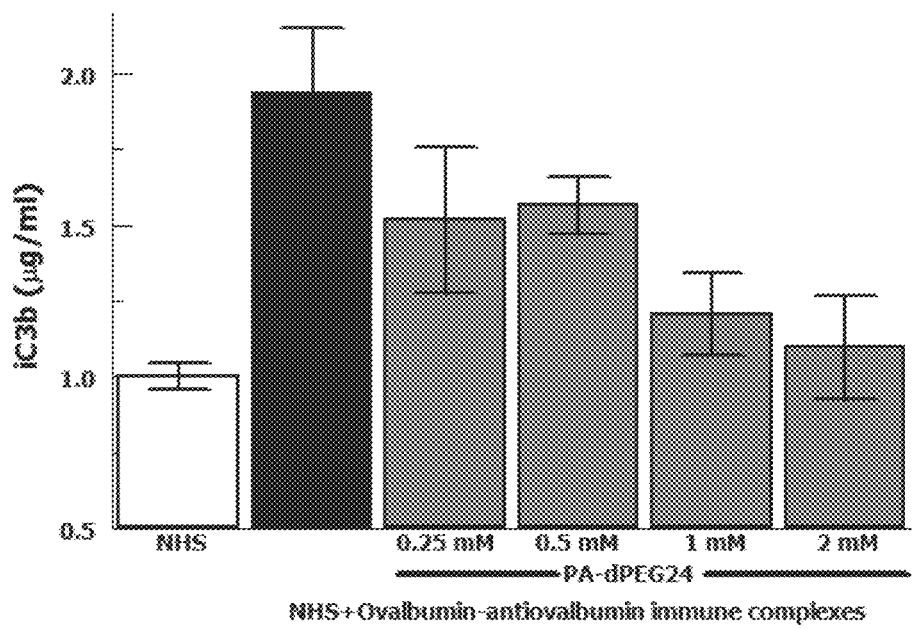
Figure 2C:
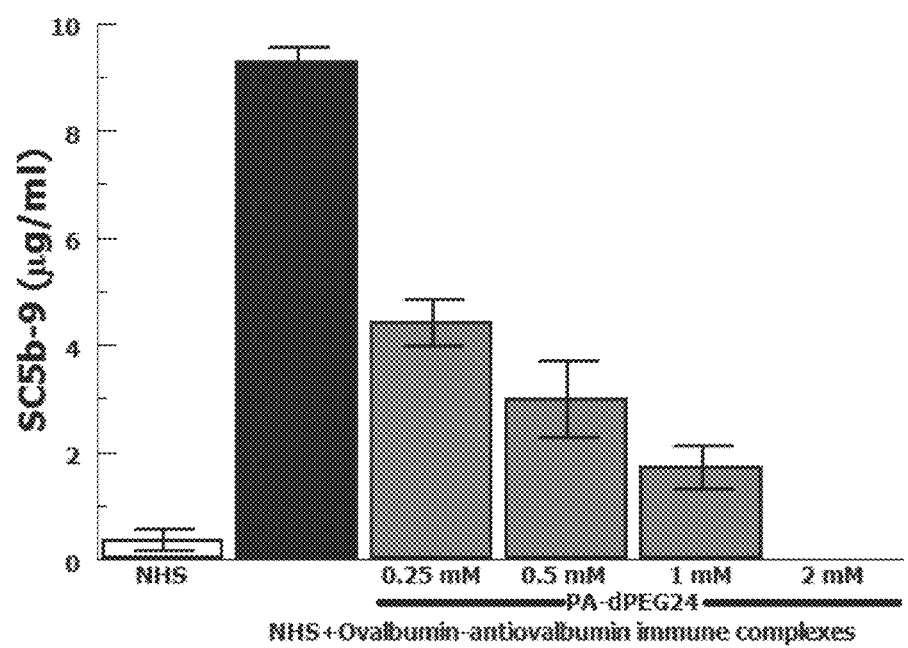

To provide confirmation of the results with heat-aggregated IgG, the antigen-antibody immune complex most often utilized in animal models of complement activation, ovalbumin and antiovalbumin [27, 28], was then tested. The ovalbumin-antiovalbumin immune complexes were used to stimulate complement activation in NHS and the same three effectors, C5a, iC3b and C5b-9, were measured. PA-dPEG24 dose dependently inhibited generation of each complement effector with statistically significant inhibition achieved at ≥0.25 mM PA-dPEG24 (P<0.03) compared with ovalbumin-antiovalbumin alone. The data is shown in FIGS. 2A-2C. FIG. 2A shows PA-dPEG24 inhibition of C5a generation in normal human serum (NHS) stimulated with ovalbumin-antiovalbumin immune complexes. Four independent experiments were performed, with the SEM shown. FIG. 2B shows PA-dPEG24 inhibition of iC3b generation in normal human serum (NHS) stimulated with ovalbumin-antiovalbumin immune complexes. Four independent experiments were performed, with the SEM shown. FIG. 2C shows PA-dPEG24 inhibition of SC5b-9 generation in normal human serum (NHS) stimulated with ovalbumin-antiovalbumin immune complexes. At 2 mM PA-dPEG24 the measured SC5b-9 was at the lower limit of detection. Three independent experiments were performed, with the SEM shown. These results provide additional confidence that PA-dPEG24 can inhibit immune complex-initiated complement activation in human sera.

Due to the importance of anti-C1q antibodies in a subset of patients with SLE, immune complexes with human C1 and anti-C1 q antibodies (goat) were generated. These immune complexes activated NHS leading to robust generation of C5a, iC3b and SC5b-9. The data is shown in FIGS. 3A-3C.

Figure 3A:
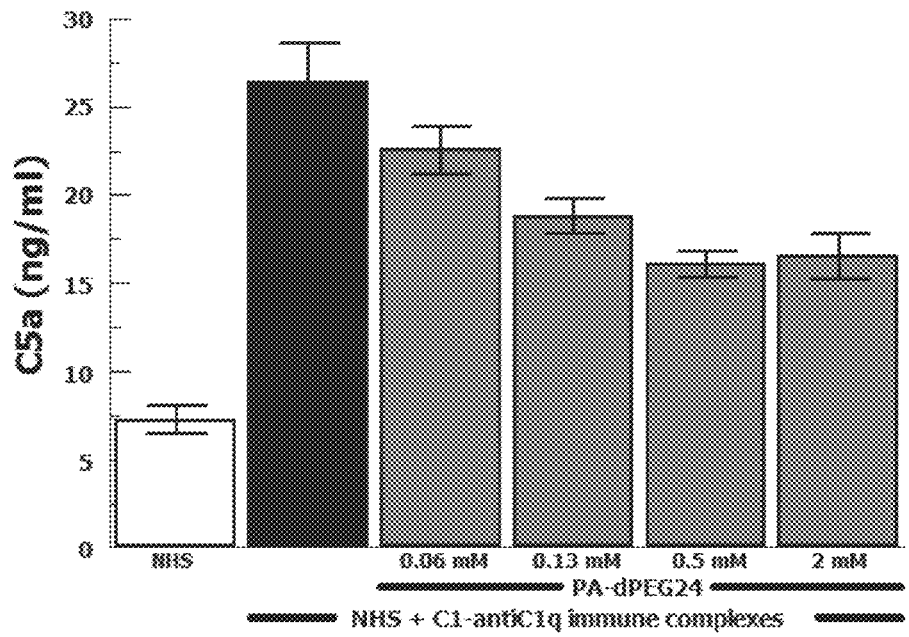
FIGS. 3A-3C are graphs showing PA-dPEG24 inhibition of C1-antiC1q immune complex-initiated complement activation assayed by complement effectors.
Figure 3B:
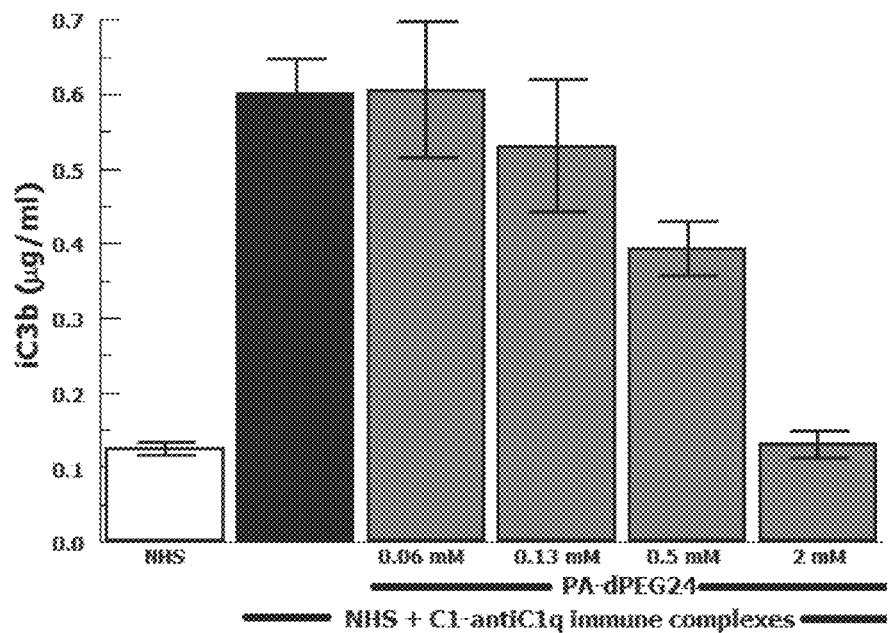
Figure 3C:
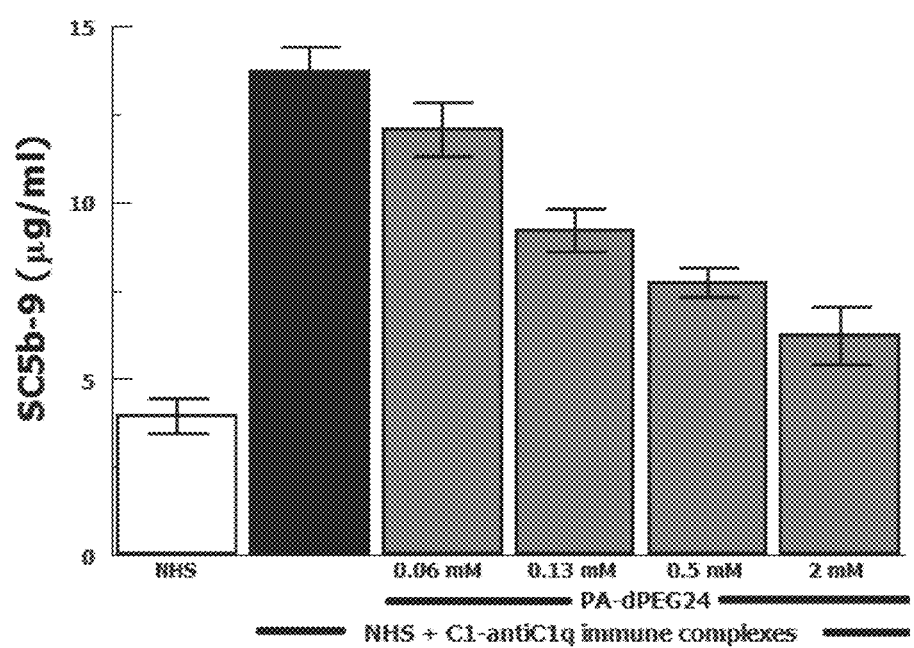

FIG. 3A shows PA-dPEG24 inhibition of C5a generation in normal human serum (NHS) stimulated with C1-antiC1q immune complexes. Four independent experiments were performed, with the SEM shown. FIG. 3B shows PA-dPEG24 inhibition of iC3b generation in normal human serum (NHS) stimulated with C1-antiC1q immune complexes. Four independent experiments were performed, with the SEM shown. FIG. 3C shows PA-dPEG24 inhibition of SC5b-9 generation in normal human serum (NHS) stimulated with C1-antiC1q immune complexes. Four independent experiments were performed, with the SEM shown.

PA-dPEG24 dose-dependently inhibited C1-antiC1q generation of C5a in NHS at each concentration ($P \leq 0.03$). C1-antiC1q generation of iC3b was inhibited by 2 mM PA-dPEG24 ($P<0.02$) to a level similar to NHS baseline. PA-dPEG24 dose-dependently inhibited C1-antiC1q generation of SC5b-9 for concentrations $\geq 0.13$ mM ($P<0.03$). These results show that PA-dPEG24 can inhibit C1-antiC1q immune complex-initiated complement activation in human sera.

PA-dPEG24 was shown to inhibit PMA-initiated NET formation by human neutrophils. To evaluate whether PA-dPEG24 can inhibit neutrophil extracellular trap (NET), purified human neutrophils and the commonly utilized stimulus phorbol 12-mystate 13-acetate (PMA) were used in a manner similar to methods described by Akong-Moore et al [18]. Extracellular DNA and myeloperoxidase (two major components of NETs) were visualized with DNA and anti-MPO antibody, respectively.

Figure 4:
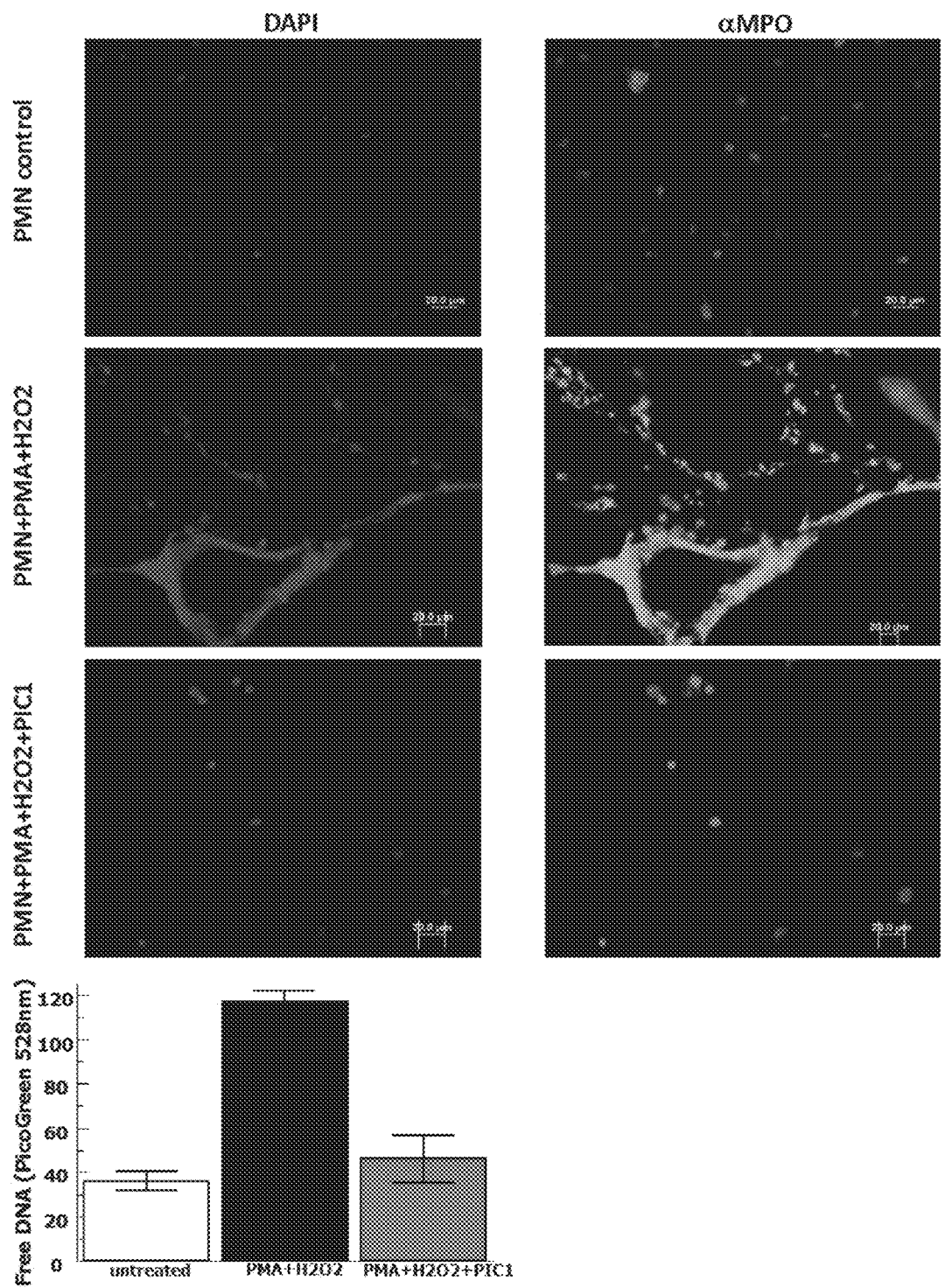
FIG. 4 shows PA-dPEG24 inhibition of PMA-initiated NET formation with human neutrophils (PMN) assayed by fluorescence microscopy and PicoGreen quantitation of free DNA. The first row shows unstimulated neutrophils, the second row shows neutrophils stimulated with PMA and hydrogen peroxide ($H_2O_2$) and the third row shows neutrophils stimulated with PMA+$H_2O_2$ in the presence of 5 mM PA-dPEG24 (PIC1). The first column shows slides probed with DAPI to visualize DNA and the second column shows slides probed with anti-MPO antibody. The graph shows PA-dPEG24 (5 mM) inhibition of NET generation by human neutrophils stimulated with PMA+$H_2O_2$ assayed by PicoGreen. The data shown are means of (n=3) independent experiments and the standard error of the mean (SEM).

Human neutrophils stimulated with PMA and hydrogen peroxide generated many NETs visualized by fluorescence microscopy of extracellular DNA and extracellular MPO. FIG. 4 shows PA-dPEG24 inhibition of PMA-initiated NET formation with human neutrophils (PMN) assayed by fluorescence microscopy and PicoGreen quantitation of free DNA. The first row shows unstimulated neutrophils, the second row shows neutrophils stimulated with PMA and hydrogen peroxide ($H_2O_2$) and third row shows neutrophils stimulated with PMA+$H_2O_2$ in the presence of 5 mM PA-dPEG24 (PIC1). The first column are slides probed with DAPI to visualize DNA and the second column are slides probed with anti-MPO antibody. The graph shows PA-dPEG24 (5 mM) inhibition of NET generation by human neutrophils stimulated with PMA+$H_2O_2$ assayed by PicoGreen. Three independent experiments were performed, with the SEM shown.

In the presence of 5 mM PA-dPEG24, PMA and hydrogen peroxide did not generate NETs that could be identified by fluorescence microscopy. NET formation was then quantified by measuring free DNA in a PicoGreen-based assay from supernatants of human neutrophils stimulated in microtiter plate wells. PA-dPEG24 (5 mM) was able to inhibit free DNA elaboration by 2.6-fold ($P=0.01$) in the presence of PMA and hydrogen peroxide compared with no inhibitor (FIG. 4). This reduction for PA-dPEG24 was to a level similar to baseline without PMA.

Figure 5:
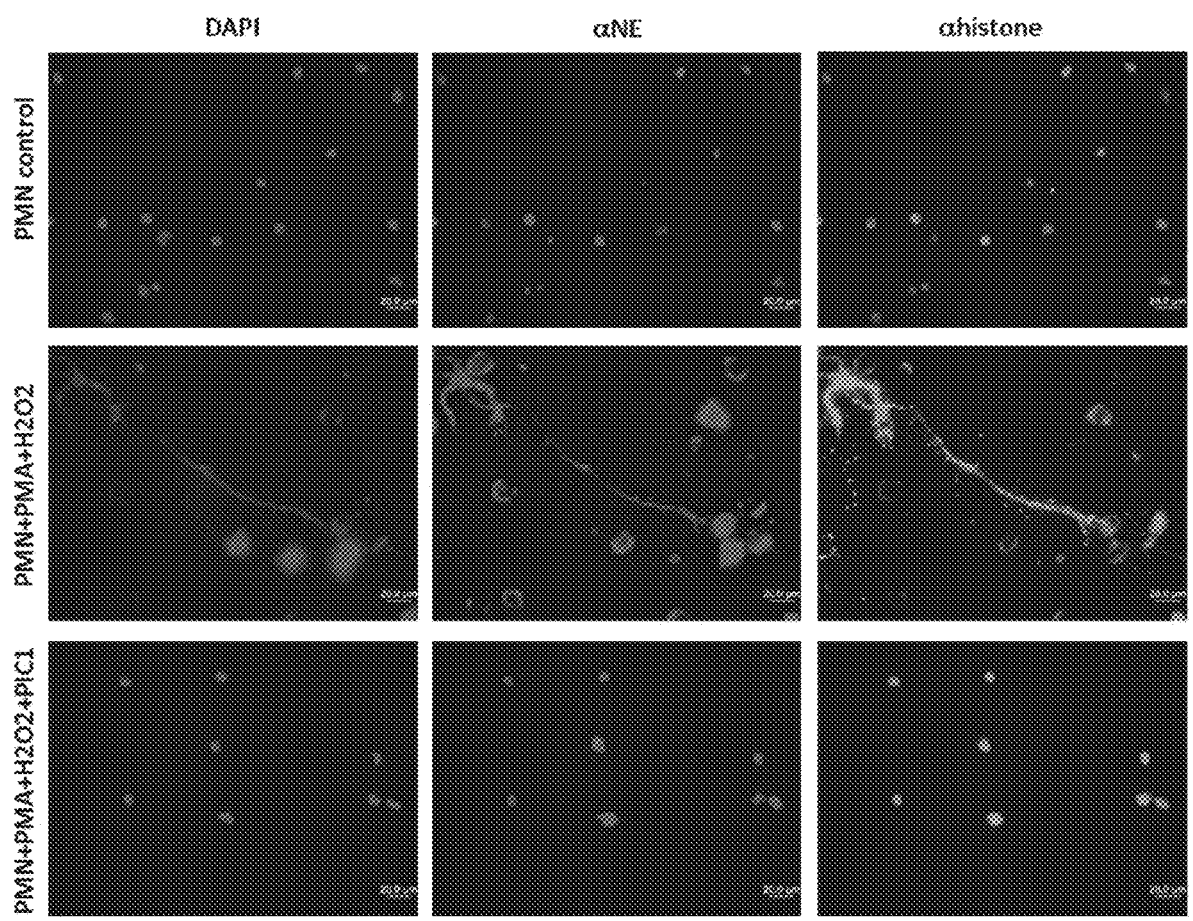
FIG. 5 shows PA-dPEG24 inhibition of PMA-initiated NET formation with human neutrophils (PMN) assayed by fluorescence microscopy for DNA (DAPI), neutrophil elastase (anti-NE antibody), and histone H3 (anti-histone H3 antibody). The first row shows unstimulated neutrophils, the second row shows neutrophils stimulated with PMA and hydrogen peroxide ($H_2O_2$) and third row shows neutrophils stimulated with PMA+$H_2O_2$ in the presence of 5 mM PA-dPEG24 (PIC1). The first column shows slides probed with DAPI to visualize DNA, the second column shows slides probed with anti-neutrophil elastase antibody and the third row shows slides probed with anti-histone H3 antibody. Representative images are shown.

Fluorescence microscopy was also performed utilizing the same experimental conditions, but instead additional NET constituents extracellular neutrophil elastase and histone H3 were probed. FIG. 5 shows PA-dPEG24 inhibition of PMA-initiated NET formation with human neutrophils (PMN) assayed by fluorescence microscopy for DNA (DAPI), neutrophil elastase ($\alpha$NE), and histone H3 ($\alpha$histone). The first row shows unstimulated neutrophils, the second row shows neutrophils stimulated with PMA and hydrogen peroxide ($H_2O_2$) and third row shows neutrophils stimulated with PMA+$H_2O_2$ in the presence of 5 mM PA-dPEG24 (PIC1). The first column are slides probed with DAPI to visualize DNA, the second column are slides probed with anti-neutrophil elastase antibody and the third row is probed with anti-histone H3 antibody. Representative images are shown.

The above show that stimulation with PMA and hydrogen peroxide resulted in copious NET formation, which was inhibited in the presence of PA-dPEG24 (5 mM). These results suggest that PA-dPEG24 can inhibit PMA-stimulated NET formation by human neutrophils.

Figure 6:
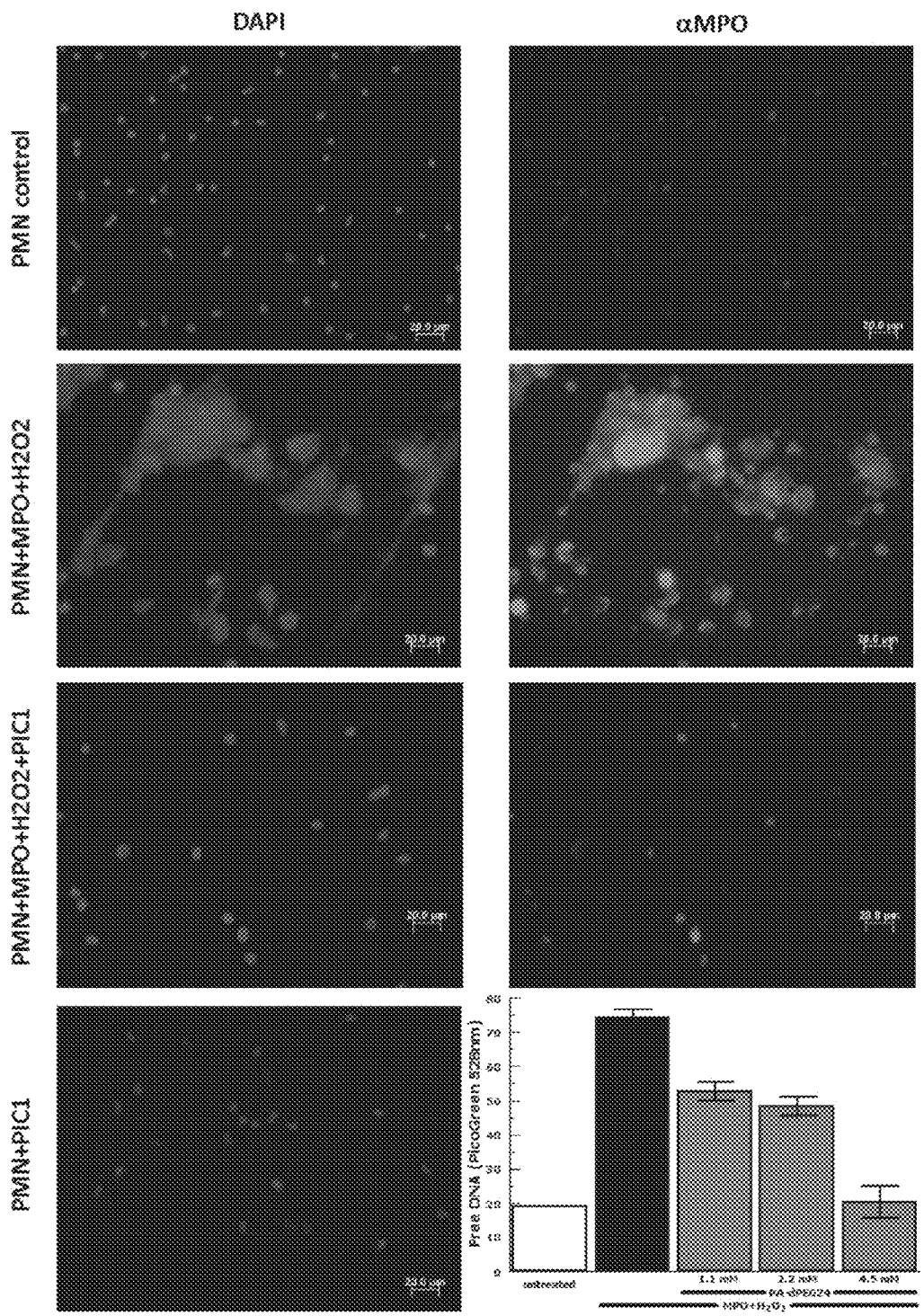
FIG. 6 shows PA-dPEG24 inhibition of MPO-initiated NET formation with human neutrophils (PMN) assayed by fluorescence microscopy and PicoGreen quantitation of free DNA. The first row shows unstimulated neutrophils, the second row shows neutrophils stimulated with MPO and hydrogen peroxide ($H_2O_2$), the third row shows neutrophils stimulated with MPO+$H_2O_2$ in the presence of PA-dPEG24 (PIC1) and the fourth row shows neutrophils incubated with PA-dPEG24 (PIC1) only. The first column shows slides probed with DAPI to visualize DNA. The second column shows slides probed with anti-MPO antibody. The graph shows PA-dPEG24 inhibition of NET generation by human neutrophils stimulated with MPO+hydrogen peroxide assayed by PicoGreen. The data shown are means of (n=3) independent experiments and the standard error of the mean (SEM).

PA-dPEG24 was shown to inhibit MPO-initiated NET formation by human neutrophils. Akong-Moore et al [18] suggest that MPO is a critical mediator in PMA-stimulated NET formation, however this was never tested using purified MPO. The above experiments with purified human neutrophils were repeated but with purified MPO substituted for PMA as the stimulus for NET formation. Neutrophil stimulation with purified MPO and hydrogen peroxide caused extensive NET formation visualized by DAPI staining and anti-MPO staining. FIG. 6 shows PA-dPEG24 inhibition of MPO-initiated NET formation with human neutrophils (PMN) assayed by fluorescence microscopy and PicoGreen quantitation of free DNA. The first row shows unstimulated neutrophils. The second row shows neutrophils stimulated with MPO and hydrogen peroxide ($H_2O_2$). The third row shows neutrophils stimulated with MPO+$H_2O_2$ in the presence of PA-dPEG24 (PIC1) and the fourth row shows neutrophils incubated with PA-dPEG24 (PIC1) only. The first column shows slides probed with DAPI to visualize DNA. The second column shows slides probed with anti-MPO antibody. The graph shows PA-dPEG24 inhibition of NET generation by human neutrophils stimulated with MPO+hydrogen peroxide assayed by PicoGreen. Three independent experiments were performed, with the SEM shown.

NET formation in presence of MPO and hydrogen peroxide was blocked with PA-dPEG24 (5 mM). Neutrophils incubated with PA-dPEG24 alone appeared normal by fluorescence microscopy. When NET formation was quantified by PicoGreen measurement, 1.1 mM of PA-dPEG24 lead to a 30% ($P=0.02$) reduction in free DNA and 4.5 mM of PA-dPEG24 resulted in a 3.7-fold ($P=0.001$) reduction in free DNA compared with stimulation with MPO, but no inhibitor (FIG. 6). In the presence of MPO plus 4.5 mM PA-dPEG24, measured free DNA was not statistically different from unstimulated neutrophils. These results suggest that PA-dPEG24 inhibits NET formation via the MPO-mediated pathway.

Figure 7A:
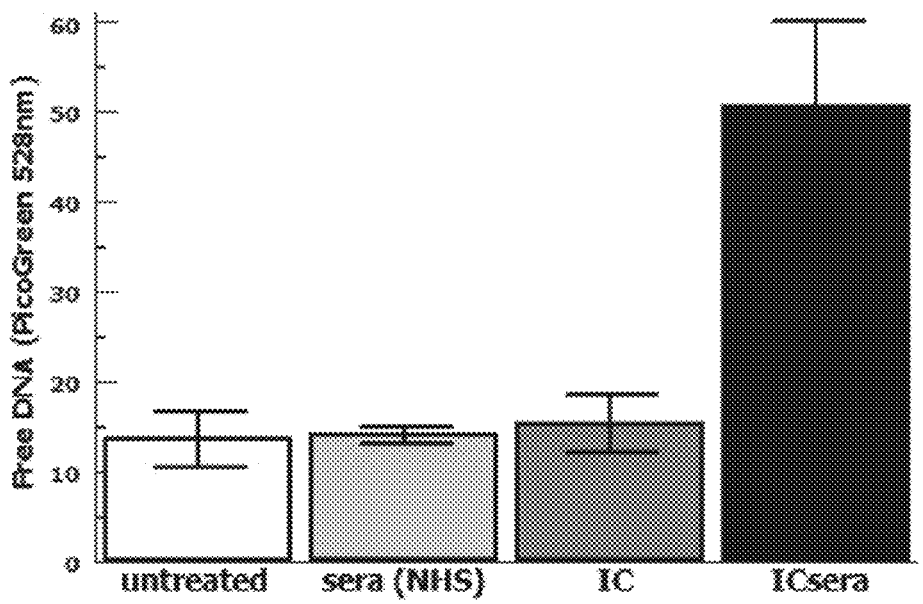
FIGS. 7A-7C show PA-dPEG24 inhibition of immune complex-activated serum-initiated NET formation with human neutrophils (PMN) assayed by fluorescence microscopy and PicoGreen quantitation of free DNA.

PA-dPEG24 inhibits immune complex-initiated NET formation by human neutrophils. A potential relationship between immune complex-initiated complement-activated human sera and NET formation by human neutrophils was evaluated. Complement in normal human sera was activated with ovalbumin-antiovalbumin immune complexes, as was performed in the experiments of FIG. 2. The immune complex-initiated complement-activated human sera was then incubated with purified human neutrophils resulting in NET formation quantified by free DNA measurement with PicoGreen. The relative contribution of immune complexes was initially evaluated by themselves compared with immune complex-initiated complement-activated human sera for generation of NETs. The presence of immune complexes by themselves did not significantly (P=0.39) increase NET formation compared with neutrophils alone (FIG. 7A). However, immune complex activation of complement in sera increased NET formation >20-fold (P=0.009) compared with immune complexes alone after subtracting the background. These results demonstrate for the first time that immune complex-initiated complement-activated sera is a strong stimulus for NET formation.

Figure 7B:
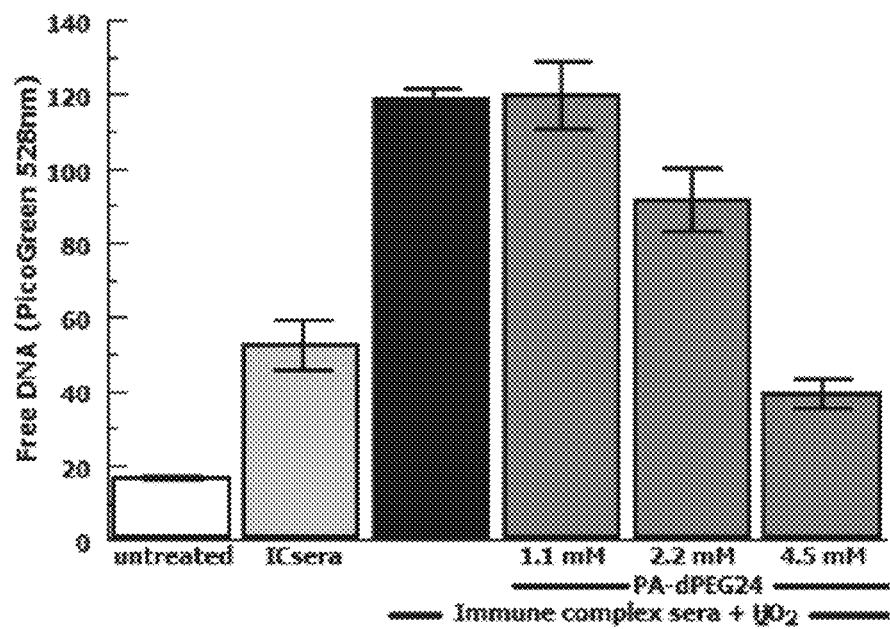
Figure 7C:
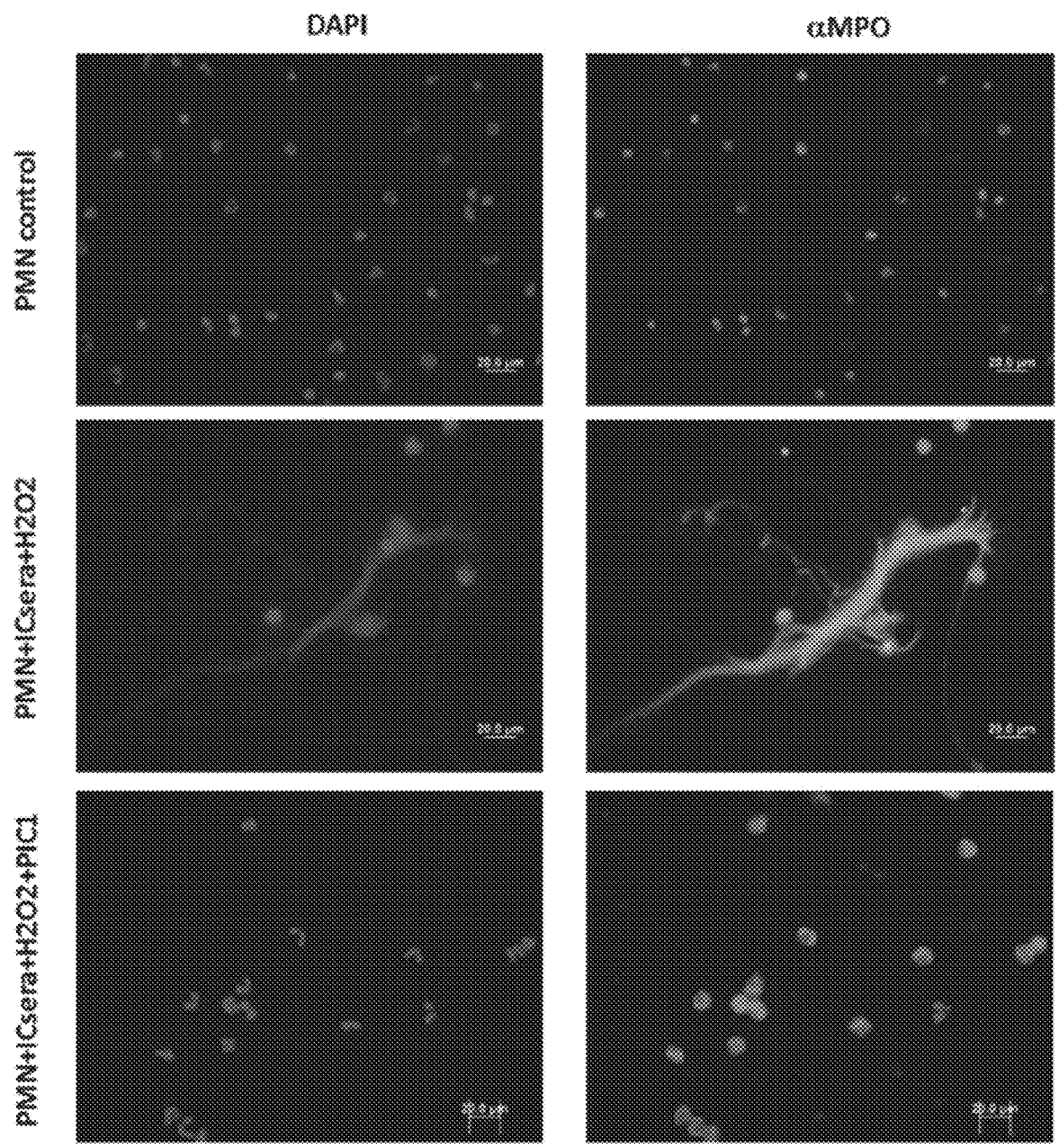

Hydrogen peroxide was tested to determine whether it further enhanced NET formation by immune complex-activated sera, with hydrogen peroxide approximately doubling the signal (FIG. 7B). Testing of PA-dPEG24 inhibition of NETosis was performed with PA-dPEG24 added after complement activation of the sera by immune complexes had already been allowed to occur. Therefore, any effect of PA-dPEG24 on NETosis happened downstream of complement activation. In the presence of immune complex-activated sera and hydrogen peroxide, 2.2 mM PA-dPEG24 decreased free DNA by 23% (P=0.037) and 4.5 mM PA-dPEG24 decreased free DNA by 3-fold (P<0.001) compared with no inhibitor (FIG. 7B). These conditions were also visualized by fluorescence microscopy (FIG. 7C). In the presence of PA-dPEG24 (5 mM) and immune complex-initiated complement-activated sera no NETs were identified by fluorescence microscopy.

These findings suggest that immune complex activated human sera can stimulate human neutrophils to form NETs and that this can be inhibited with PA-dPEG24. Inhibition of NETosis by PA-dPEG24 was a surprising finding given that the inhibition of NET formation occurred after complement activation had occurred in the serum and thus the initiating stimulus was unaffected. These results suggest the novel idea that immune complex-initiated complement-activated sera may cause NETosis via an MPO-mediated pathway, which was blocked with PA-dPEG24. Taken together, these experiments consistently show that PA-dPEG24 can inhibit NET formation by human neutrophils initiated by a variety of stimulants.

In conclusion, the lead PIC1 derivative, PA-dPEG24 (IALILEPICCQERAA-dPEG24 (SEQ ID NO: 19)), was able to dose-dependently inhibit complement activation initiated by multiple types of immune complexes, including C1-antiC1q immune complexes, limiting the generation of pro-inflammatory complement effectors including C5a and membrane attack complex (sC5b-9). PA-dPEG24 was also able to dose-dependently inhibit NET formation by human neutrophils stimulated by phorbol 12-mystate 13-acetate (PMA), myeloperoxidase (MPO) or immune complex activated human sera. These results suggest that PA-dPEG24 inhibition of NETs occurs by blocking the MPO pathway of NET formation. Together these results demonstrate that PA-dPEG24 can inhibit immune complex activation of the complement system and NET formation, suggesting that PIC1 peptides could be used as a therapeutic approach to modulate these two critical aspects of SLE pathogenesis that are not addressed by current pharmacological treatments.

Example 2

In this Example, Wistar rats were primed with lipopolysaccharide followed by 30% transfusion of mismatched erythrocytes, against which the rats have preexisting antibodies. Sham and vehicle animals were used as controls with a subgroup of animals receiving PIC1 two minutes before transfusion. At 4 hours, blood was isolated for complete blood count. Isolated lung tissue was stained with hematoxylin and eosin and myeloperoxidase (MPO) activity in lung tissue was quantified in a functional assay. Free DNA in plasma was detected by PicoGreen staining.

This novel 'two-hit' model utilizing erythrocyte transfusion yielded a robust TRALI phenotype. Compared to vehicle controls, lungs of PIC1 treated animals showed reduced lung damage, neutrophil invasion and MPO activity in the lung tissue. Additionally, rats receiving PIC1 demonstrated a reduction of free DNA in the blood suggestive of attenuated neutrophil extracellular trap formation previously associated with TRALI. The results shown below demonstrate that PIC1 attenuates acute lung injury in a novel animal model of TRALI.

Adolescent male Wistar rats (200-250 g) were purchased from Hilltop Lab Animals with indwelling jugular catheters and used under Eastern Virginia Medical School (EVMS) IACUC (Institutional Animal Care and Use Committee) approved protocols.

Healthy human volunteer donated AB blood used to generate purified human red blood cells (RBCs) was obtained after written informed consent under an EVMS approved Institutional Review Board protocol (EVMS IRB #02-06-EX 0216). Human RBCs acquired the morning of the animal experiments were processed as described previously. Human blood was purified on a Histopaque gradient by centrifugation. The RBCs were then separated from white blood cells and platelets and resuspended in saline. Rats (200 g) have a nominal circulating blood volume of 14 mL with a nominal 40% hematocrit. For transfusion, approximately 2 mL of human RBC at 80% hematocrit was transfused, which results in approximately 30% transfusion to the rats.

Plasma generated from the above experiments was analyzed for free hemoglobin using spectrophotometry, as described previously. Donor erythrocytes were hemolyzed with water to generate a standard curve from which the amount of hemolyzed erythrocytes in each sample was calculated with respect to the free hemoglobin measurements.

Flow cytometry was performed using a FACSCalibur flow cytometer (Becton Dickinson, Franklin Lakes, N.J., USA) with DXP 8 Color 488/637/407 upgrade (Cytek Development, Freemont, Calif., USA). The data was acquired using Cytek FlowJo CE version 7.5.110.6. Approximately $1 \times 10^5$ events, selected for erythrocytes, per sample were gathered for single labeled flow, respectively. Data was analyzed using FlowJo X version 10.0.7r2 (FlowJo LLC).

For single labeled flow, the cells collected after separating the plasma were washed, diluted and stained with FITC-conjugated anti-human CD235a (glycophorin A, eBioscience) at 1:200 in GVBS (veronal-buffered saline (VBS) with 0.1% gelatin, 0.01 mol/L EDTA (ethylenediaminetetraacetic acid)) for 20 min while shaking at room temperature to minimize agglutination. An antibody control consisted of mouse IgG2b Iso-control FITC at 1:200 (eBioscience).

Lung tissue stained with H&E was analyzed by a clinician blinded to the experimental groups (vehicle only and PIC1-treated animals). Neutrophil infiltration and cell wall thickening were scored on a scale of 0-4: 0=normal lungs, 1=minor lung involvement, 2=moderate lung involvement, 3=serious lung involvement, 4=severe lung involvement.

A myeloperoxidase (MPO) activity assay was conducted as follows. Frozen lung tissue was diced and homogenized on ice in 50 mM potassium phosphate, and centrifuged at 10,000 RPM at 4° C. for 15 minutes after which the supernatant was discarded. To solubilize MPO from the neutrophils in lung tissue, the pellet was resuspended in 500 ml 50 mM hexadecyltrimethylammonium bromide (HTAB), homogenized by sonication and snap frozen in liquid nitrogen. This process was repeated twice and samples were then centrifuged at 10,000 RPM at 4° C. for 10 minutes and supernatant collected.

Peroxidase activity in these samples was measured using 10-actyl-3,7-dihydroxyphenoxazine (ADHP, Amplex Red) following MPO antibody capture from samples as previously described. Fluorescence was read from 0 to 600 seconds in twenty-five second intervals which provided twenty-five data points per well at an excitation wavelength of 535 nm and emission wavelength of 590 nm using a BioTek microplate reader. Purified MPO was used as a positive control and phosphate buffered saline (PBS) as a negative control. All activity assays were performed in triplicate.

Free DNA was measured by PicoGreen in rat plasma as previously described. Briefly, plasma samples were diluted 1:10 in 10 mM Tris-HCl, 1 mM EDTA, pH 8.0 (TE) buffer and 50 uL of each sample was added to the wells along with 50 uL of a 1:200 dilution of PicoGreen (Life Technologies) and incubated at room temperature for 10 minutes, protected from light. A DNA standard curve was prepared in TE Buffer. The fluorescence was then read at an excitation wavelength of 485 nm and an emission wavelength of 520 nm using a BioTek microplate reader. All free DNA measurements were done in triplicate.

Means and standard errors were calculated from independent experiments and statistical comparisons were made using Student t test (Microsoft Excel XP).

Figure 8A:
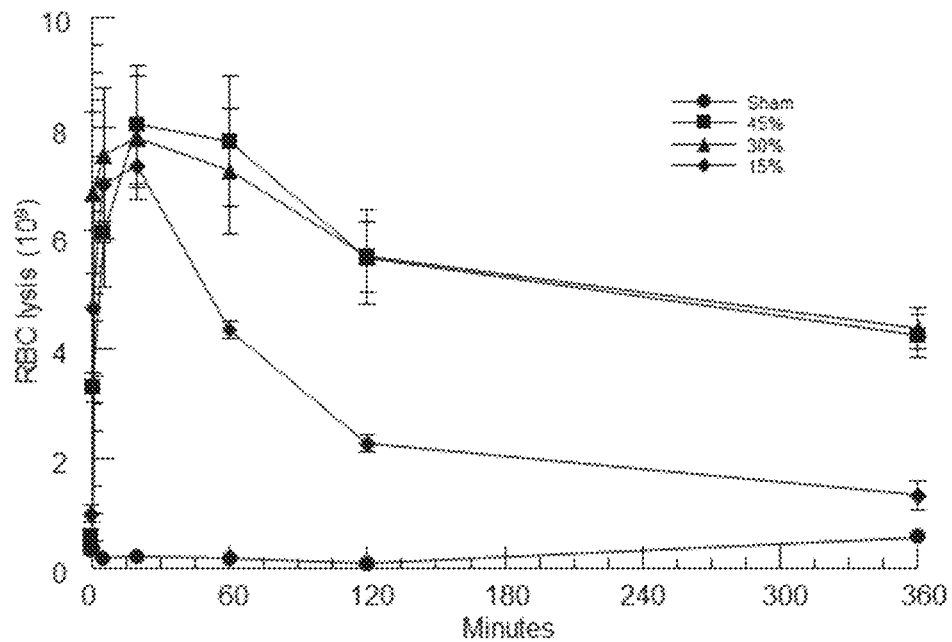
FIGS. 8A and 8B show the results of optimization of human RBC transfusion into rats.
Figure 8B:
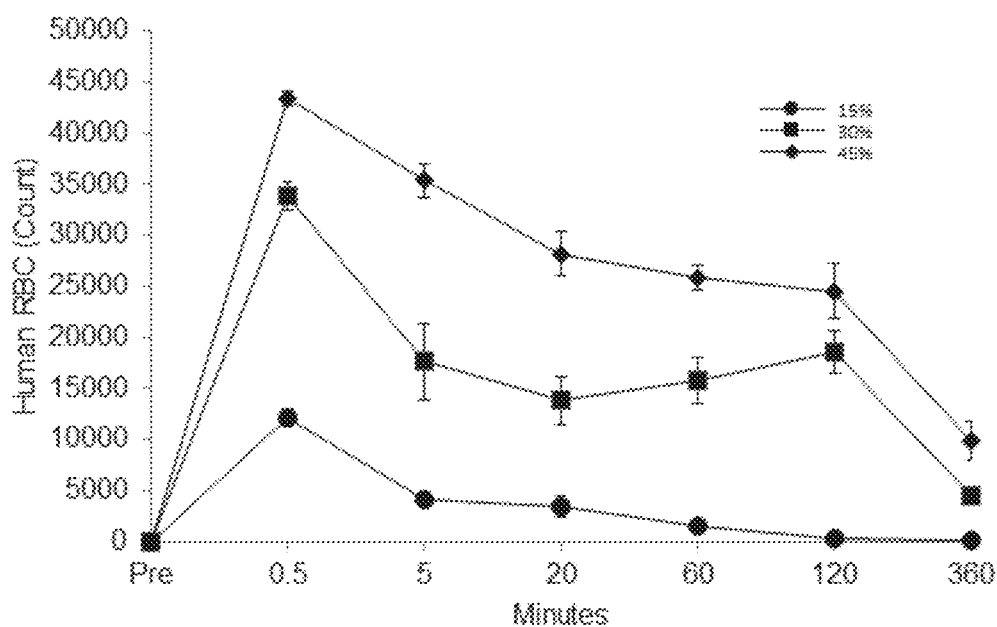
Figure 9A:
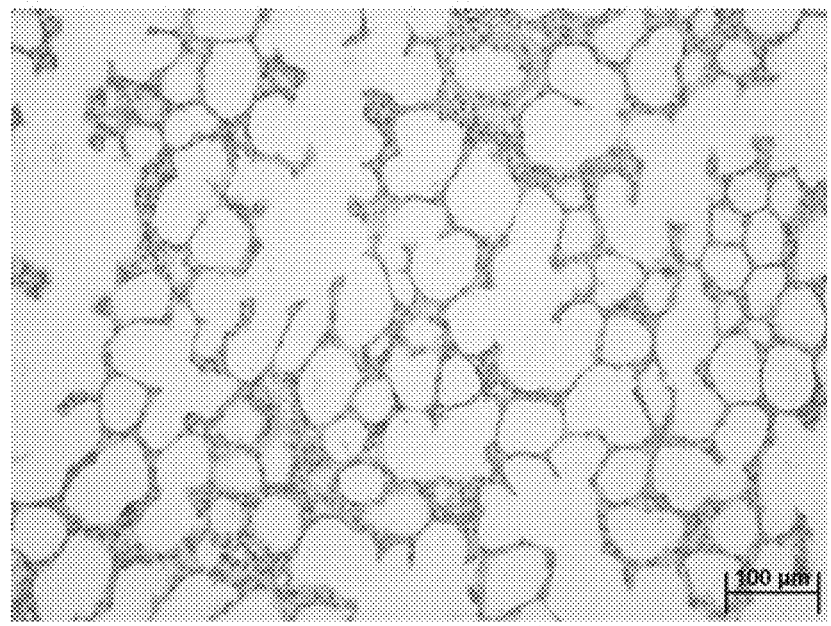
FIGS. 9A-9D show that an LPS "first-hit" is required for transfusion induced lung injury. Representative histology (hematoxylin and eosin) stains are shown of lungs from sham rats (FIG. 9A), rats receiving 30% (FIG. 9B), 45% transfusion of mismatched RBCs in the absence of LPS (FIG. 9C) and rats receiving 30% transfusion after LPS administration (FIG. 9D). Animals receiving transfusion in the absence of LPS demonstrated normal lung architecture as seen in sham treated animals whereas animals receiving LPS prior to 30% transfusion showed severe neutrophil infiltration and thickening of the alveolar cell walls. Bar represents 100 µm. Tissues were observed with a microscope (BX50, Olympus) at a magnification of 20× at room temperature. Images were acquired with a digital camera (DP70, Olympus).
Figure 9B:
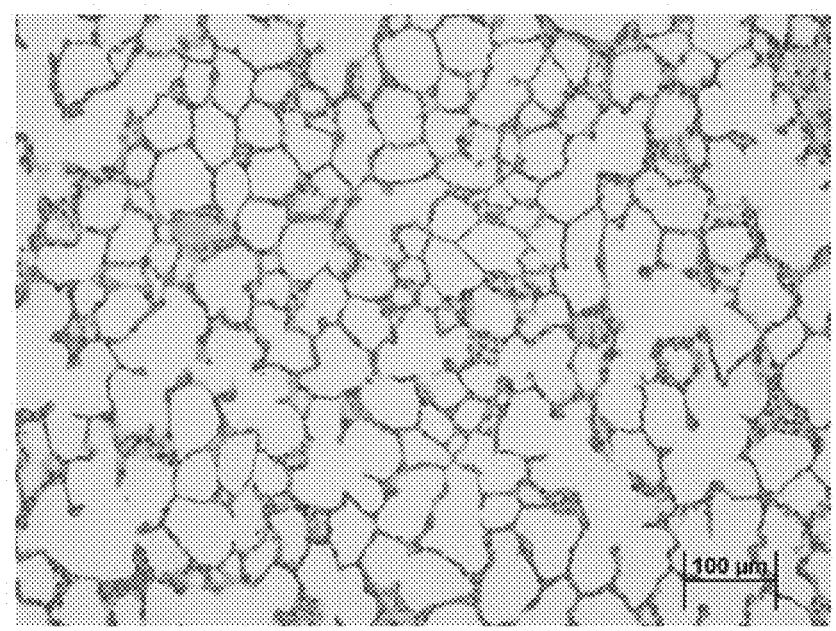
Figure 9C:
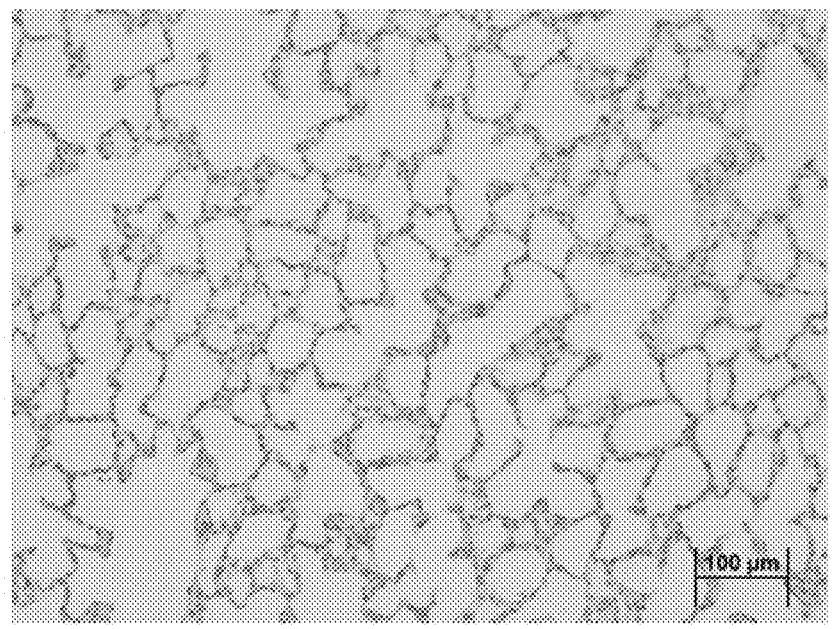

In a rat model of acute intravascular hemolytic transfusion reaction (AIHTR), transfusion of 15% mismatched RBCs resulted in intravascular hemolysis and acute kidney damage. In this model, naturally circulating anti-A antibodies in Wistar rats initiate classical complement activation and hemolysis of the transfused erythrocytes. To ascertain if the AIHTR model could be adapted to mimic a TRALI phenotype, ascending doses of mismatched RBC transfusions (15, 30 or 45%) were initially tested and it was determined that a 30% transfusion produces near maximal amounts of complement-mediated hemolysis (FIG. 8A). Saturation at 45% transfusion suggests that the amount of antibody binding the erythrocytes with sufficient clustering to initiation complement activation has likely been exceeded. The 30% transfusion produced an intermediate phenotype of RBC survival compared to the 15 and 45% transfusions as assessed by flow cytometry (FIG. 8B). At 4 hours post transfusion, no histological lung damage occurred, even at 45% transfusion (FIGS. 9A-9C).

Figure 10A:
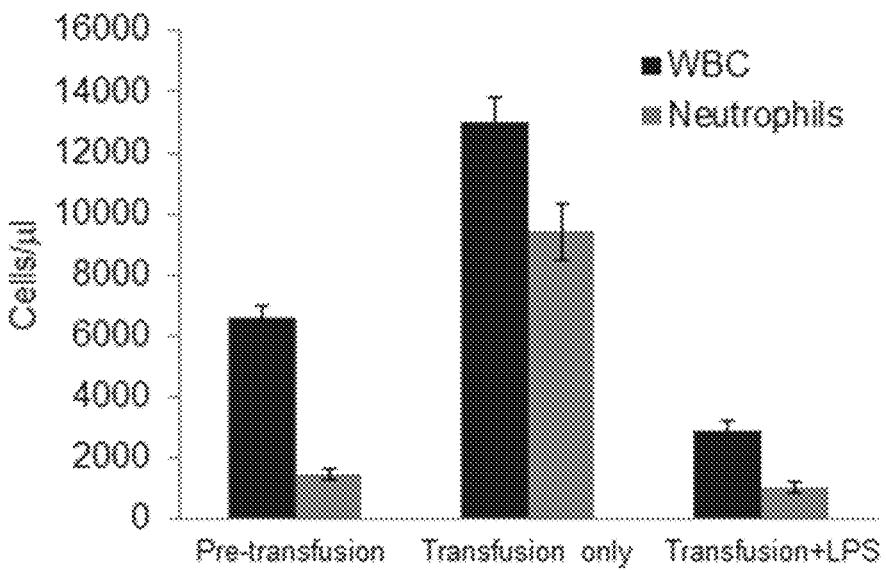
FIGS. 10A-10C are graphs showing that an LPS "first-hit" induces leukopenia. Blood was collected from rats before infusion of 30% mismatched RBC not receiving LPS pre-treatment or with LPS pre-treatment (pre-transfusion, n=22). Four hours after transfusion, blood was again collected from rats transfused without (transfusion only, n=5) or with LPS (transfusion+LPS, n=3). Levels of WBCs and neutrophils (FIG. 10A), monocytes (FIG. 10B) and lymphocytes (FIG. 10C) are reported. The data shown are means and standard deviation of the mean.
Figure 10B:
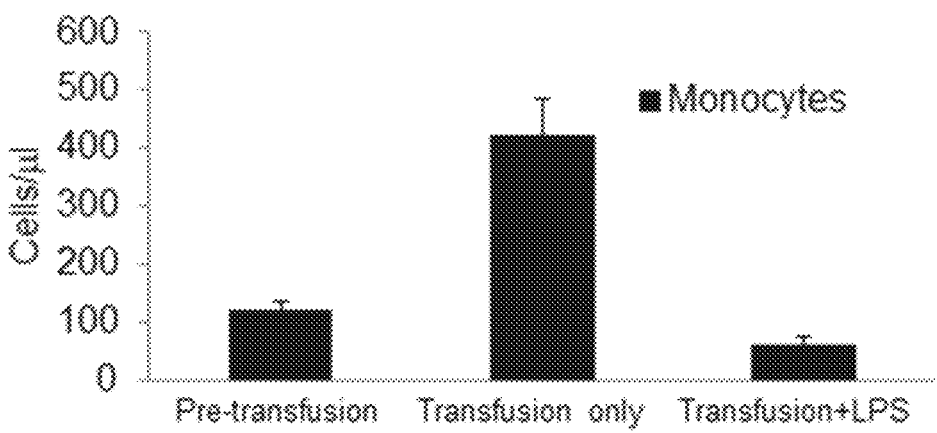
Figure 10C:
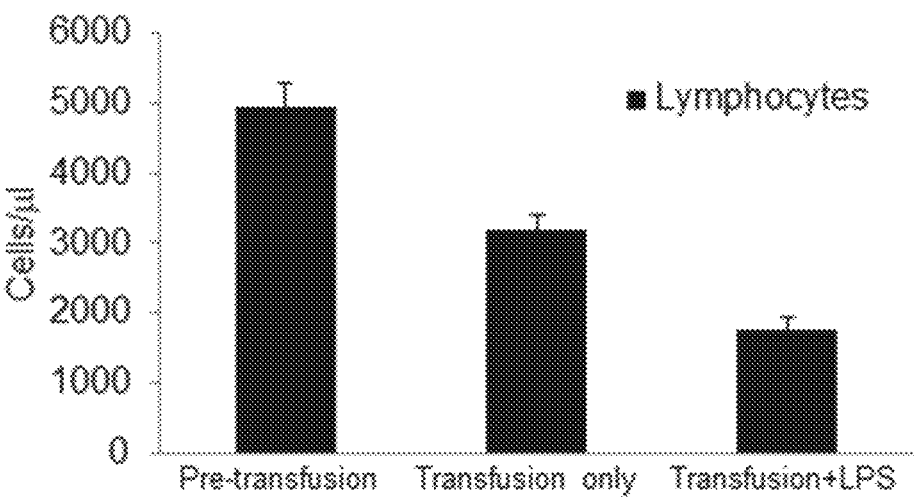

A significant increase in white blood cells (WBC) ($P=1.08\times10^{-6}$), neutrophils ($P=2.70\times10^{-13}$) and monocytes ($P=2.59\times10^{-7}$) in the blood was observed after 30% transfusion, as compared to pre-transfusion cell counts. Leukocytes were mobilized, but did not localize to the lung (FIGS. 10A-10B). There was, interestingly, a significant decrease in lymphocytes in the bloodstream after the 30% transfusion ($P=0.015$) (FIG. 10C).

Figure 9D:
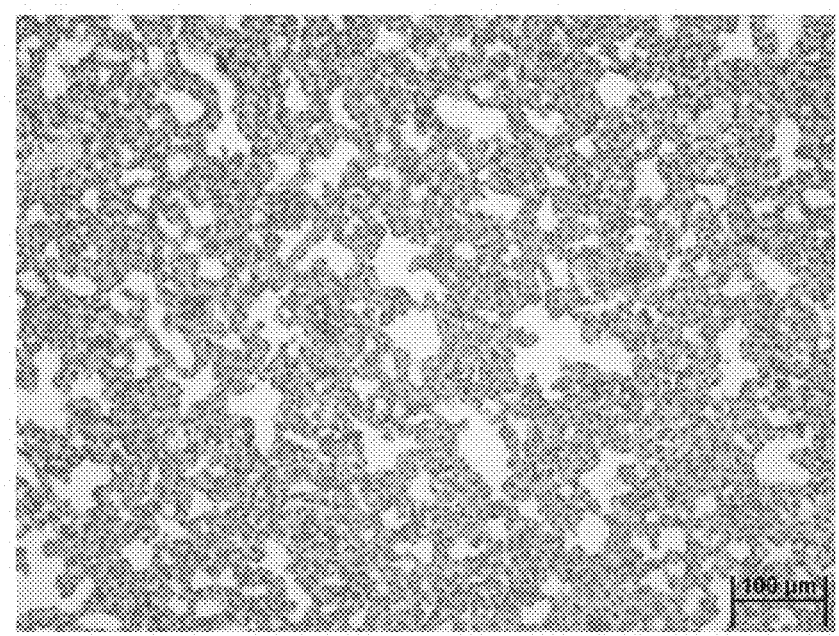

Other animal models of TRALI typically utilize a 'two-hit' model that directs the inflammatory response to the lungs (reviewed in references). One method of inducing the 'first hit' is infusion of LPS which after intravenous infusion will initially encounter the capillary beds of the lungs likely priming them for overt damage by the 'second hit'. A 2 mg/kg LPS IV injection given as a 'first-hit' 30 minutes prior to the 'second-hit' with transfusion of 30% mismatched erythrocytes resulted in dramatic lung damage at 4 hours post transfusion with massive neutrophil infiltration of lung tissue (FIG. 9D). A corresponding change in intravascular leucocyte levels was also observed with significant reduction of WBC ($P=9.8\times10^{-5}$), neutrophils ($P=4.5\times10^{-4}$), monocytes ($P=0.004$) and a further reduction in lymphocytes ($P=0.006$) in the bloodstream compared to animals receiving the 30% transfusion in the absence of the LPS 'first-hit' (FIGS. 10A-10C). The reduction in circulating leukocytes in this model mimics the transient leukopenia reported in TRALI patients. Together, these results demonstrate that this transfusion-initiated model with complement activation results in severe neutrophil-mediated lung disease consistent with many aspects of TRALI.

Given the inflammatory nature of the intravascular hemolysis observed in this model, increasing the percentage of transfused human RBCs was tested to determine if it would induce a TRALI-like phenotype in the lungs in the absence of the LPS 'first-hit'. Transfusion of 15-45% human RBCs did not result in acute lung injury in the absence of an LPS 'first-hit'. When the LPS 'first-hit' was added, a TRALI-like pathogenesis was observed by histology and other hallmarks of neutrophil mediated lung injury were detected such as severe neutrophil infiltration of lung parenchyma and leukopenia. The need for LPS as a 'first-hit' to induce TRALI in this model is essential and is consistent with the numerous 'two-hit' rat, mouse, sheep and swine models of TRALI reported in the literature.

To establish a 'two-hit' TRALI model, amounts of human RBC (15, 30 or 45%) were initially transfused into rats to optimize the Wistar rat model. For all procedures, rats were sedated with ketamine and acepromazine throughout the course of the experiment with monitoring of vital signs. Groups of rats received transfusion of human RBC intravascularly through the indwelling jugular catheter. Blood samples were collected into EDTA microtainer tubes (Becton Dickinson) from the animals prior to transfusion and then at 0.5, 5, 20, 60, 120 and 360 min after transfusion. These samples were centrifuged at 2,655×g for 5 min to separate out the plasma and sediment the cells. Plasma was aliquoted and the cell pellet was processed separately as described below. Based on pilot experiments with varying amounts of human RBCs (15-45%), 30% human RBC transfusion produced robust complement-mediated hemolysis over 3 hours and was chosen for the TRALI model (FIGS. 8A and 8B).

For the 'two-hit' model, rats were sedated as above and lipopolysaccharide (LPS, from *Salmonella enterica* serotype enteritidis, 2 mg/kg [Millipore-Sigma]) was administered intravascularly through the indwelling jugular catheter as the 'first-hit' similar to other TRALI models (reviewed in references). This was followed 30 minutes later by 30% mismatched RBC transfusion as the 'second-hit'. Blood samples were collected prior to LPS administration and at 4 hours after RBC transfusion for analysis of blood chemistries (SuperChem and CBC, Antech Diagnostics). Upon completion of the final blood draw, the animals were euthanized using isofluorene and guillotine. A necropsy was completed to collect organs for histopathology. Lungs acquired from each animal were weighed and then stored in formalin or frozen at −70° C. Hematoxylin and eosin (H&E) stained sections of formalin fixed tissue were reviewed in a blinded fashion.

To determine if prophylactic administration of PIC1 would attenuate TRALI pathogenesis, this transfusion-based antibody-initiated complement-mediated TRALI model was utilized. Twenty-eight minutes after IV LPS infusion, 160 mg/kg PIC1 or vehicle control was administered IV followed by the 30% mismatched RBC transfusion. For animals receiving PIC1, 160 mg/kg of the pegylated derivative, PA-dPEG24 (PolyPeptide Group) in approximately 0.05 M histidine [pH 6.0], 0.15 M NaCl was administered 2 minutes before human RBC transfusion. The selection of the 160 mg/kg PIC1 dose was established in the intravascular hemolysis Wistar rat model as previously reported. A group of animals receiving vehicle alone and sham animals were also included.

Four hours after transfusion, blood was collected and lung tissue harvested. PIC1 was found to reduce acute lung injury as assessed by histology and lung weights, neutrophil infiltration of lung tissue, leukocyte sequestration, as well as neutrophil activation as quantified by MPO activity and free DNA in the bloodstream. In addition to the TRALI-like injury induced in these animals in the absence of PIC1, significant acute kidney injury (AKI) was observed as assessed by gross morphology, organ weights and increased blood levels of creatinine, BUN/creatinine and the liver enzyme AST (SGOT) (data not shown) which is consistent with the AKI previously reported in the AIHTR model that is attributable to free hemoglobin released by hemolysis of the 15% transfused human RBCs. This type of end-organ damage to the kidney has also been reported in a mouse model of antibody-mediated TRALI. When compared to animals receiving vehicle, PIC1-treated animals had reduced kidney weights and reduction in blood levels of creatinine, BUN/creatinine and AST (data not shown). Thus, even at a 30% transfusion in the presence of LPS pre-treatment, PIC1 protects the kidneys from injury consistent with the protective effect of PIC1 in the AIHTR model.

Example 3

This Example shows that prophylactic administration of PIC1 reduces acute lung injury. IV administration of PIC1 either immediately before or after transfusion of the human RBCs mitigated both hemolysis and kidney damage in an AIHTR model. To ascertain if PIC1 could attenuate TRALI in a novel 'two-hit' model, rats were administered 2 mg/kg LPS IV as the first hit. Twenty-eight minutes later, rats received either 160 mg/kg PIC1 or vehicle only, followed 2 minutes after that by 30% IV transfusion of mismatched RBCs as the second hit. The 160 mg/kg dose of PIC1 was utilized based on its efficacy in the AIHTR model. Four hours after transfusion, animals were sacrificed, lung weights were determined, and lung tissue evaluated by histology.

Figure 11A:
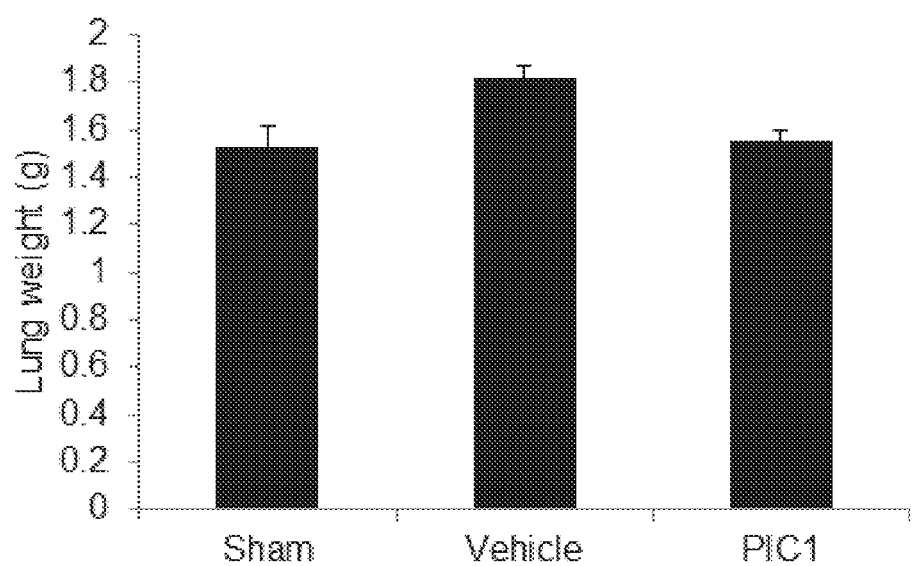
FIGS. 11A-11D show that prophylactically administered PIC1 attenuates acute lung injury.
Figure 11B:
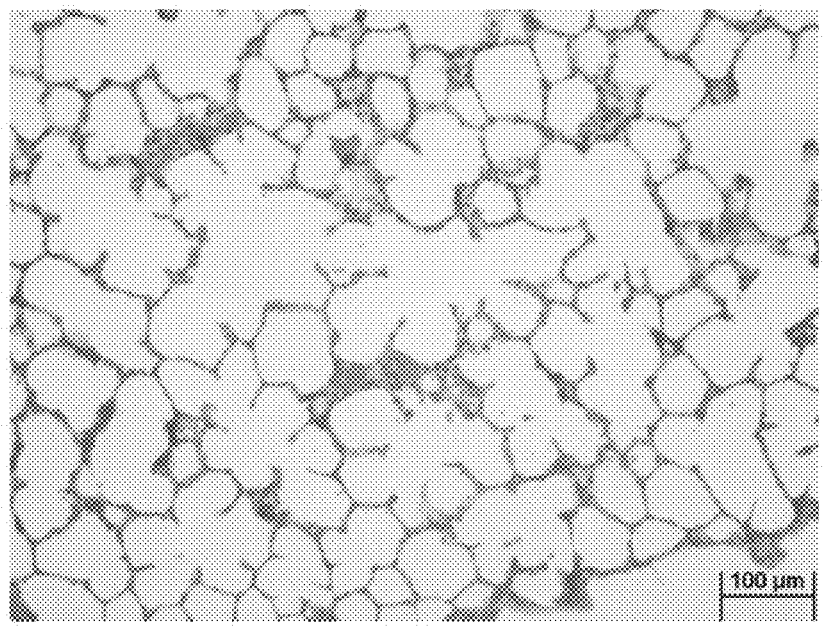
Figure 11C:
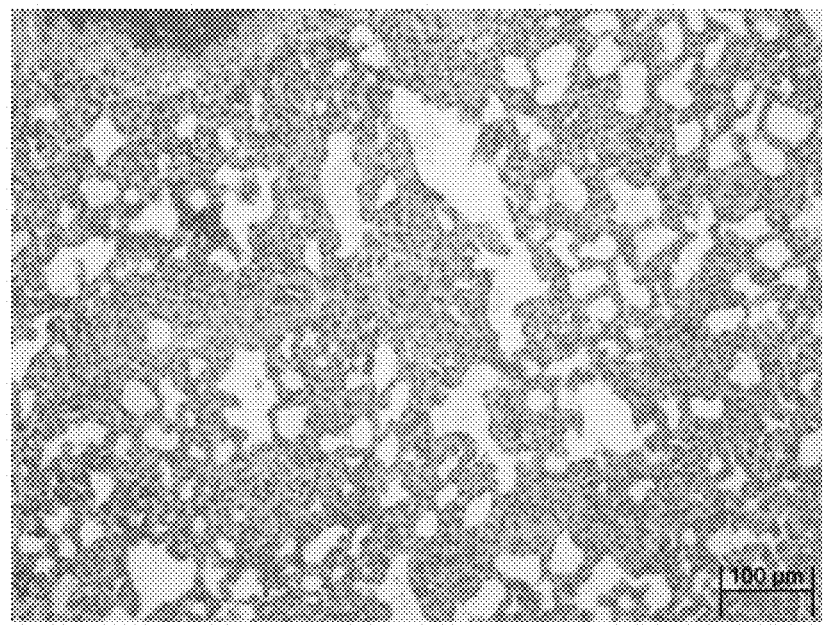
Figure 11D:
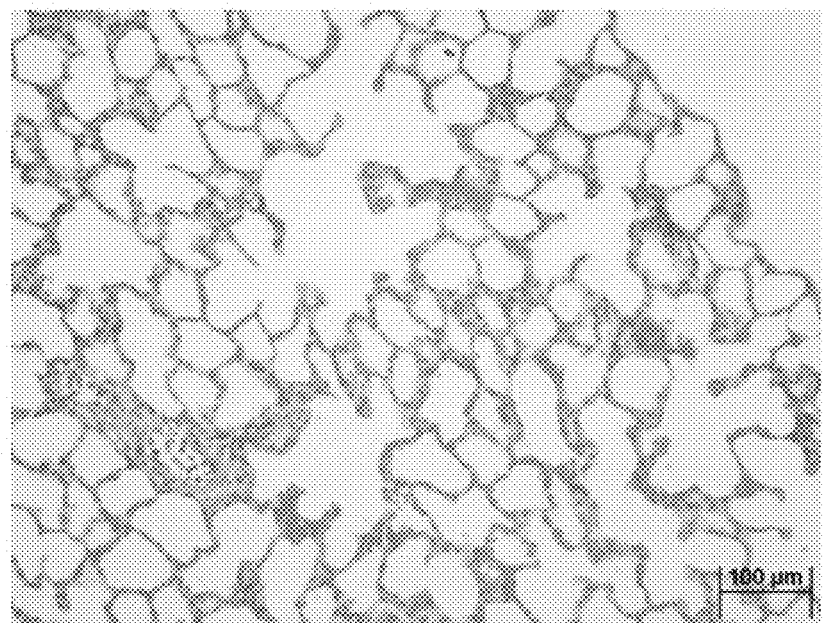

Lungs from vehicle control animals exhibited a significant increase in weight compared to sham animals (p=0.006) consistent with increased cellularity in the lungs (FIG. 11A). In contrast, lungs from the PIC1-treated group showed a significant reduction in lung weight compared to vehicle control animals (p=0.001) and were not significantly different to that of sham animals (p=0.432) (FIG. 11A). Hematoxylin and eosin (H&E) stained sections revealed that compared to the sham animals which demonstrated normal pulmonary histology (FIG. 11B), vehicle-treated animals showed marked consolidation of the alveolar spaces and thickening of the alveolar cell walls with heavy neutrophil infiltration as expected (FIG. 11C). In contrast, animals prophylactically treated with PIC1 showed decreased injury to the lung architecture (FIG. 11D).

Example 4

Figure 12A:
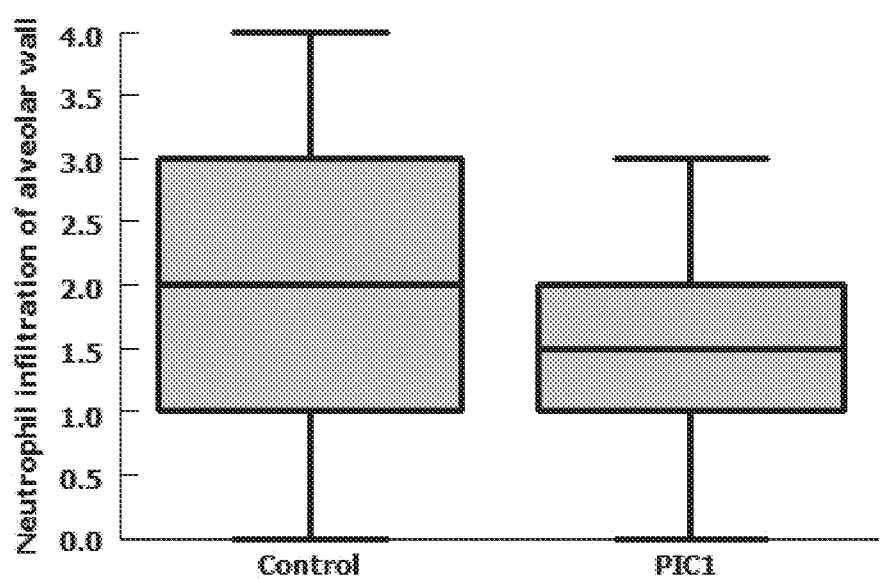
FIGS. 12A-12B are graphs showing that PIC1 reduces neutrophil-mediated lung injury and MPO activity in the lungs.

This Example shows that PIC1 reduces neutrophil-mediated lung injury, myeloperoxidase (MPO) activity and leukopenia. To evaluate the role of PIC1 in attenuating neutrophil mediated lung injury in this model, a blinded grading of H&E sections for neutrophil infiltration and cell wall thickening from vehicle and PIC1-treated animals was performed. Neutrophil infiltration and cell wall thickening were scored on a scale of 0-4 with a score of 0 indicating normal lungs and a score of 4 denoting severe lung injury. Consistent with a reduction in lung weights and histological analysis, animals receiving PIC1 had significantly improved lung injury scores compared to vehicle control animals (p=0.003) (FIG. 12A). Vehicle control animals displayed a higher degree of damage with a mean of 2.0 and a wider distribution compared to PIC1-treated animals with a mean of 1.5 and a much tighter distribution at the 25 and 75 quartiles.

Figure 12B:
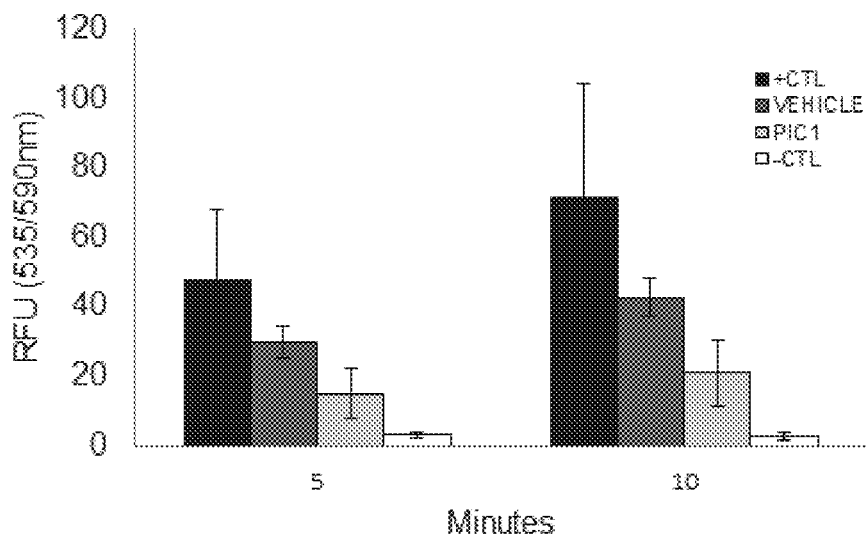

To further evaluate the pathogenic role of neutrophils in this TRALI model, the effect of PIC1 on neutrophil-mediated lung damage via myeloperoxidase (MPO) was evaluated. MPO is the major peroxidase enzyme in neutrophil granules and contributes to inflammatory lung damage via formation of hypochlorous acid and other reactive oxygen species as well as neutrophil extracellular traps (NETs) in many pulmonary diseases. To ascertain if MPO activity could be detected in TRALI lung tissue, extracellular MPO from tissue homogenates of animals receiving PIC1 or vehicle control animals was isolated by antibody capture methodology followed by MPO-mediated oxidation of Amplex Red to fluorescent Resorufin in the presence of hydrogen peroxide. Fluorescence was read from 0 to 10 minutes every 25 seconds. Compared to animals receiving vehicle, PIC1-treated animals had significantly reduced levels of MPO activity at 5 (p=0.005) and 10 minutes (p=0.002) (FIG. 12B).

Figure 13A:
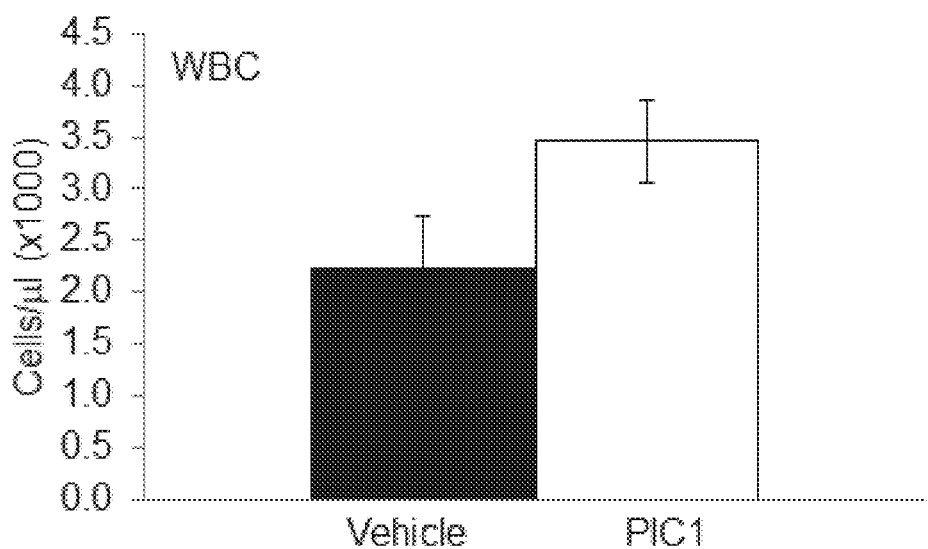
FIGS. 13A-13D are graphs showing that PIC1 reduces leukopenia. Blood was collected from rats receiving vehicle (n=5) or PIC1 (n=8). Levels of WBCs (FIG. 13A), lymphocytes (FIG. 13B), neutrophils (FIG. 13C) and monocytes (FIG. 13D) are reported. The data shown are means and standard error of the mean (SEM).
Figure 13B:
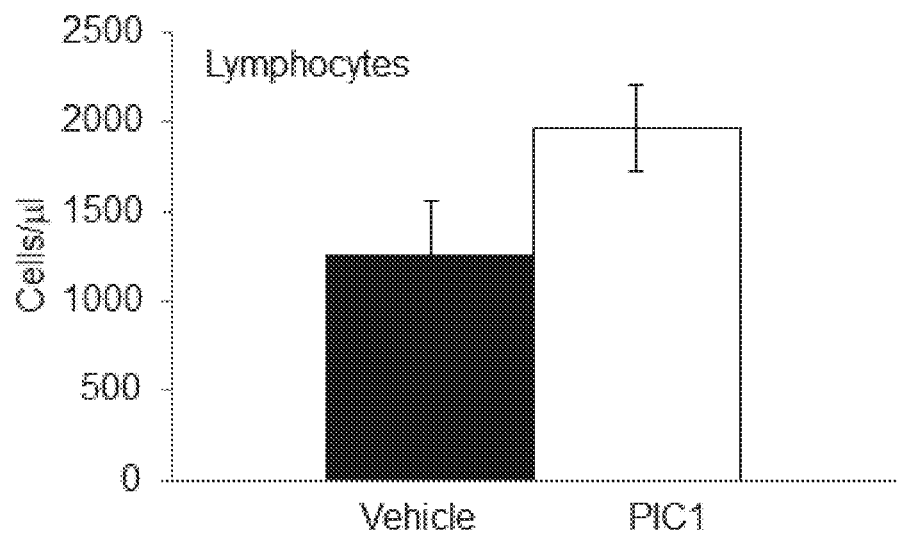
Figure 13C:
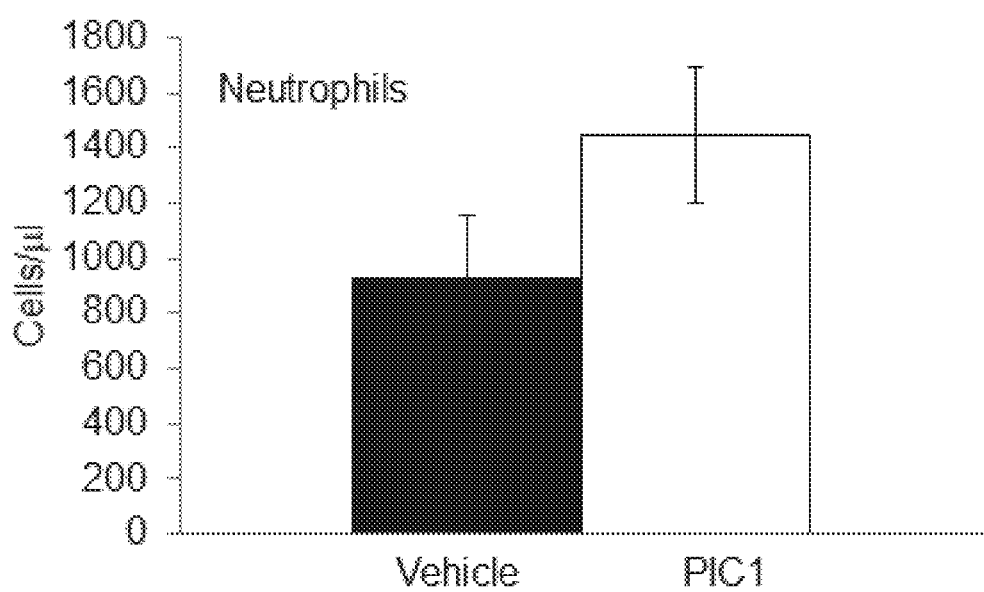
Figure 13D:
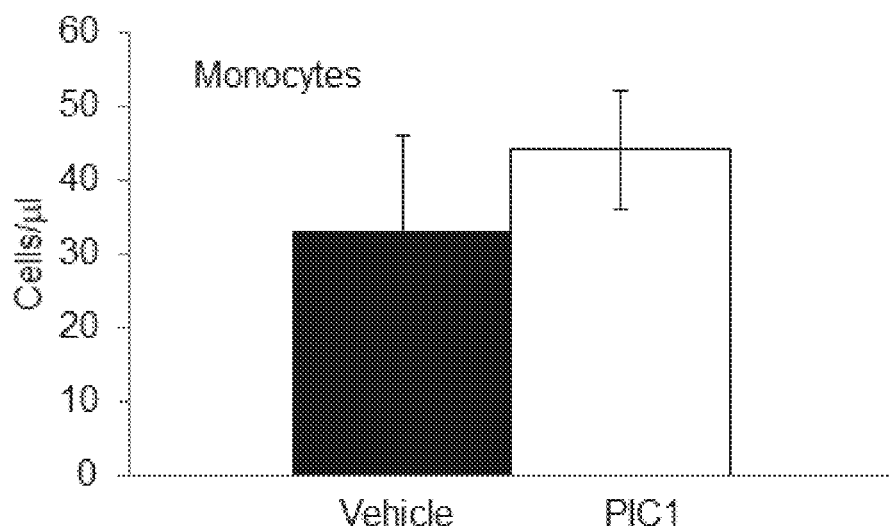

Transient leukopenia may result from neutrophil sequestration in lung tissue and has been observed in animal models of TRALI as well as in patients with TRALI. See also the data in FIG. 10. To ascertain the circulating levels of immune cells in vehicle versus PIC1-treated animals, blood was recovered prior to euthanasia. Compared to animals receiving vehicle, PIC1-treated animals showed a significant increase in blood levels of white blood cells (p=0.043) and lymphocytes (p=0.048) (FIGS. 13A and 13B). Additionally, circulating neutrophils and monocytes also demonstrated trends towards increased numbers in the bloodstream of PIC1-treated animals compared to animals receiving vehicle, but did not reach statistical significance (neutrophils, p=0.101; monocytes, p=0.229), (FIGS. 13C and 13D, respectively).

Example 5

Figure 14:
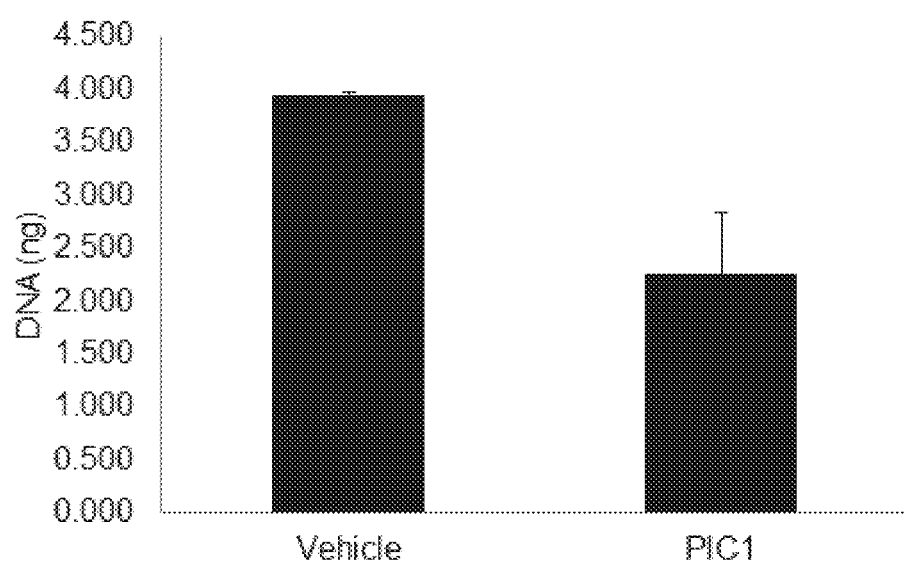
FIG. 14 is a graph showing that PIC1 reduces the level of free DNA in circulation. Plasma samples from animals receiving vehicle (n=3) or PIC1 (n=3) were incubated with PicoGreen. Fluorescence was read at an excitation wavelength of 485 nm and an emission wavelength of 520 nm in a microplate reader. All free DNA measurements for each animal were done in triplicate. The data shown are means and standard error of the mean (SEM).

This Example shows that PIC1 reduces levels of neutrophil extracellular trap (NET) biomarkers in circulation. In murine models of TRALI, activated neutrophils can release NETs contributing to acute lung injury and that the NET biomarker free DNA is elevated in the blood of TRALI patients. To ascertain whether PIC1 had an effect on the level of free DNA in circulation, DNA levels in plasma from animals receiving PIC1 or vehicle were quantified in a PicoGreen assay. Compared to animals receiving vehicle, the level of free DNA in plasma isolated from PIC1-treated animals was significantly reduced (p=0.02) (FIG. 14). Taken together, the reduction of neutrophil-mediated lung injury as assessed by histology, the reduction in MPO activity in the lung tissue, the lack of leukopenia and reduction in free DNA in circulation demonstrate that PIC1 reduces immune cell-mediated acute lung injury in this novel TRALI animal model.

Example 6

This example describes experiments to test the extent to which PA-dPEG24 could inhibit MPO activity and NET formation in vivo. An inflammatory peritonitis model in rats was developed utilizing purified MPO injected intraperitoneally (IP).

Human neutrophil MPO (Lee Biosolutions) was diluted in sterile saline to the respective doses necessary for each experiment. PIC1 in the form of PA-dPEG24 (PolyPeptide Group) was solubilized and diluted in 0.5 M Histidine buffer, adjusted to pH 6.5, and then diluted to each of the respective doses used for each experiment.

Wistar rats were sedated and injected IP with purified MPO in experiments that were conducted under an Eastern Virginia Medical School IRB approved protocol (#17-008). 16-week-old male Wistar rats were used in these experiments weighing approximately 200 g. The rats received sedation with ketamine and acepromazine prior to all procedures. They then received a 1 ml IP injection with MPO in saline. After the time interval indicated, a tail vein phlebotomy was performed to obtain 250 mcl of blood in a $K_2EDTA$ Microtainer (BD). The animals were then euthanized with FatalPlus IV. A peritoneal wash with 20 ml of ice cold PBS was then performed by IV injection followed by massage and extraction from a small hole in the peritoneum with a blunt needle and syringe.

Cells were sedimented and supernatants were tested for MPO peroxidation of TMB, with sample processing performed as follows. Peritoneal wash fluid was centrifuged at 1500×g for 5 minutes to sediment cells and other debris. The resulting peritoneal wash fluid supernatant was aliquoted and frozen for further analysis. The cell pellet was resuspended to the original volume with saline and cells were counted on a hemocytometer. Plasma was collected after centrifugation of the lavender top blood collection tubes.

The MPO activity assay was performed as follows. Peritoneal fluid, along with pure MPO for a standard curve, was serially titrated in 0.1 ml in a 96 well plate followed by the addition of 0.1 ml of 3,3',5,5'-tetramethylbenzidine (TMB) (Fisher). After one minute, 0.1 ml of 2.5 M $H_2SO_4$ was added to stop the reaction and the plate was read at 450 nm. Using linear regression from the standard curve, the MPO activity was calculated for each sample.

Figure 17:
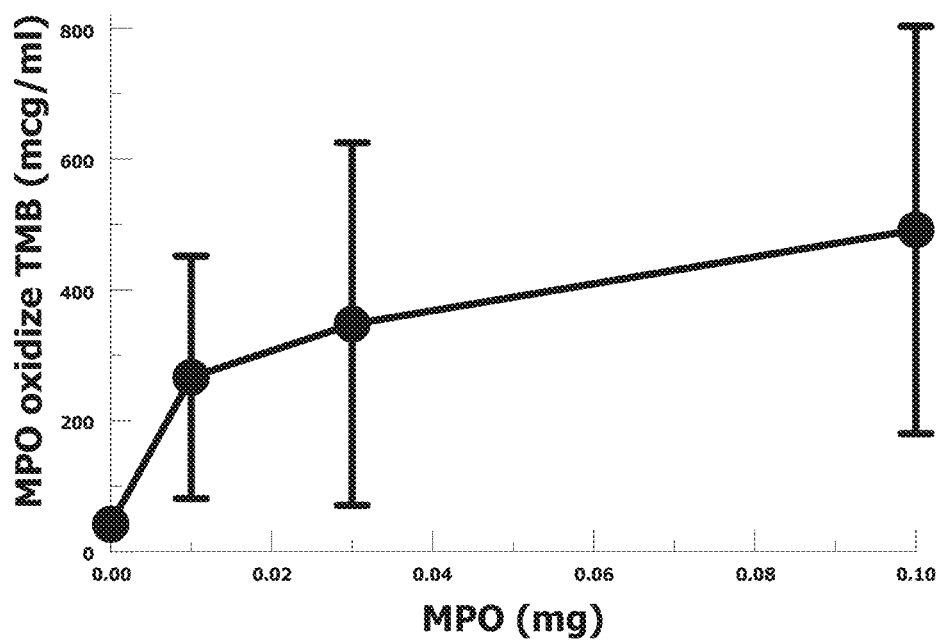
FIG. 17 is a graph in which increasing doses of purified MPO injected by IP show increased TMB peroxidation in peritoneal wash samples. Increasing amounts of purified MPO were injected IP and after one hour, animals underwent phlebotomy, euthanasia and peritoneal wash. Peritoneal wash supernatant oxidation of TMB (n=4) was measured. The data shown are means of independent animals±SEM.

MPO-mediated peritonitis dose-response experiments were performed as follows. A dose response pilot experiment was performed to determine a dose of purified MPO that would demonstrate MPO-mediated peroxidase activity and NET formation. Purified MPO was injected IP into the rats at doses of 0.01, 0.03 and 0.1 mg. After one hour, the rats were euthanized, and peritoneal lavage was performed. The results are shown in FIG. 17. With the MPO dose increasing to 0.1 mg, a trend towards increased peroxidase activity (P=0.12) in the peritoneal lavage fluid measured by a TMB-based assay was demonstrated.

In the peritoneal wash fluid supernatants, free DNA was measured as a marker of NETosis via the PicoGreen assay. Peritoneal fluid or plasma, along with DNA (Invitrogen) for a standard curve, was serially titrated in 0.1 ml in a 96 well plate and used in the Quant-iT PicoGreen (Fisher) assay. The PicoGreen solution was diluted as directed by the kit instructions and added to samples, which were incubated in the dark for 10 minutes and then read on a fluorescent microplate reader at excitation 480 nm/emission 520 nm). Using linear regression from the standard curve, the DNA concentration was quantitated for each sample.

Figure 18:
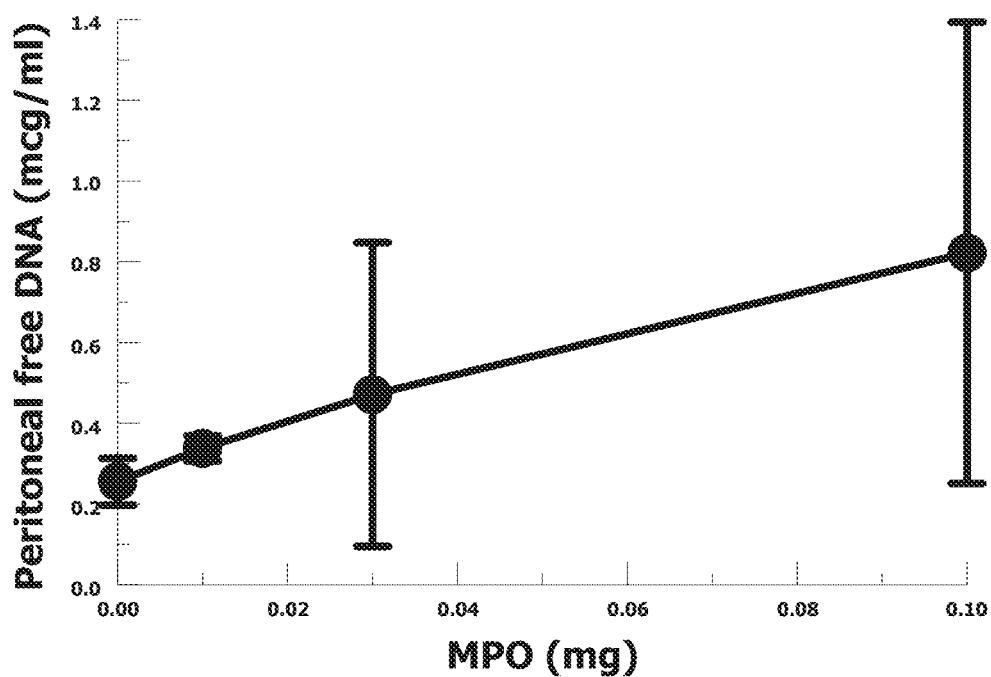
FIG. 18 is a graph in which increasing doses of purified MPO IP demonstrate increased free DNA in peritoneal wash samples. Increasing amounts of purified MPO was injected IP and after one hour, animals underwent phlebotomy, euthanasia and peritoneal wash. Peritoneal wash supernatant free DNA was measured via PicoGreen assay (n=4). The data shown are means of independent animals±SEM.

The results shown in FIG. 18. A trend towards increased free DNA was noted as the dose increased to 0.1 mg MPO dose (P=0.19). The results of these experiments suggested a dose-response relationship where the highest dose of MPO, i.e., 0.1 mg, was more likely to show more activity than the lower doses tested.

To summarize, MPO injected IP in rats resulted in increased peroxidation activity in the peritoneum (FIG. 17) and increased free DNA that is suggestive of NETosis (FIG. 18).

Figure 19:
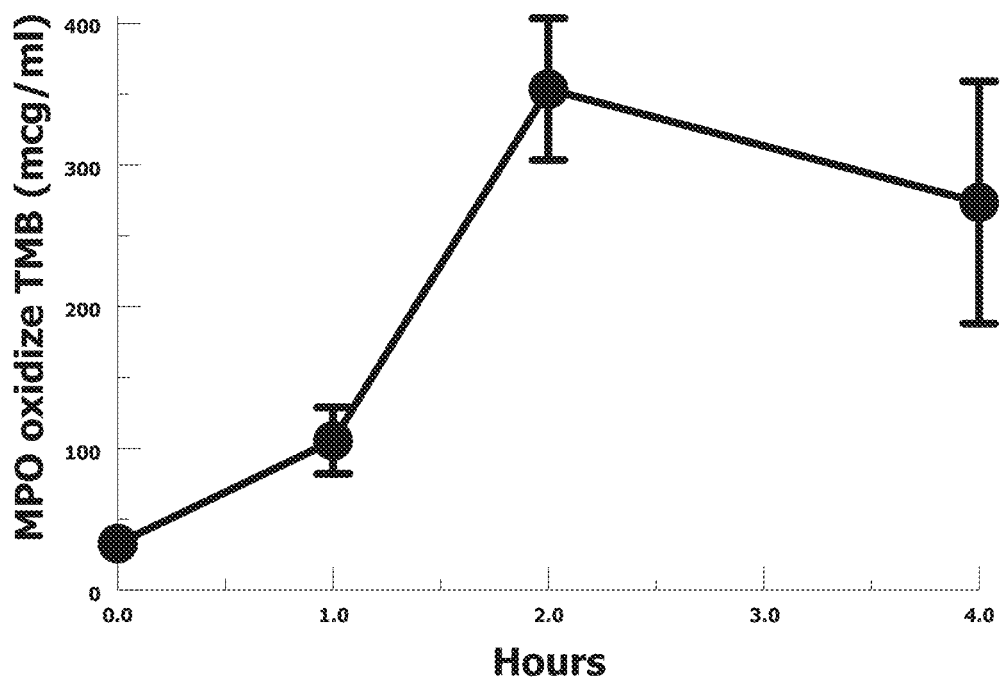
FIG. 19 is a graph showing the results of intraperitoneal MPO time course experiments. Purified MPO (0.1 mg) was injected IP and at increasing intervals animals underwent phlebotomy, euthanasia and peritoneal wash. Peritoneal wash supernatant oxidation of TMB (n=4) was measured. The data shown are means of independent animals±SEM.
Figure 20:
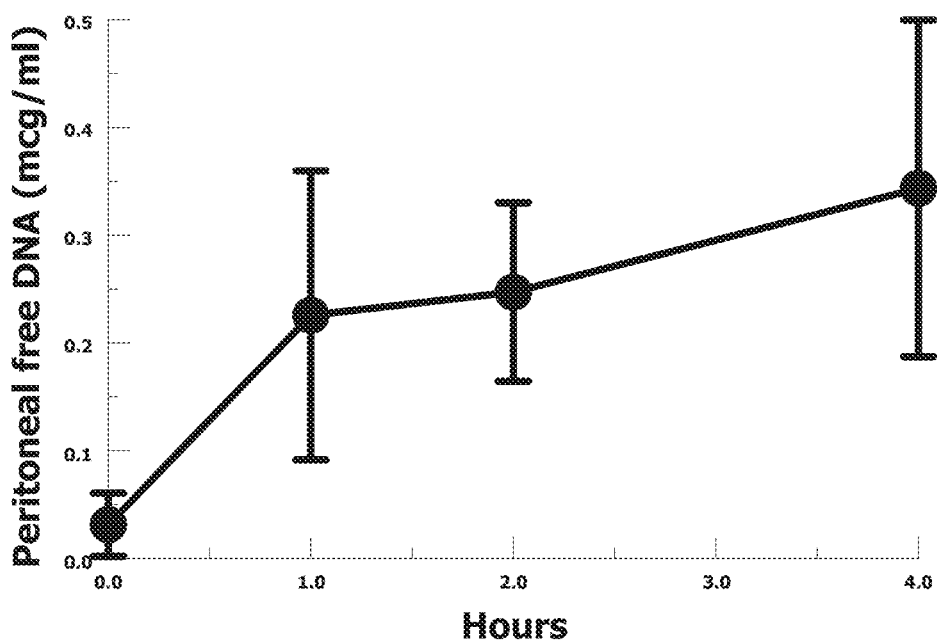
FIG. 20 is a graph showing the results of intraperitoneal MPO time course experiments. Purified MPO (0.1 mg) was injected IP and at increasing intervals animals underwent phlebotomy, euthanasia and peritoneal wash. Peritoneal wash supernatant free DNA was measured via PicoGreen assay (n=4). The data shown are means of independent animals±SEM.

MPO-mediated peritonitis time course experiments were then performed. A time course experiment was conducted to evaluate the optimal dwell time for the purified MPO in the peritoneum in this model. MPO was administered IP at a higher 0.1 mg dose and peritoneal washes were performed after euthanasia at 1, 2 and 4 hours after MPO injection. As shown in FIG. 19, a ten-fold increase in MPO peroxidase activity was demonstrated at 2 hours after injection (P=0.005) without further increase at 4 hours. An eight-fold increase in free DNA was demonstrated at 2 hours after injection (P=0.03), as shown in FIG. 20. These results suggested that purified MPO injected IP increased peroxidase activity and NETosis in the peritoneal wash fluid at 2 hours after injection.

The effect of PIC1, in particular PA-dPEG24, on the inhibition of MPO and NETosis in MPO-mediated peritonitis was then assayed. A series of increasing doses of PA-dPEG24 (1 mg, 5 mg, and 20 mg) were injected IP immediately, i.e., one minute after purified MPO was inoculated, into the peritoneum followed 2 hours later by phlebotomy, euthanasia and peritoneal wash. A control was used where no PA-dPEG24 was administered. An MPO activity assay and a free DNA assay according to the methods discussed above were conducted for each of 0 mg, 1 mg, 5 mg, and 20 mg PA-dPEG24 doses.

Figure 21:
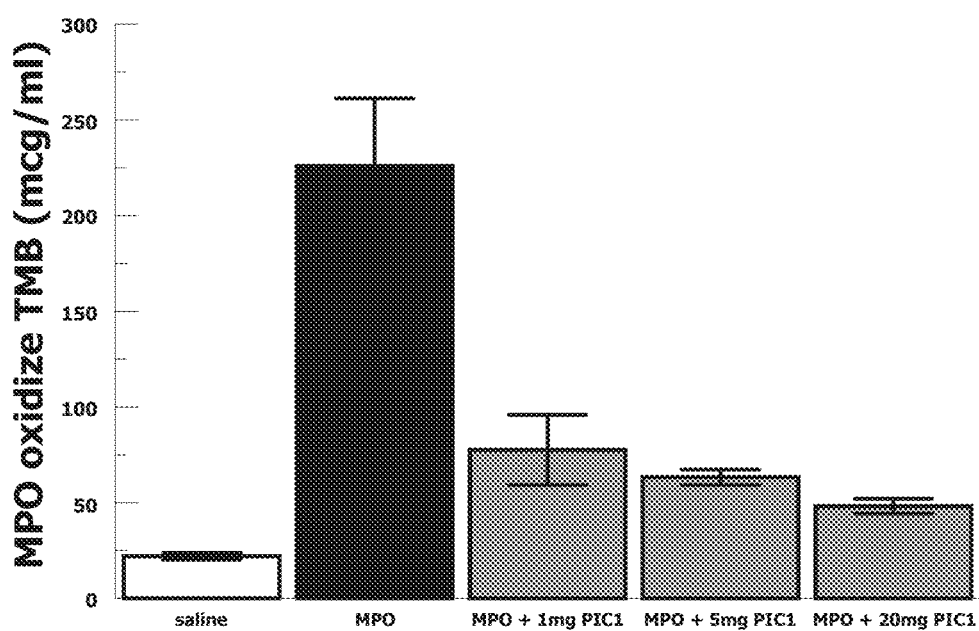
FIGS. 21-23 are graphs showing intraperitoneal MPO with increasing doses of PIC1. Purified MPO (0.1 mg) was injected IP immediately followed by PIC1 injection IP at increasing doses. Two (2) hours after IP injections, animals underwent phlebotomy, euthanasia and peritoneal wash.
Figure 22:
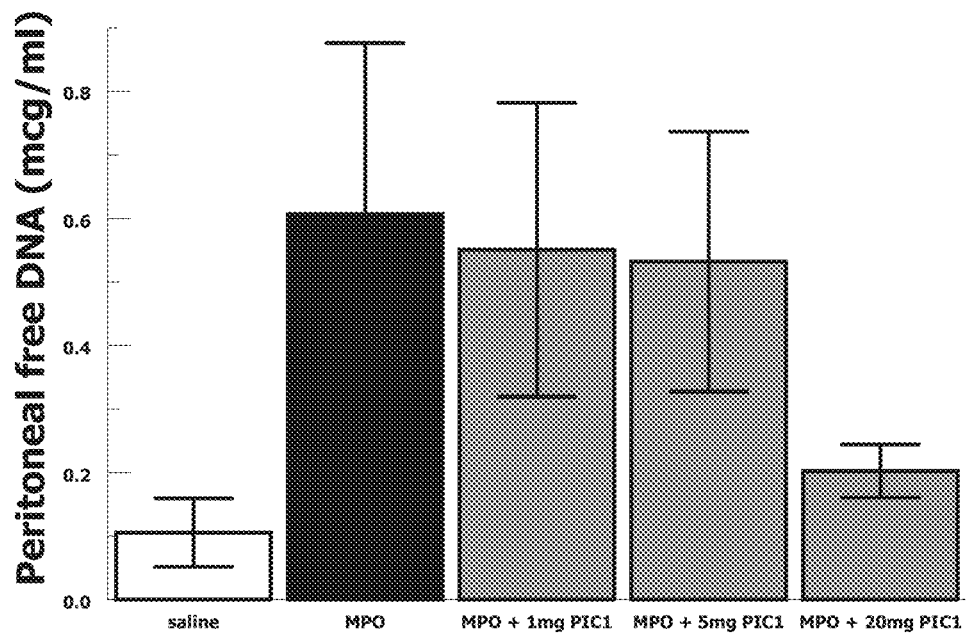

The results for the MPO activity assay are shown in FIG. 21 and those for the free DNA assay (in peritoneal wash supernatant free DNA) are shown in FIG. 22. PIC1 injected IP in this model showed a decreased peroxidation activity in the peritoneum (FIG. 21) and showed a trend towards decreased NETosis (FIG. 22). In particular, a 20 mg dose (100 mg/kg) of PA-dPEG24 demonstrated a 5-fold decrease (P=0.015) in peroxidase activity by TMB compared with no PA-dPEG24 after MPO injection. Statistically significant decreases in MPO activity (P<0.019) were also demonstrated for PA-dPEG24 doses of 5 mg (25 mg/kg) and 1 mg (5 mg/kg). A trend towards decreased free DNA in the peritoneal fluid (P=0.11) was noted for the 20 mg (100 mg/kg) dose of PA-dPEG24, as compared with no PA-dPEG24.

Figure 23:
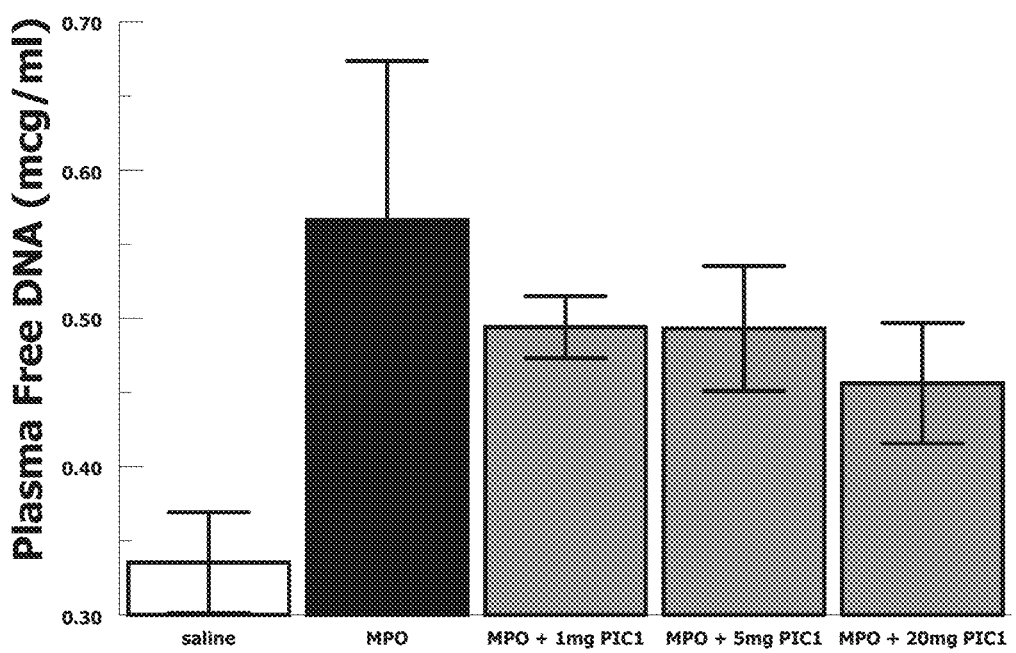

Free DNA was also measured in the blood plasma, with the results shown in FIG. 23. A similar trend was found in which free DNA was lowest with the highest dose of PA-dPEG24 (P=0.22), as compared with no PIC1 after MPO injection. These results demonstrate that PA-dPEG24 can decrease MPO-mediated peroxidase activity in vivo in this purified MPO peritonitis model. The results also suggest that PA-dPEG24 may be able to decrease MPO-mediated NETosis in vivo.

REFERENCES

1. Ballanti E, Perricone C, Greco E, Ballanti M, Di Muzio G, Chimenti M S, et al. Complement and autoimmunity. *Immunologic research.* 2013; 56(2-3):477-91. doi: 10.1007/S12026-013-8422-y. PubMed PMID: 23615835.
2. Barilla-Labarca M L, Toder K, Furie R. Targeting the complement system in systemic lupus erythematosus and other diseases. *Clinical immunology.* 2013; 148(3):313-21. doi: 10.1016/j.clim.2013.02.014. PubMed PMID: 23623037.
3. Daha N A, Banda N K, Roos A, Beurskens F J, Bakker J M, Daha M R, et al. Complement activation by (auto-) antibodies. *Molecular immunology.* 2011; 48(14):1656-65. doi: 10.1016/j.molimm.2011.04.024. PubMed PMID: 21757235.
4. Zawrotniak M, Rapala-Kozik M. Neutrophil extracellular traps (NETs)—formation and implications. *Acta biochimica Polonica.* 2013; 60(3):277-84. PubMed PMID: 23819131.
5. Knight J S, Kaplan M J. Lupus neutrophils: 'NET' gain in understanding lupus pathogenesis. Current opinion in rheumatology. 2012; 24(5):441-50. doi: 10.1097/BOR.0b013e3283546703. PubMed PMID: 22617827.
6. Lood C, Blanco L P, Purmalek M M, Carmona-Rivera C, De Ravin S S, Smith C K, et al. Neutrophil extracellular traps enriched in oxidized mitochondrial DNA are interferogenic and contribute to lupus-like disease. *Nature medicine.* 2016; 22(2):146-53. doi: 10.1038/nm.4027. PubMed PMID: 26779811; PubMed Central PMCID: PMC4742415.
7. Bassi N, Del Prete D, Ghirardello A, Gatto M, Ceol M, Zen M, et at PTX3, Anti-PTX3, and Anti-C1q Autoantibodies in Lupus Glomerulonephritis. Clinical reviews in allergy & immunology. 2015; 49(2):217-26. doi: 10.1007/s12016-015-8476-9. PubMed PMID: 25805362.
8. Orbai A M, Truedsson L, Sturfelt G, Nived 0, Fang H, Alarcon G S, et al. Anti-C1q antibodies in systemic lupus erythematosus. *Lupus.* 2015; 24(1):42-9. doi: 10.1177/0961203314547791. PubMed PMID: 25124676; PubMed Central PMCID: PMC4268323.
9. Thanei S, Vanhecke D, Trendelenburg M. Anti-C1q autoantibodies from systemic lupus erythematosus patients activate the complement system via both the classical and lectin pathways. *Clinical immunology.* 2015; 160(2):180-7. doi: 10.1016/j.clim.2015.06.014. PubMed PMID: 26148903.
10. Coulthard L G, Woodruff T M. Is the Complement Activation Product C3a a Proinflammatory Molecule? Re-evaluating the Evidence and the Myth. *J Immunol.* 2015; 194(8):3542-8. doi: 10.4049/jimmunol.1403068. PubMed PMID: 25848071.
11. Tralau T, Meyer-Hoffert U, Schroder J M, Wiedow O. Human leukocyte elastase and cathepsin G are specific inhibitors of C5a-dependent neutrophil enzyme release and chemotaxis. *Experimental dermatology.* 2004; 13(5):316-25. doi: 10.1111/j.0906-6705.2004.00145.x. PubMed PMID: 15140022.
12. Lupia E, Del Sorbo L, Bergerone S, Emanuelli G, Camussi G, Montrucchio G. The membrane attack complex of complement contributes to plasmin-induced synthesis of platelet-activating factor by endothelial cells and neutrophils. *Immunology.* 2003; 109(4):557-63. PubMed PMID: 12871223; PubMed Central PMCID: PMC1783006.
13. Mayadas T N, Tsokos G C, Tsuboi N. Mechanisms of immune complex-mediated neutrophil recruitment and tissue injury. *Circulation.* 2009; 120(20):2012-24. doi: 10.1161/CIRCULATIONAHA.108.771170. PubMed PMID: 19917895; PubMed Central PMCID: PMC2782878.
14. Chen K, Nishi H, Travers R, Tsuboi N, Martinod K, Wagner D D, et al. Endocytosis of soluble immune complexes leads to their clearance by FcgammaRIIIB but induces neutrophil extracellular traps via FcgammaRIIA in vivo. *Blood.* 2012; 120(22):4421-31. doi: 10.1182/blood-2011-12-401133. PubMed PMID: 22955924; PubMed Central PMCID: PMC3507149.
15. Behnen M, Leschczyk C, Moller S, Batel T, Klinger M, Solbach W, et al. Immobilized immune complexes induce neutrophil extracellular trap release by human neutrophil granulocytes via FcgammaRIIB and Mac-1. *J Immunol.* 2014; 193(4):1954-65. doi: 10.4049/jimmunol.1400478. PubMed PMID: 25024378.
16. Kraaij T, Tengstrom F C, Kamerling S W, Pusey C D, Scherer H U, Toes R E, et al. A novel method for high-throughput detection and quantification of neutrophil extracellular traps reveals ROS-independent NET release with immune complexes. *Autoimmunity reviews.* 2016; 15(6):577-84. doi: 10.1016/j.autrev.2016.02.018. PubMed PMID: 26925759.
17. Aleyd E, Al M, Tuk C W, van der Laken C J, van Egmond M. IgA Complexes in Plasma and Synovial Fluid of Patients with Rheumatoid Arthritis Induce Neutrophil Extracellular Traps via FcalphaRl. *J Immunol.* 2016; 197(12):4552-9. doi: 10.4049/jimmunol.1502353. PubMed PMID: 27913645.
18. Akong-Moore K, Chow O A, von Kockritz-Blickwede M, Nizet V. Influences of chloride and hypochlorite on neutrophil extracellular trap formation. *PLoS ONE.* 2012; 7(8):e42984. doi: 10.1371/journal.pone.0042984. PubMed PMID: 22912772; PubMed Central PMCID: PMC3418225.
19. Sharp J A, Whitley P H, Cunnion K M, Krishna N K. Peptide inhibitor of complement cl, a novel suppressor of classical pathway activation: mechanistic studies and clinical potential. *Frontiers in immunology.* 2014; 5:406. doi: 10.3389/fimmu.2014.00406. PubMed PMID: 25202312; PubMed Central PMCID: PMC4141160.
20. Mauriello C T, Pallera H K, Sharp J A, Woltmann J L, Jr., Qian S, Hair P S, et al. A novel peptide inhibitor of classical and lectin complement activation including ABO incompatibility. *Molecular immunology.* 2013; 53(1-2):132-9. doi: 10.1016/j.molimm.2012.07.012. PubMed PMID: 22906481; PubMed Central PMCID: PMC3630508.
21. Sharp J A, Hair P S, Pallera H K, Kumar P S, Mauriello C T, Nyalwidhe J O, et al. Peptide Inhibitor of Complement C1 (PIC1) Rapidly Inhibits Complement Activation after Intravascular Injection in Rats. *PLoS ONE.* 2015; 10(7):e0132446. doi: 10.1371/journal.pone.0132446. PubMed PMID: 26196285.
22. Kumar P S, Pallera H K, Hair P S, Rivera M G, Shah T A, Werner A L, et al. Peptide inhibitor of complement Cl modulates acute intravascular hemolysis of mismatched red blood cells in rats. *Transfusion.* 2016; 56(8):2133-45. doi: 10.1111/trf.13674. PubMed PMID: 27282513.
23. Hair P S, Sass L A, Krishna N K, Cunnion K M. Inhibition of Myeloperoxidase Activity in Cystic Fibrosis Sputum by Peptide Inhibitor of Complement C1 (PIC1). *PLoS ONE.* 2017; 12(1):e0170203. doi: 10.1371/journal.pone.0170203. PubMed PMID: 28135312.

24. Hair P S, Cunnion K M, Krishna N K. Peptide inhibitor of complement C1 (PIC1) inhibits the peroxidase activity of hemoglobin and myoglobin. *International Journal of Peptides.* 2017; In Press.
25. Bergseth G, Ludviksen J K, Kirschfink M, Giclas P C, Nilsson B, Mollnes T E. An international serum standard for application in assays to detect human complement activation products. *Molecular immunology.* 2013; 56(3): 232-9. doi: 10.1016/j.molimm.2013.05.221. PubMed PMID: 23787367.
26. Bonaparte R S, Hair P S, Banthia D, Marshall D M, Cunnion K M, Krishna N K. Human astrovirus coat protein inhibits serum complement activation via C1, the first component of the classical pathway. *Journal of virology.* 2008; 82(2):817-27. PubMed PMID: 17959658.
27. Steil A A, Garcia Rodriguez M C, Alonso A, Crespo M S, Bosca L. Platelet-activating factor: the effector of protein-rich plasma extravasation and nitric oxide synthase induction in rat immune complex peritonitis. *British journal of pharmacology.* 1995; 114(4):895-901. PubMed PMID: 7539698.
28. Bestebroer J, Aerts P C, Rooijakkers S H, Pandey M K, Kohl J, van Strijp J A, et al. Functional basis for complement evasion by staphylococcal superantigen-like 7. *Cellular microbiology.* 2010; 12(10):1506-16. PubMed PMID: 20545943.
29. Cunnion K M, Lee J C, Frank M M. Capsule production and growth phase influence binding of complement to *Staphylococcus aureus. Infection and immunity.* 2001; 69(11):6796-803. PubMed PMID: 11598052.
30. Kumar P S, Mauriello C T, Hair P S, Rister N S, Lawrence C, Raafat R H, et al. Glucose-based dialysis fluids inhibit innate defense against *Staphylococcus aureus. Molecular immunology.* 2015; 67(2 Pt B):575-83. doi: 10.1016/j.molimm.2015.07.017. PubMed PMID: 26256795.
31. Hair P S, Echague C G, Sholl A M, Watkins J A, Geoghegan J A, Foster T J, et al. Clumping factor A interaction with complement factor I increases C3b cleavage on the bacterial surface of *Staphylococcus aureus* and decreases complement-mediated phagocytosis. *Infection and immunity.* 2010; 78(4):1717-27. PubMed PMID: 20100856.
32. Carlin J B, Doyle L W. Statistics for clinicians: 4: Basic concepts of statistical reasoning: hypothesis tests and the t-test. *Journal of paediatrics and child health.* 2001; 37(1):72-7. PubMed PMID: 11168875.

All references, including publications, patent applications, and patents, cited herein are hereby incorporated by reference to the same extent as if each reference were individually and specifically indicated to be incorporated by reference and were set forth in its entirety herein.

What is claimed is:

1. A method of inhibiting myeloperoxidase (MPO) activity and/or NET formation in a subject, the method comprising:
   administering a therapeutically effective amount of a PIC1 peptide to the subject in need thereof, wherein the PIC1 peptide comprises the sequence of IALILE-PICCQERAA-dPEG24 (SEQ ID NO: 19),
   wherein the PIC1 peptide is administered at a dose of from 5 to 160 mg/kg body weight of the subject.

2. The method of claim 1, wherein the method is effective to inhibit inflammation in the subject.

3. The method of claim 1, wherein the method is effective to inhibit inflammatory tissue damage in the subject.

4. The method of claim 1, wherein the method is effective to preserve normal lung architecture in the subject.

5. The method of claim 1, wherein the method is effective to inhibit one or more of lung damage, neutrophil invasion into lung tissue, and MPO activity.

6. The method of claim 1, wherein the method is effective to modulate immune complex activation of the complement system in the subject.

7. The method of claim 1, wherein the PIC1 peptide is administered at a dose of from 5 to 100 mg/kg body weight of the subject.

8. The method of claim 1, wherein the PIC1 peptide is administered intravenously.

9. The method of claim 1, wherein the NET formation is stimulated by at least one of a bacterium, a fungus, a parasite or a virus.

10. The method of claim 9, wherein the NET formation is stimulated by a virus.

11. A method of inhibiting one or more of lung damage, neutrophil invasion into lung tissue, and MPO activity in lung tissue in a subject, the method comprising:
    administering a therapeutically effective amount of a PIC1 peptide to the subject in need thereof, wherein the PIC1 peptide comprises the sequence of IALILE-PICCQERAA-dPEG24 (SEQ ID NO: 19),
    wherein the PIC1 peptide is administered at a dose of from 5 to 160 mg/kg body weight of the subject.

12. The method of claim 11, wherein the method is effective to inhibit inflammation in the subject.

13. The method of claim 11, wherein the method is effective to inhibit inflammatory tissue damage in the subject.

14. The method of claim 11, wherein the method is effective to preserve normal lung architecture in the subject.

15. The method of claim 11, wherein the method is effective to inhibit two or more of lung damage, neutrophil invasion into lung tissue, and MPO activity in lung tissue.

16. The method of claim 11, wherein the method is effective to modulate immune complex activation of the complement system in the subject.

17. The method of claim 11, wherein the PIC1 peptide is administered at a dose of from 5 to 100 mg/kg body weight of the subject.

18. The method of claim 11, wherein the PIC1 peptide is administered intravenously.

\* \* \* \* \*